US 11,401,277 B2

(12) United States Patent
Peer Mohamed et al.

(10) Patent No.: US 11,401,277 B2
(45) Date of Patent: Aug. 2, 2022

(54) ANTI-BACTERIAL HETEROCYCLIC COMPOUNDS AND THEIR SYNTHESIS

(71) Applicant: Bugworks Research, Inc., Wilmington, DE (US)

(72) Inventors: Shahul Hameed Peer Mohamed, Bengaluru (IN); Nagakumar Bharatham, Bengaluru (IN); Nainesh Katagihallimath, Bengaluru (IN); Sreevalli Sharma, Bengaluru (IN); Radha Nandishaiah, Bengaluru (IN); Vasanthi Ramachandran, Bengaluru (IN)

(73) Assignee: BUGWORKS RESEARCH, INC., Wilmington, DE (US)

( * ) Notice: Subject to any disclaimer, the term of this patent is extended or adjusted under 35 U.S.C. 154(b) by 89 days.

(21) Appl. No.: 16/763,222

(22) PCT Filed: Nov. 29, 2018

(86) PCT No.: PCT/IN2018/050799
§ 371 (c)(1),
(2) Date: May 11, 2020

(87) PCT Pub. No.: WO2019/106693
PCT Pub. Date: Jun. 6, 2019

(65) Prior Publication Data
US 2021/0070772 A1    Mar. 11, 2021

(30) Foreign Application Priority Data
Nov. 29, 2017   (IN) .............................. 201741042876

(51) Int. Cl.
*C07D 498/04*   (2006.01)
*C07D 513/04*   (2006.01)
*A61P 31/04*   (2006.01)

(52) U.S. Cl.
CPC ............ *C07D 498/04* (2013.01); *A61P 31/04* (2018.01); *C07D 513/04* (2013.01)

(58) Field of Classification Search
CPC ...... C07D 498/04; C07D 513/04; A61P 31/04
See application file for complete search history.

(56) References Cited

FOREIGN PATENT DOCUMENTS

WO    2013021363 A1    2/2013
WO    2013068948 A1    5/2013

OTHER PUBLICATIONS

Bush, Karen, "Why It Is Important to Continue Antibacterial Drug Discovery," ASM News, vol. 70, pp. 282-287 (2004).
International Preliminary Report on Patentability dated Jun. 2, 2020 in International Application No. PCT/IN2018/050799.
International Search Report and Written Opinion dated Jan. 21, 2019 in International Application No. PCT/IN2018/050799.

*Primary Examiner* — Laura L Stockton
(74) *Attorney, Agent, or Firm* — Panitch Schwarze Belisario & Nadel LLP

(57) ABSTRACT

The invention relates to compounds of Formula I and Formula (B) along with their stereoisomers, pharmaceutically acceptable salts, complexes, hydrates, solvates, tautomers, polymorphs, racemic mixtures, optically active forms, and pharmaceutically active derivatives thereof. These compounds are useful for killing or inhibiting the growth of a microorganism selected from the group consisting of bacteria, virus, fungi, and protozoa.

22 Claims, No Drawings

ANTI-BACTERIAL HETEROCYCLIC COMPOUNDS AND THEIR SYNTHESIS

CROSS-REFERENCE TO RELATED APPLICATIONS

This application is a Section 371 of International Application No. PCT/IN2018/050799, filed Nov. 29, 2018, which was published in the English language on Jun. 6, 2019, under International Publication No. WO 2019/106693 A1, which is incorporated herein by reference in its entirety, which claims priority under 35 U.S.C. § 119(b) to Indian Application No. 201741042876, filed Nov. 29, 2017.

FIELD OF THE INVENTION

The present disclosure relates to the field of medicinal chemistry and more particularly to the synthesis, characterization and development of bacterial topoisomerase inhibitors effective against Gram-positive and Gram-negative bacterial species with a broad spectrum of antibacterial activity. In particular the present disclosure relates to compounds of Formula I, their stereoisomers, pharmaceutically acceptable salts, complexes, hydrates, solvates, tautomers, polymorphs, racemic mixtures, optically active forms and pharmaceutically active derivatives thereof and pharmaceutical compositions containing them as active ingredient.

BACKGROUND OF THE INVENTION

Antimicrobial agents are basically the substances that kill or inhibit the growth of microorganisms. These substances can be derived either from natural sources or can be prepared synthetically. Due to their utility in the treatment of infections, antimicrobial agents remain a serious concern for the World Health Organization as they form essential components of drugs used for human and animal health, and welfare (Bush, K., ASM News, 2004, 70, 282-287).

Despite the efforts to furnish improved antimicrobials in the market, bacteria continue to evolve over these newly developed antimicrobial agents through their efficient resistance mechanism. Resistance to the antimicrobial agents has emerged as a global public health concern in the past few years. The growing adverse impact on public health, therefore, remains the driving force for the innovation and development of new antimicrobial agents.

The world expects to have effective drugs available for every disease, but resistance is a growing menace to this regime and therefore biologically active compounds exhibiting potent antimicrobial activity need to be developed. Based on their structural diversity and wide spectrum biological activity, heterocyclic compounds could be taken in consideration as promising compounds that could overcome the resistance problems existing with the current antimicrobial agents.

SUMMARY OF THE INVENTION

The present disclosure provides a compound of Formula I

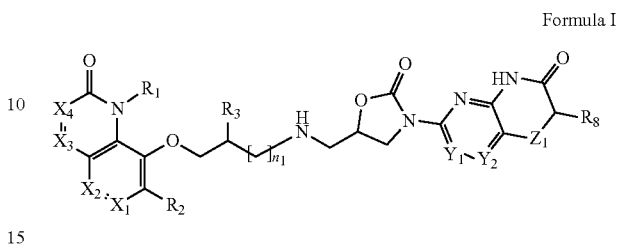

Formula I or its stereoisomers, pharmaceutically acceptable salts, complexes, hydrates, solvates, tautomers, polymorphs, racemic mixtures, optically active forms, and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-6}$ alkoxy, or hydroxyl; $R_3$ is selected from hydrogen, $C_{1-6}$ alkyl, fluorine, $C_{1-6}$ alkoxy, hydroxyl, or amino; $X_1$ is N or $CR_4$; $R_4$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_3$ is N or $CR_6$; and $X_4$ is $CR_6$ when dotted line (----) represents a bond; $R_6$ is selected from hydrogen, cyano, $C_{1-6}$ alkyl, $C_{1-6}$ alkylamino, $C_{1-6}$ alkoxy, $C_{1-6}$ haloalkoxy, or COOH; or $X_3$ is $CH_2$ or O; and $X_4$ is $CH_2$ when dotted line (---) represents no bond; $n_1$ is 0 to 2; $Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; and $R_8$ is selected from hydrogen, hydroxyl, $C_{1-6}$ alkyl, or fluorine.

The present disclosure further relates to a compound of Formula I, or its stereoisomers, pharmaceutically acceptable salts, complexes, hydrates, solvates, tautomers, polymorphs, racemic mixtures, optically active forms, and pharmaceutically active derivatives thereof, for use in killing or inhibiting the growth of a microorganism selected from the group consisting of bacteria, virus, fungi, and protozoa.

The present disclosure further relates to use of a compound of Formula I, or its stereoisomers, pharmaceutically acceptable salts, complexes, hydrates, solvates, tautomers, polymorphs, racemic mixtures, optically active forms, and pharmaceutically active derivatives thereof, for use in killing or inhibiting the growth of a microorganism selected from the group consisting of bacteria, virus, fungi, and protozoa.

The present disclosure provides a compound of Formula (B)

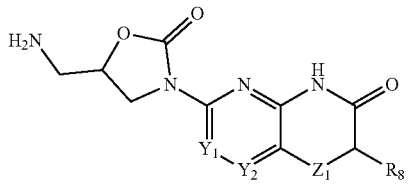

Formula (B)

or its stereoisomers, pharmaceutically acceptable salts, complexes, hydrates, solvates, tautomers, polymorphs, racemic mixtures, optically active forms, and pharmaceutically active derivatives thereof, wherein $Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; and $R_8$ is selected from hydrogen, hydroxyl, $C_{1-6}$ alkyl, or fluorine.

The present disclosure further relates to a compound of Formula I, or its stereoisomers, pharmaceutically acceptable salts, complexes, hydrates, solvates, tautomers, polymorphs, racemic mixtures, optically active forms, and pharmaceutically active derivatives thereof, for use in treating a disease or condition in a patient, wherein said disease or condition is caused by a microorganism selected from the group consisting of Gram-positive, and Gram-negative pathogens.

The present disclosure further relates to use of a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof, in treating a disease or condition in a patient, wherein said disease or condition is caused by a microorganism selected from the group consisting of Gram-positive, and Gram-negative pathogens. The patient is typically a mammal, preferably a human.

The present disclosure further relates to a method of treating a bacterial infection or condition in a subject, said method comprising administering to a subject a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof, wherein said bacterial infection or condition is caused by microorganism selected from the group consisting of Gram-positive, and Gram-negative pathogens.

The present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof together with a pharmaceutically acceptable carrier.

The present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof together with a pharmaceutically acceptable carrier, optionally with one or more other pharmaceutical compositions.

The present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof together with a pharmaceutically acceptable carrier, and in combination with at least one antibiotic.

The present disclosure relates to a process of preparation of compounds of Formula I, or its stereoisomers, pharmaceutically acceptable salts, complexes, hydrates, solvates, tautomers, polymorphs, racemic mixtures, optically active forms, and pharmaceutically active derivatives thereof, said process comprising reacting compounds of Formula (A), and compounds of Formula (B) in presence of at least one reducing agent, and an adsorbent to obtain the compounds of Formula I.

The present disclosure relates to a process of preparation of a composition comprising a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof, together with a pharmaceutically acceptable carrier.

The present disclosure relates to a process of preparation of a composition comprising a compound of Formula I, or Formula (B), or its stereoisomers, pharmaceutically acceptable salts, complexes, hydrates, solvates, tautomers, polymorphs, racemic mixtures, optically active forms, and pharmaceutically active derivatives thereof, together with a pharmaceutically acceptable carrier, optionally in combination with one or more other pharmaceutical compositions.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

In this specification, the prefix $C_{x-y}$ as used in terms such as $C_{x-y}$ alkyl, and the like (where x and y are integers) indicates the numerical range of carbon atoms that are present in the group; for example, $C_{1-6}$ alkyl includes $C_1$ alkyl (methyl), $C_2$ alkyl (ethyl), $C_3$ alkyl (propyl and iso-propyl), and $C_4$ alkyl (butyl, 1-methylpropyl, 2-methylpropyl, and t-butyl). Unless specifically stated, the bonding atom of a group may be any suitable atom of that group; for example, propyl includes prop-1-yl, and prop-2-yl.

The term "alkyl" refers to a monoradical branched or unbranched saturated hydrocarbon chain having from 1 to 6 carbon atoms. This term is exemplified by groups such as n-butyl, iso-butyl, t-butyl, n-hexyl, n-decyl, and the like. The groups may be optionally substituted.

The term "haloalkyl" as used herein refers to an alkyl group in which one or more hydrogen atoms are replaced by the same number of identical or different halogen atoms. The term "haloalkyl" is exemplified by groups such as chloromethyl, trifluoromethyl, 1-fluoroethyl, 2,2,2-trifluoroethyl, and the like.

The term "alkylene" refers to a diradical branched or unbranched saturated hydrocarbon chain having from 1 to 6 carbon atoms. This term is exemplified by groups such as methylene, ethylene, propylene, butylene, hexylene, and the like. The groups may be optionally substituted. Representative substituted alkylene groups include hydroxyl substituted alkylenes, amino substituted alkylene.

The term "alkenyl" refers to a monoradical of a branched or unbranched unsaturated hydrocarbon group preferably having from 2, 3, 4, 5, or 6 carbon atoms, and having 1, 2, or 3, double bond (vinyl), preferably 1 double bond. The groups may be optionally substituted.

The term "cycloalkyl" or "carbocyclyl" refers to carbocyclic groups of from 3 to 6 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, and the like, or multiple ring structures or carbocyclic groups to which is fused an aryl group, for example indane, and the like. The groups may be optionally substituted.

The terms "alkoxyl" or "alkoxy" refers to an alkyl group, as defined above, having an oxygen radical attached thereto. Representative alkoxyl groups include methoxy, ethoxy, propyloxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl.

"Halo" or "Halogen", alone or in combination with any other term means halogens such as chloro or chlorine (Cl), fluoro or fluorine (F), bromo or bromine (Br), and iodo or iodine (I).

The term "heterocyclyl" refers to a heterocyclic ring radical which may be optionally substituted by one or more substituents as described hereinafter in the disclosure. The heterocyclyl ring radical may be attached to the main structure at any heteroatom or carbon atom that results in the creation of a stable structure. Furthermore, the term "heterocyclyl" refers to a stable 3 to 7 membered rings radical, which consists of carbon atoms and from one to five heteroatoms selected from nitrogen, phosphorus, oxygen and sulfur. For purposes of this disclosure the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Preferred heterocyclyl groups include, without limitation, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinylsulfoxide, furyl, tetrahydrofuryl, tetrahydropyranyl, chromanyl and isochromanyl.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituent, and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form, and mixtures thereof. Accordingly, the chemical structures depicted herein encompass all possible tautomeric forms of the illustrated or identified compounds.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic, and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides, and organic bases, for example alkyl amines, arylalkyl amines and heterocyclic amines.

The compounds discussed herein in many instances may have been named and/or checked with ACD/Name by ACD/Labs® and/or Chemdraw by CambridgeSoft®.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "solvate", as used herein, refers to a crystal form of a substance which contains solvent.

The term "hydrate" refers to a solvate wherein the solvent is water.

As discussed in the background section, the effective resistance mechanisms of the microbes (especially bacteria) pose a serious threat to human health. Therefore, new and efficient antimicrobial (antibacterial) agents need to be developed as a measure against the adversaries posed on human health globally by microbes. The present disclosure provides compounds that can act as efficient antibacterial agents combating both the resistant and non-resistant strains.

According to an embodiment, the present disclosure relates to a compound of Formula I

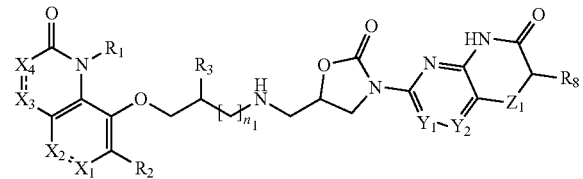

Formula I or its stereoisomers, pharmaceutically acceptable salts, complexes, hydrates, solvates, tautomers, polymorphs, racemic mixtures, optically active forms, and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-6}$ alkoxy, or hydroxyl; $R_3$ is selected from hydrogen, $C_{1-6}$ alkyl, fluorine, $C_{1-6}$ alkoxy, hydroxyl, or amino; $X_1$ is N or $CR_4$; $R_4$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_3$ is N or $CR_6$; and $X_4$ is $CR_6$ when dotted line (----) represents a bond; $R_6$ is selected from hydrogen, cyano, $C_{1-6}$ alkyl, $C_{1-6}$ alkylamino, $C_{1-6}$ alkoxy, $C_{1-6}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, or hydroxyl; $R_3$ is selected from hydrogen, $C_{1-5}$ alkyl, fluorine, $C_{1-5}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, and $CH_2$; or $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$ is selected from N or $CR_7$; $Y_2$ is N; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, and $CH_2$; or $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, chlorine, fluorine, cyano, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$ is selected from N or $CR_7$; $Y_2$ is $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is $C_{1-6}$ alkyl; $R_2$ is selected from hydrogen, fluorine, chlorine, cyano, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is $C_{1-6}$ alkyl, wherein $C_{1-6}$ alkyl is further substituted with 1 to 3 groups independently selected from halogen, amino, or hydroxyl; $R_2$ is selected from hydrogen, fluorine, chlorine, cyano, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is hydrogen; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is fluorine; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is chlorine; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, and hydroxyl; $R_3$ is hydrogen; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, or hydroxyl; $R_3$ is hydroxyl; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, and hydroxyl; $R_3$ is methyl; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-5}$ alkoxy, and hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 0; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-5}$ alkoxy, or hydroxyl; $R_3$ is selected from hydrogen, $C_{1-5}$ alkyl, fluorine, $C_{1-6}$ alkoxy, hydroxyl, or amino; $X_1$ is N or $CR_4$; $R_4$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_2$ is N or $CR_5$; $R_5$ is selected from hydrogen, halogen, cyano, $C_{1-5}$ alkoxy, $C_{1-5}$ haloalkyl, $C_{1-5}$ haloalkoxy, or $C_{1-5}$ alkyl; $X_3$ is N or $CR_6$; and $X_4$ is $CR_6$ when dotted line (----) represents a bond; $R_6$ is selected from hydrogen, cyano, $C_{1-5}$ alkyl, $C_{1-5}$ alkylamino, $C_{1-5}$ alkoxy, $C_{1-5}$ haloalkoxy, or COOH; or $X_3$ is $CH_2$ or O; and $X_4$ is $CH_2$ when dotted line (----) represents no bond; $n_1$ is 1; $Y_1$, and $Y_2$ are independently selected from N or $CR_7$; $R_7$ is selected from hydrogen, halogen, cyano, $C_{1-5}$ alkoxy, $C_{1-5}$ haloalkyl, $C_{1-5}$ haloalkoxy, or $C_{1-5}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-4}$ alkoxy, cyano, or hydroxyl; $R_3$ is selected from hydrogen, fluorine, $C_{1-4}$ alkoxy, hydroxyl, or amino; $X_1$ is N or $CR_4$; $R_4$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_2$ is N or $CR_5$; $R_5$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_3$ is N or $CR_6$; and $X_4$ is $CR_6$ when dotted line (----) represents a bond; $R_6$ is selected from hydrogen, cyano, $C_{1-4}$ alkyl, $C_{1-4}$ alkylamino, $C_{1-4}$ alkoxy, $C_{1-4}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-4}$ alkoxy, cyano, or hydroxyl; $R_3$ is selected from hydrogen, fluorine, $C_{1-4}$ alkoxy, hydroxyl, or amino; $X_1$ is N or $CR_4$; $R_4$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_2$ is N or $CR_5$; $R_5$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_3$ is N or $CR_6$; and $X_4$ is $CR_6$ when dotted line (----) represents a bond; $R_6$ is selected from hydrogen, cyano, $C_{1-4}$ alkyl, $C_{1-4}$ alkylamino, $C_{1-4}$ alkoxy, $C_{1-4}$ haloalkoxy, or COOH; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-4}$ alkoxy, cyano, or hydroxyl; $R_3$ is selected from hydrogen, fluorine, $C_{1-4}$ alkoxy, hydroxyl, or amino; $X_1$ is N or $CR_4$; $R_4$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_2$ is N or $CR_5$; $R_5$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_3$ is N or $CR_6$; and $X_4$ is $CR_6$ when dotted line (----) represents a bond; $R_6$ is selected from hydrogen, cyano, $C_{1-4}$ alkyl, $C_{1-4}$ alkylamino, $C_{1-4}$ alkoxy, $C_{1-4}$ haloalkoxy, or COOH; or $X_3$ is $CH_2$ or O; and $X_4$ is $CH_2$ when dotted line (----) represents no bond; $n_1$ is 0; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-4}$ alkoxy, cyano, or hydroxyl; $R_3$ is selected from hydrogen, fluorine, $C_{1-4}$ alkoxy, hydroxyl, or amino; $X_1$ is N or $CR_4$; $R_4$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_2$ is N or $CR_5$; $R_5$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_3$ is N or $CR_6$; and $X_4$ is $CR_6$ when dotted line (----) represents a bond; $R_6$ is selected from hydrogen, cyano, $C_{1-4}$ alkyl, $C_{1-4}$ alkylamino, $C_{1-4}$ alkoxy, $C_{1-4}$ haloalkoxy, or COOH; or $X_3$ is $CH_2$ or O; and $X_4$ is $CH_2$ when dotted line (----) represents no bond; $n_1$ is 1; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-5}$ alkyl, $C_{2-5}$ alkenyl, $C_{3-5}$ cycloalkyl, $C_{1-5}$ alkylamino, $C_{1-5}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-5}$ alkyl, $C_{2-5}$ alkenyl, $C_{3-5}$ cycloalkyl, $C_{1-5}$ alkylamino, $C_{1-5}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_9$, $SO_2NHR_9$, methylsulfone, $C_{1-5}$ alkyl, $C_{1-5}$ alkoxy, $C_{1-5}$ haloalkoxy, $C_{3-5}$ cycloalkyl, $C_{3-5}$ cycloalkylamino, $C_{3-5}$ aminocycloalkyl, $C_{3-6}$ cycloalkylhydroxy, $C_{1-5}$ alkylamino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, $C_{1-3}$ alkoxy, cyano, or hydroxyl; $R_3$ is selected from hydrogen, fluorine, $C_{1-3}$ alkoxy, hydroxyl, or amino; $X_1$ is N or $CR_4$; $R_4$ is selected from hydrogen, halogen, cyano, $C_{1-3}$ alkoxy, $C_{1-3}$ haloalkyl, $C_{1-3}$ haloalkoxy, or $C_{1-3}$ alkyl; $X_2$ is N or $CR_5$; $R_5$ is selected from hydrogen, halogen, cyano, $C_{1-3}$ alkoxy, $C_{1-3}$ haloalkyl, $C_{1-3}$ haloalkoxy, or $C_{1-3}$ alkyl; $X_3$ is N or $CR_6$; and $X_4$ is $CR_6$ when dotted line (----) represents a bond; $R_6$ is selected from hydrogen, cyano, $C_{1-3}$ alkyl, $C_{1-3}$ alkylamino, $C_{1-3}$ alkoxy, $C_{1-3}$ haloalkoxy, or COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{1-4}$ haloalkyl, $C_{3-4}$ cycloalkyl, $C_{1-4}$ alkylamino, or 4-7 membered saturated carbocyclyl or heterocyclyl ring, wherein the heterocyclyl ring is optionally substituted with upto three heteroatoms independently selected from O, N or S, wherein $C_{1-4}$ alkyl, $C_{1-4}$ haloalkyl, $C_{3-4}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, O—$PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ aminocycloalkyl, $C_{3-6}$ cycloalkylhydroxy, $C_{1-4}$ alkylamino, or 3-7 membered saturated or unsaturated heterocyclyl ring optionally substituted with upto three heteroatoms independently selected from O, N or S; $R_2$ is selected from hydrogen, fluorine, chlorine, $C_{1-2}$ alkoxy, cyano, or hydroxyl; $R_3$ is selected from hydrogen, fluorine, $C_{1-2}$ alkoxy, hydroxyl, or amino; $X_1$ is N or $CR_4$; $R_4$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_2$ is N or $CR_5$; $R_5$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_3$ is N or $CR_6$; and $X_4$ is $CR_6$ when dotted line (----) represents a bond; $R_6$ is selected from hydrogen, cyano, $C_{1-2}$ alkyl, $C_{1-3}$ alkylamino, $C_{1-2}$ alkoxy, $C_{1-2}$ haloalkoxy, or COOH; or $X_3$ is $CH_2$ or O; and $X_3$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_{1-2}$ alkoxy, $C_{1-2}$ haloalkyl, $C_{1-2}$ haloalkoxy, or $C_{1-2}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{1-4}$ haloalkyl, $C_{3-4}$ cycloalkyl, $C_{1-4}$ alkylamino, or 4-6 membered saturated carbocyclyl or heterocyclyl ring, wherein the heterocyclyl ring is optionally substituted with upto three heteroatoms independently selected from O, N or S, wherein $C_{1-4}$ alkyl, $C_{1-4}$ haloalkyl, $C_{3-4}$ cycloalkyl, $C_{1-4}$ alkylamino, and 4-6 membered saturated carbocyclyl or heterocyclyl ring are optionally substituted with 1 to 3 groups independently selected from halogen, amino, hydroxyl, O—$PO_3H_2$, $C_{1-4}$ alkyl, $C_{1-4}$ alkoxy, $C_{1-4}$ haloalkoxy, $C_{3-4}$ cycloalkyl, $C_{3-5}$ cycloalkylamino, $C_{3-5}$ aminocycloalkyl, $C_{3-6}$ cycloalkylhydroxy, $C_{1-4}$ alkylamino, or 3-5 membered saturated or unsaturated heterocyclyl ring optionally substituted with upto three heteroatoms independently selected from O, N or S; $R_2$ is selected from hydrogen, fluorine, chlorine, $C_{1-2}$ alkoxy, cyano, or hydroxyl; $R_3$ is selected from hydrogen, fluorine, $C_{1-2}$ alkoxy, hydroxyl, or amino; $X_1$ is N or $CR_4$; $R_4$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_2$ is N or $CR_5$; $R_5$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_3$ is N or $CR_6$; and $X_4$ is $CR_6$ when dotted line (----) represents a bond; $R_6$ is selected from hydrogen, cyano, $C_{1-2}$ alkyl, $C_{1-3}$ alkylamino, $C_{1-2}$ alkoxy, $C_{1-2}$ haloalkoxy, or COOH; or $X_3$ is $CH_2$ or O; and $X_3$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_{1-2}$ alkoxy, $C_{1-2}$ haloalkyl, $C_{1-2}$ haloalkoxy, or $C_{1-2}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{1-4}$ haloalkyl, $C_{3-4}$ cycloalkyl, $C_{1-4}$ alkylamino, or 4-7 membered saturated carbocyclyl or heterocyclyl ring, wherein the heterocyclyl ring is optionally substituted with upto three heteroatoms independently selected from O, N or S, wherein $C_{1-4}$ alkyl, $C_{1-4}$ haloalkyl, $C_{3-4}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, O—$PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ aminocycloalkyl, $C_{3-6}$ cycloalkylhydroxy, $C_{1-4}$ alkylamino, or 3-7 membered saturated or unsaturated heterocyclyl ring optionally substituted with upto three heteroatoms independently selected from O, N or S; $R_2$ is selected from hydrogen, fluorine, chlorine, $C_1$ alkoxy, cyano, or hydroxyl; $R_3$ is selected from hydrogen, fluorine, $C_1$ alkoxy, hydroxyl, or amino; $X_1$ is N or $CR_4$; $R_4$ is selected from hydrogen, halogen, cyano, $C_1$ alkoxy, or $C_1$ alkyl; $X_2$ is N or $CR_5$; $R_5$ is selected from hydrogen, halogen, cyano, $C_1$ alkoxy, $C_1$ haloalkyl, $C_1$ haloalkoxy, or $C_1$ alkyl; $X_3$ is N or $CR_6$; and $X_4$ is $CR_6$ when dotted line (----) represents a bond; $R_6$ is selected from hydrogen, cyano, $C_{1-2}$ alkyl, $C_{1-3}$ alkylamino, $C_{1-2}$ alkoxy, $C_{1-2}$ haloalkoxy, or COOH; or $X_3$ is $CH_2$ or O; and $X_3$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_{1-2}$ alkoxy, $C_{1-2}$ haloalkyl, $C_{1-2}$ haloalkoxy, or $C_{1-2}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{1-4}$ haloalkyl, $C_{3-4}$ cycloalkyl, $C_{1-4}$ alkylamino, or 4-7 membered saturated carbocyclyl or heterocyclyl ring, wherein the heterocyclyl ring is optionally substituted with upto three heteroatoms independently selected from O, N or S, wherein $C_{1-4}$ alkyl, $C_{1-4}$ haloalkyl, $C_{3-4}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, O—$PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ aminocycloalkyl, $C_{3-6}$ cycloalkylhydroxy, $C_{1-4}$ alkylamino, or 3-7 membered saturated or unsaturated heterocyclyl ring optionally substituted with upto three heteroatoms independently selected from O, N or S; $R_2$ is selected from hydrogen, fluorine, $C_{1-2}$ alkoxy, cyano, or hydroxyl; $R_3$ is selected from hydrogen, fluorine, $C_{1-2}$ alkoxy, hydroxyl, or amino; $X_1$ is N or $CR_4$; $R_4$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_2$ is N or $CR_5$; $R_5$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_3$ is N or $CR_6$; and $X_4$ is $CR_6$ when dotted line (----) represents a bond; $R_6$ is selected from hydrogen, cyano, $C_1$ alkyl, $C_{1-3}$ alkylamino, $C_1$ alkoxy, $C_1$ haloalkoxy, or COOH; or $X_3$ is $CH_2$ or O; and $X_3$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_1$ alkoxy, or $C_1$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

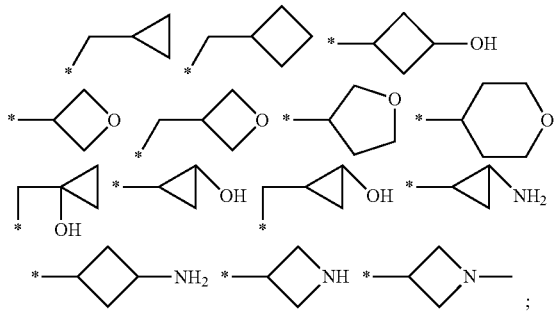

$R_2$ is selected from H, F, Cl, $OCH_3$, CN, or OH; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is selected from O, S, NH, or $CH_2$; and $R_8$ is selected from H, OH, $C_{1-6}$ alkyl, or F.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

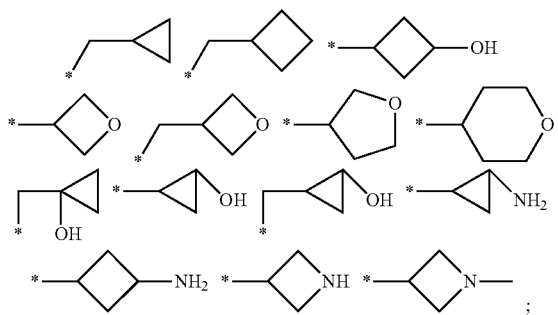

$R_2$ is selected from H, F, Cl, $OCH_3$, CN, or OH; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

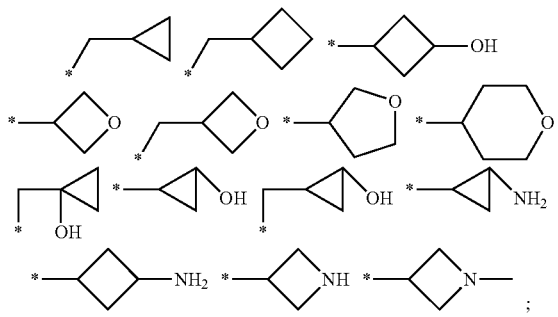

$R_2$ is selected from H, F, Cl, $OCH_3$, CN, or OH; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$ is $CR_7$; $R_7$ is H; $Y_2$ is N; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

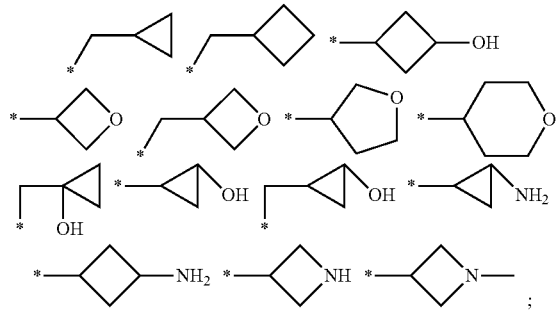

$R_2$ is selected from H, F, Cl, $OCH_3$, CN, or OH; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$ is $CR_7$; $Y_2$ is $CR_7$; $R_7$ is H; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $C_2H$, or $CH_2CH_2OH$; $R_2$ is selected from H, F, Cl, $OCH_3$, CN, or OH; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, and $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

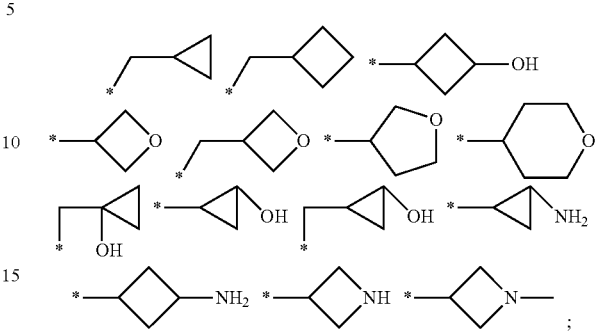

$R_2$ is selected from H, F, or $C_1$; $R_3$ is selected from H, F, $OCH_3$, OH, or $NH_2$; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

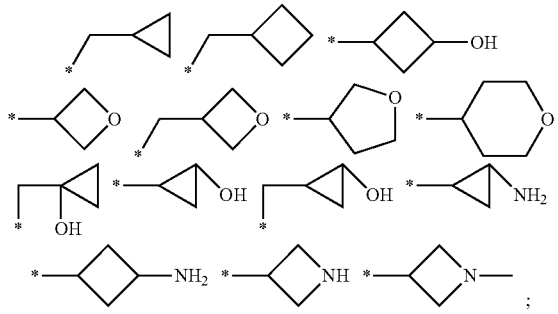

$R_2$ is selected from H, F, Cl, $OCH_3$, CN, or OH; $R_3$ is selected from H, or OH; $X_1$ is N or $CR_4$; $R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

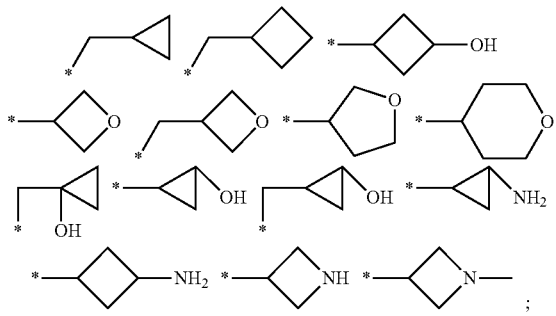

$R_2$ is selected from H, F, Cl, $OCH_3$, CN, or OH; $R_3$ is selected from H, F, $OCH_3$, OH, or $NH_2$; $X_1$ is $CR_4$; $R_4$ is H; $X_2$ is N or $CR_5$; $R_5$ is selected from H, F, CN, $OCH_3$, $CF_3$, $OCF_3$, or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

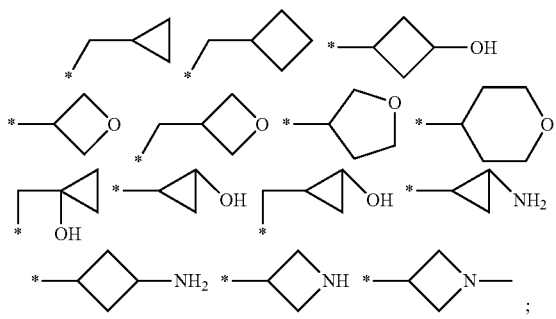

$R_2$ is selected from H, F, Cl, $OCH_3$, CN, or OH; $R_3$ is selected from H, F, $OCH_3$, OH, or $NH_2$; $X_1$ is $CR_4$; $R_4$ is H; $X_2$ is N; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

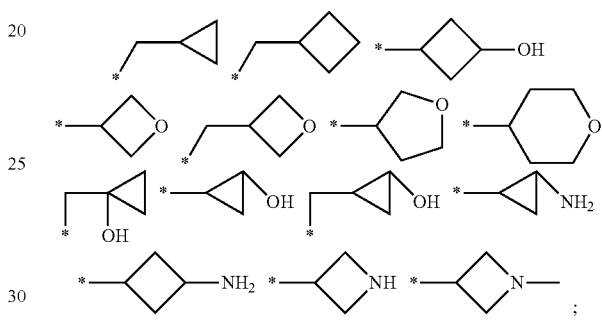

$R_2$ is selected from H, F, Cl, $OCH_3$, CN, or OH; $R_3$ is selected from H, F, $OCH_3$, OH, or $NH_2$; $X_1$ is $CR_4$; $R_4$ is H; $X_2$ is $CR_5$; $R_5$ is H or $CH_3$; $X_3$ is N or $CR_6$; and $X_4$ is $CR_6$ when dotted line (----) represents a bond; $R_6$ is selected from H, CN, COOH, $CH_2NH_2$, $CH(CH_3)NH_2$, $CH_2NHCH_3$, $OCH_3$, $OCF_3$, or $CH_3$; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from H, F, CN, $OCH_3$, or $CH_3$; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $C_2H$, or $CH_2CH_2OH$; $R_2$ is selected from H, Cl, or F; $R_3$ is selected from H, $CH_3$, and OH; $X_1$ is $CR_4$; $R_4$ is H; $X_2$ is N or $CR_5$; $R_5$ is H or $CH_3$; $X_3$ is N or $CR_6$; and $X_4$ is $CR_6$ when dotted line (----) represents a bond; $R_6$ is H or $CH_3$; or $X_3$ is $CH_2$ or 0; and $X_4$ is $CH_2$ when dotted line (----) represents no bond; $n_1$ is 0 or 1; $Y_1$ is $CR_7$; $Y_2$ is N or $CR_7$; $R_7$ is H; $Z_1$ is O or S; and $R_8$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N or S; and $R_9$ is selected from hydrogen, or $C_{1-6}$ alkyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_2$ is selected from hydrogen, fluorine, chlorine, cyano, $C_{1-6}$ alkoxy, or hydroxyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_3$ is selected from hydrogen, $C_{1-6}$ alkyl, fluorine, $C_{1-6}$ alkoxy, hydroxyl, or amino.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $X_1$ is N or $CR_4$; and $R_4$ is selected from hydrogen, halogen, cyano, $C_{1-6}$ alkoxy, $C_{1-6}$ haloalkyl, $C_{1-6}$ haloalkoxy, or $C_{1-6}$ alkyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $X_2$ is N or $CR_5$; and $R_5$ is selected from hydrogen, halogen, cyano, $C_{1-6}$ alkoxy, $C_{1-6}$ haloalkyl, $C_{1-6}$ haloalkoxy, or $C_{1-6}$ alkyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $X_3$ is N or $CR_6$; and $X_4$ is $CR_6$ when dotted line (----) represents a bond; and $R_6$ is selected from hydrogen, cyano, $C_{1-6}$ alkyl, $C_{1-6}$ alkylamino, $C_{1-6}$ alkoxy, $C_{1-6}$ haloalkoxy, or COOH; or $X_3$ is $CH_2$ or O; and $X_4$ is $CH_2$ when dotted line (----) represents no bond.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $n_1$ is 0 to 2.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $Y_1$, and $Y_2$ are independently selected from N or $CR_7$; and $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_8$ is selected from hydrogen, hydroxyl, $C_{1-6}$ alkyl, or fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, which is selected from a group consisting of:

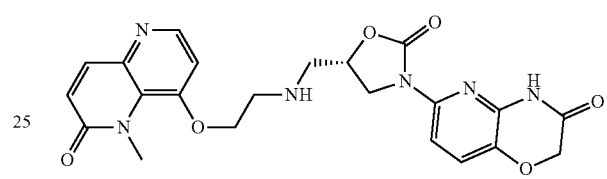

(S)-6-(5-(((2-((5-methyl-6-oxo-5,6-dihydro-1,5-naphthyridin-4-yl)oxy)ethyl)amino)methyl)-2-oxooxazolidin-3-yl)-2H-pyrido[3,2-b][1,4]oxazin-3(4H)-one (Compound 1),

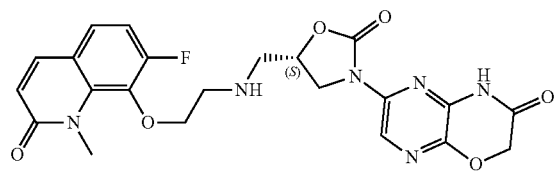

(S)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 2),

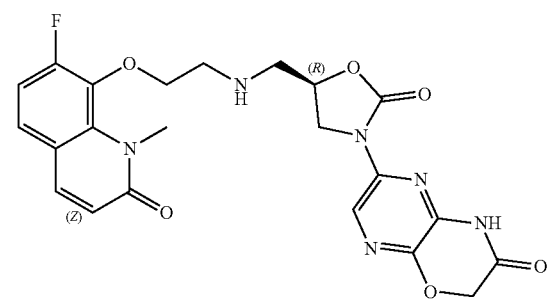

(R)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 3),

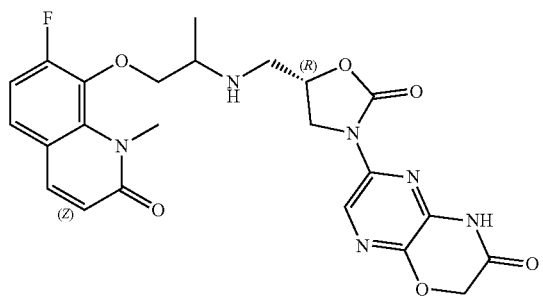

6-((5S)-5-(((1-((7-fluoro-1-methyl-2-oxo-1,2-dihydroquinolin-8-yl)oxy)propan-2-yl)amino)methyl)-2-oxooxazolidin-3-yl)-2H-pyrazino[2,3-b][1,4]oxazin-3(4H)-one (Compound 4),

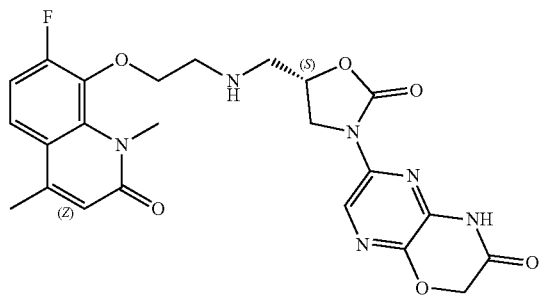

(S)-6-(5-(((2-((7-fluoro-1,4-dimethyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 5),

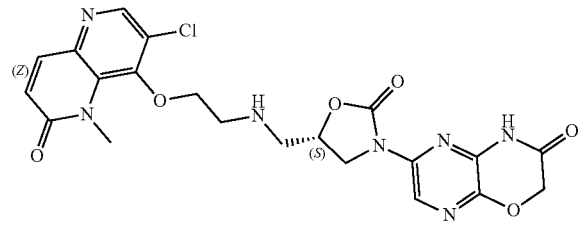

(S)-6-(5-(((2-((3-chloro-5-methyl-6-oxo-5,6-dihydro-1,5-naphthyridin-4-yl)oxy)ethyl)amino)methyl)-2-oxooxazolidin-3-yl)-2H-pyrazino[2,3-b][1,4]oxazin-3(4H)-one (Compound 6),

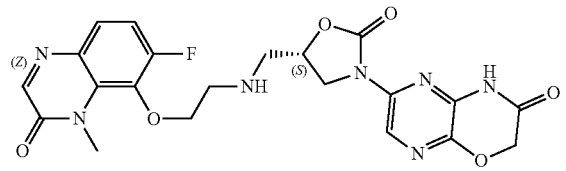

(S)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 7),

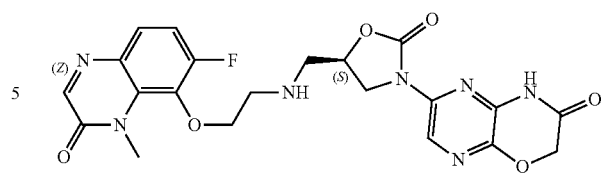

(R)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 8),

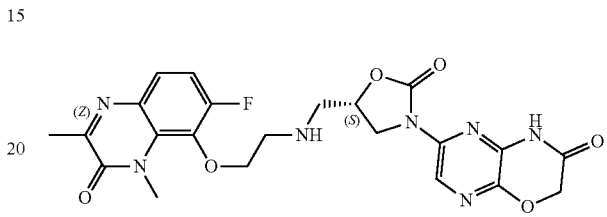

(S)-6-(5-(((2-((6-fluoro-2,4-dimethyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 9),

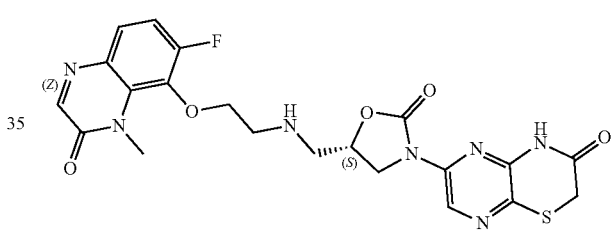

(S)-5-(((2-((6-fluoro-4-methyl-3-oxo-3,4-dihydroquinoxalin-5-yl)oxy)ethyl)amino)methyl)-3-(3-oxo-3,4-dihydro-2H-pyrazino[2,3-b][1,4]thiazin-6-yl)oxazolidin-2-one (Compound 10), According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, which is selected from a group consisting of:

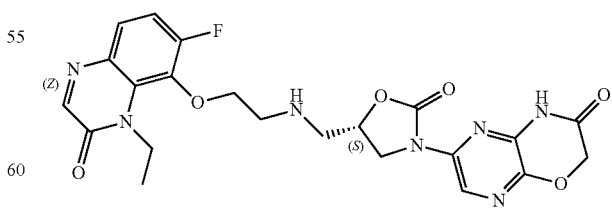

(S)-6-(5-(((2-((4-ethyl-6-fluoro-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 11),

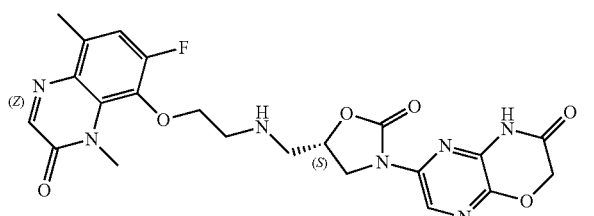

(S)-6-(5-(((2-((6-fluoro-4,8-dimethyl-3-oxo-3,4-dihydro-quinoxalin-5-yl)oxy)ethyl)amino)methyl)-2-oxooxazolidin-3-yl)-2H-pyrazino[2,3-b][1,4]oxazin-3(4H)-one (Compound 12),

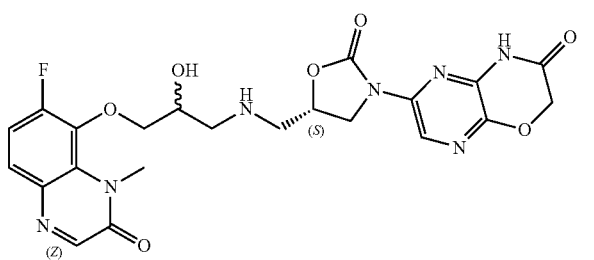

6-((5S)-5-(((3-((6-fluoro-4-methyl-3-oxo-3,4-dihydroquinoxalin-5-yl)oxy)-2-hydroxypropyl)amino)methyl)-2-oxooxazolidin-3-yl)-2H-pyrazino[2,3-b][1,4]oxazin-3(4H)-one (Compound 13),

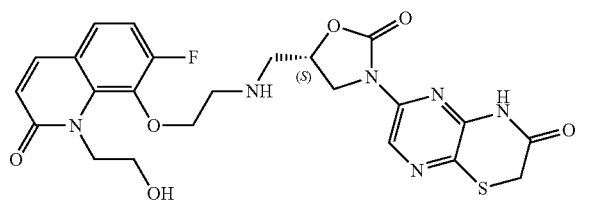

(S)-5-(((2-((7-fluoro-1-(2-hydroxyethyl)-2-oxo-1,2-dihydroquinolin-8-yl)oxy)ethyl) amino)methyl)-3-(3-oxo-3,4-dihydro-2H-pyrazino[2,3-b][1,4]thiazin-6-yl)oxazolidin-2-one (Compound 14), and

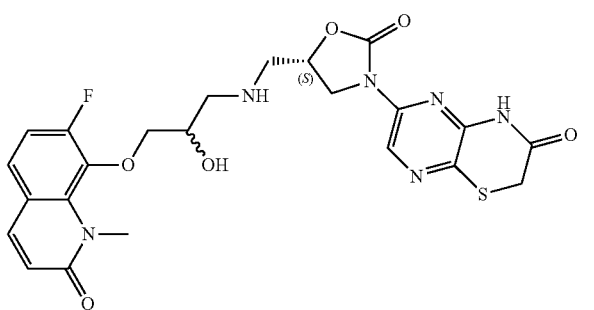

(5S)-5-(((3-((7-fluoro-1-methyl-2-oxo-1,2-dihydroquinolin-8-yl)oxy)-2-hydroxypropyl)amino) methyl)-3-(3-oxo-3,4-dihydro-2H-pyrazino[2,3-b][1,4]thiazin-6-yl)oxazolidin-2-one (Compound 15)

According to an embodiment, the present disclosure relates to a compound of Formula (B) or its stereoisomers, pharmaceutically acceptable salts, complexes, hydrates, solvates, tautomers, polymorphs, racemic mixtures, optically active forms, and pharmaceutically active derivatives thereof, wherein Formula (B)

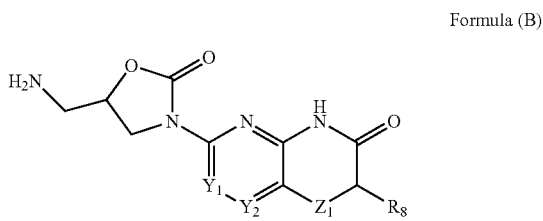

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula (B) or its stereoisomers, pharmaceutically acceptable salts, complexes, hydrates, solvates, tautomers, polymorphs, racemic mixtures, optically active forms and pharmaceutically active derivatives thereof, wherein $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

According to an embodiment, the present disclosure relates to a compound of Formula (B) or its stereoisomers, pharmaceutically acceptable salts, complexes, hydrates, solvates, tautomers, polymorphs, racemic mixtures, optically active forms and pharmaceutically active derivatives thereof, wherein $Y_1$, and $Y_2$ are independently selected from N or $CR_7$; $R_7$ is selected from hydrogen, halogen, cyano, $C_{1-4}$ alkoxy, or $C_{1-4}$ alkyl; $Z_1$ is selected from O, or S; and $R_8$ is selected from hydrogen, hydroxyl, $C_{1-4}$ alkyl, or fluorine.

According to an embodiment, the present disclosure relates to a compound of Formula (B) or its stereoisomers, pharmaceutically acceptable salts, complexes, hydrates, solvates, tautomers, polymorphs, racemic mixtures, optically active forms and pharmaceutically active derivatives thereof, which is selected from a group consisting of:

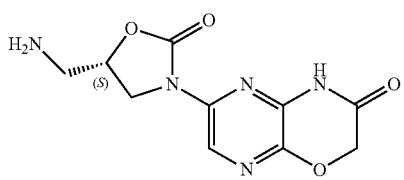

(S)-6-(5-(aminomethyl)-2-oxooxazolidin-3-yl)-2H-pyrazino[2,3-b][1,4]oxazin-3(4H)-one (Intermediate V)

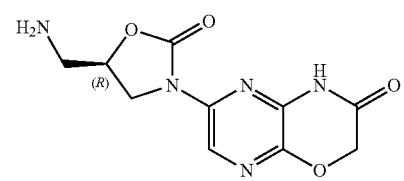

(R)-6-(5-(aminomethyl)-2-oxooxazolidin-3-yl)-2H-pyrazino[2,3-b][1,4]oxazin-3(4H)-one (Intermediate VI)

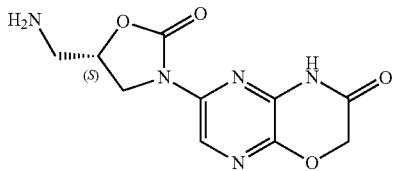

(S)-5-(aminomethyl)-3-(3-oxo-3,4-dihydro-2H-pyrazino[2,3-b][1,4]thiazin-6-yl)oxazolidin-2-one (Intermediate VII).

According to an embodiment, the present disclosure relates to a process of preparation of compounds of Formula (B), or its stereoisomers, pharmaceutically acceptable salts, complexes, hydrates, solvates, tautomers, polymorphs, racemic mixtures, optically active forms and pharmaceutically active derivatives thereof, said process comprising: (a) reacting a compound of Formula (C), and a compound of Formula (D) in the presence of at least one catalyst and at least one solvent to obtain a compound of Formula (E); (b) reacting the compound of Formula (E) and at least one nitrogen compound to obtain a compound of Formula (F); and (c) reducing the compound of Formula (F) to obtain a compound Formula (B).

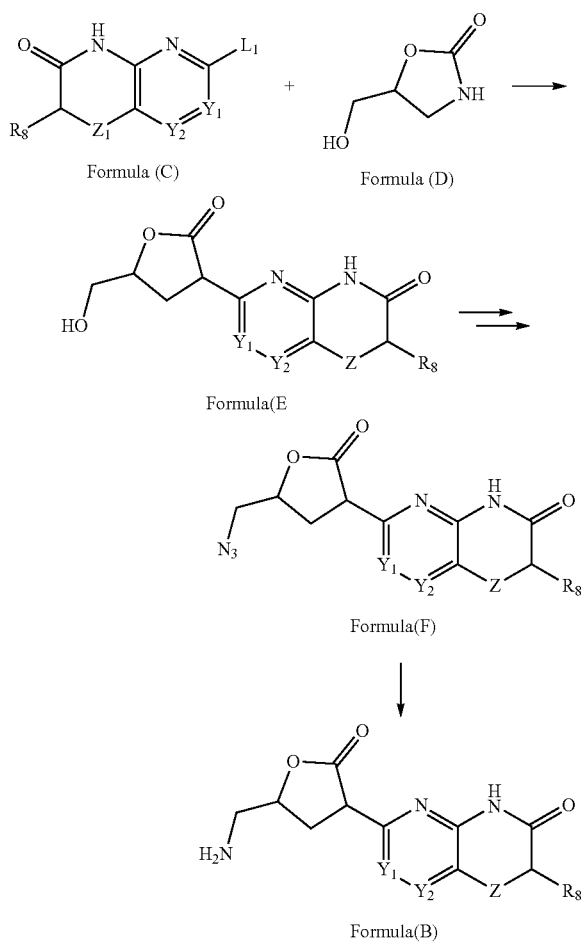

According to an embodiment, the present disclosure relates to a process of preparation of compounds of Formula (B) as described herein, wherein the at least one catalyst is selected from a group consisting of Pd containing catalyst, t-BuXPhos-Pd, Pd(OAc)$_2$, and combinations thereof, the at least one solvent is selected from the group consisting of THF, toluene, dioxane, and combinations thereof, the at least one nitrogen compound is NaN$_3$.

According to an embodiment, the present disclosure relates to a process of preparation of compounds of Formula (B) as described herein, wherein reducing the compound of Formula (F) to obtain a compound Formula (B) is carried out in the presence of reducing agent selected from triphenyl phosphine (Ph$_3$P)/THF—H$_2$O, or hydrogen and palladium carbon (H$_2$/Pd—C).

According to an embodiment, the present disclosure relates to a process of preparation of compounds of Formula I, or its stereoisomers, pharmaceutically acceptable salts, complexes, hydrates, solvates, tautomers, polymorphs, racemic mixtures, optically active forms and pharmaceutically active derivatives thereof, said process comprising reacting compounds of Formula (A) and compounds of Formula (B) in presence of at least one reducing agent and an adsorbent to obtain the compounds of Formula I, wherein R$_1$ of Formula (A) is selected from C$_{1-6}$ alkyl, C$_{2-6}$ alkenyl, C$_{3-6}$ cycloalkyl, C$_{1-6}$ alkylamino, C$_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein C$_{1-6}$ alkyl, C$_{2-6}$ alkenyl, C$_{3-6}$ cycloalkyl, C$_{1-6}$ alkylamino, C$_{1-6}$ aminoalkylene, and 4-7 membered saturated or unsaturated carbocyclyl or heterocyclyl ring are optionally substituted with 1 to 3 groups independently selected from halogen, amino, hydroxyl, SO$_3$H, O—PO$_3$H$_2$, COOR$_9$, CONHR$_9$, SO$_2$NHR$_9$, methylsulfone, C$_{1-6}$ alkyl, C$_{1-6}$ alkoxy, C$_{1-6}$ haloalkoxy, C$_{3-6}$ cycloalkyl, C$_{3-6}$ cycloalkylamino, C$_{3-6}$ aminocycloalkyl, C$_{3-6}$ cycloalkylhydroxy, C$_{1-6}$ alkylamino, or 3-7 membered saturated or unsaturated heterocyclyl ring optionally substituted with upto three heteroatoms independently selected from O, N or S; R$_9$ is selected from hydrogen, or C$_{1-6}$ alkyl; R$_2$ is selected from hydrogen, fluorine, chlorine, cyano, C$_{1-6}$ alkoxy, or hydroxyl; R$_3$ is selected from hydrogen, C$_1$ alkyl, fluorine, C$_{1-6}$ alkoxy, hydroxyl, or amino; X$_1$ is N or CR$_4$; R$_4$ is selected from hydrogen, halogen, cyano, C$_{1-6}$ alkoxy, C$_{1-6}$ haloalkyl, C$_{1-6}$ haloalkoxy, or C$_{1-6}$ alkyl; X$_2$ is N or CR$_5$; R$_5$ is selected from hydrogen, halogen, cyano, C$_{1-6}$ alkoxy, C$_{1-6}$ haloalkyl, C$_{1-6}$ haloalkoxy, or C$_1$ alkyl; X$_3$ is N or CR$_6$; and X$_4$ is CR$_6$ or C$_{1-6}$ alkyl when dotted line (----) represents a bond; R$_6$ is selected from hydrogen, cyano, C$_{1-6}$ alkyl, C$_{1-6}$ alkylamino, C$_{1-6}$ alkoxy, C$_{1-6}$ haloalkoxy, or COOH; or X$_3$ is CH$_2$ or O; and X$_4$ is CH$_2$ when dotted line (----) represents no bond; and n$_1$ is 0 to 2; R$_8$ of Formula (B) is selected from hydrogen, hydroxyl, C$_{1-6}$ alkyl, or fluorine; Y$_1$, and Y$_2$ are independently selected from N or CR$_7$; R$_7$ is selected from hydrogen, halogen, cyano, C$_{1-6}$ alkoxy, C$_{1-6}$ haloalkyl, C$_{1-6}$ haloalkoxy, or C$_{1-6}$ alkyl; Z$_1$ is selected from O, S, NH, or CH$_2$; and R$_1$ of Formula I is selected from C$_{1-6}$ alkyl, C$_{2-6}$ alkenyl, C$_{3-6}$ cycloalkyl, C$_{1-6}$ alkylamino, C$_{1-6}$ aminoalkylene, or 4-7 membered saturated or unsaturated, carbocyclyl or heterocyclyl ring, wherein the heterocyclyl ring is optionally substituted with upto three heteroatoms independently selected from O, N or S, wherein C$_{1-6}$ alkyl, C$_{2-6}$ alkenyl, C$_{3-6}$ cycloalkyl, C$_{1-6}$ alkylamino, C$_{1-6}$ aminoalkylene, and 4-7 membered saturated or unsaturated carbocyclyl or heterocyclyl ring are optionally substituted with 1 to 3 groups independently selected from halogen, amino, hydroxyl, SO₃H, O—PO₃H₂, COOR₉, CONHR₉, SO₂NHR₉, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, di($C_{1-6}$ alkyl)amino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-6}$ alkoxy, or hydroxyl; $R_3$ is selected from hydrogen, $C_{1-6}$ alkyl, fluorine, $C_{1-6}$ alkoxy, hydroxyl, or amino; $X_1$ is N or $CR_4$; $R_4$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_3$ is N or $CR_6$; and $X_4$ is $CR_6$ when dotted line (----) represents a bond; $R_6$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; and $R_8$ is selected from hydrogen, hydroxyl, $C_{1-6}$ alkyl, or fluorine.

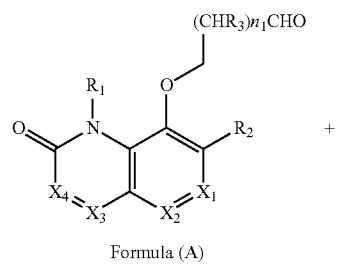

Formula (A)

+

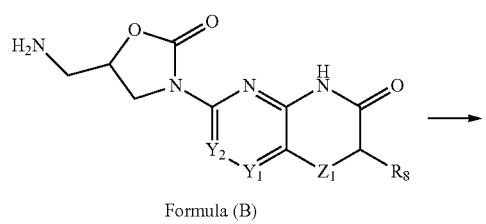

Formula (B)

⟶

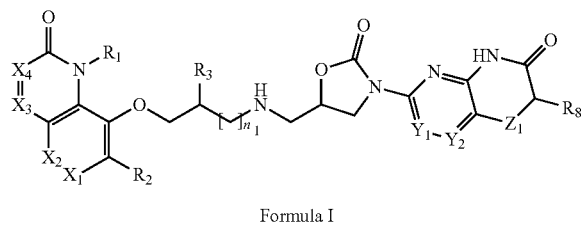

Formula I

According to an embodiment, the present disclosure relates to a process of preparation of compounds of Formula I as described herein, wherein said process comprises a compound of Formula (A)

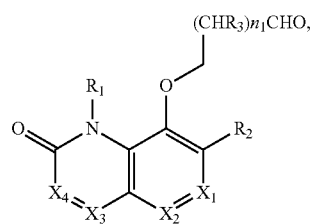

Formula (A)

$R_1$ of Formula (A) is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, SO₃H, O—PO₃H₂, COOR₉, CONHR₉, SO₂NHR₉, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, di($C_{1-6}$ alkyl) amino, or 3-7 membered saturated or unsaturated heterocyclyl ring optionally substituted with upto three heteroatoms independently selected from O, N or S; $R_9$ is selected from hydrogen, or $C_{1-6}$ alkyl; $R_2$ is selected from hydrogen, fluorine, chlorine, cyano, $C_{1-6}$ alkoxy, and hydroxyl; $R_3$ is selected from hydrogen, $C_{1-6}$ alkyl, fluorine, $C_{1-6}$ alkoxy, hydroxyl, or amino; $X_1$ is N or $CR_4$; $R_4$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, halogen, cyano, $C_{1-6}$ alkoxy, $C_{1-6}$ haloalkyl, $C_{1-6}$ haloalkoxy, or $C_{1-6}$ alkyl; $X_3$ is N or $CR_6$; and $X_4$ is $CR_6$ when dotted line (----) represents a bond; $R_6$ is selected from hydrogen, cyano, $C_{1-6}$ alkyl, $C_{1-6}$ alkylamino, $C_{1-6}$ alkoxy, $C_{1-6}$ haloalkoxy, or COOH; or $X_3$ is $CH_2$ or O; and $X_4$ is $CH_2$ when dotted line (----) represents no bond; and $n_1$ is 0 to 2.

According to an embodiment, the present disclosure relates to a process of preparation of compounds of Formula I as described herein, wherein said process comprises a compound of Formula (B)

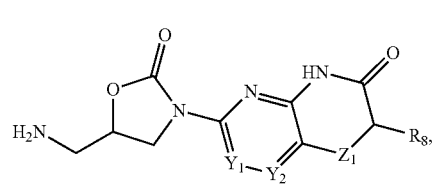

Formula (B)

wherein $R_8$ of Formula (B) is selected from hydrogen, hydroxyl, $C_{1-6}$ alkyl, or fluorine; $Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$.

According to an embodiment, the present disclosure relates to a process of preparation of compounds of Formula I as described herein, wherein the at least one reducing agent is selected from the group consisting of sodium borohydride, sodium cyano borohydride, sodium triacetoxy borohydride, and combinations thereof.

According to an embodiment, the present disclosure relates to a process of preparation of compounds of Formula I as described herein, wherein the adsorbent is selected from the group consisting of molecular sieves, silica gel, zeolites, anhydrous sodium sulphate, anhydrous magnesium sulphate, activated charcoal, and combinations thereof.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use as a medicament.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in the preparation of medicaments for inhibiting microbial growth.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in killing or inhibiting the growth of a microorganism selected from the group consisting of Gram-positive and Gram-negative bacteria.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in killing or inhibiting the growth of Gram-positive and Gram-negative bacteria.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in treatment of a bacterial infection caused by a Gram-positive bacterium or a Gram-negative bacterium.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in treating a disease or condition in a patient wherein said disease or condition is caused by a microorganism selected from the group consisting of Gram-positive, and Gram-negative pathogens.

According to an embodiment, the present disclosure relates to a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, for use in treating a disease or condition in a patient wherein said disease or condition is caused by a microorganism selected from the group consisting of Gram-positive, and Gram-negative pathogens. The patient is typically a mammal, preferably a human.

According to an embodiment, the present disclosure relates to a method of treating a disease or condition in a patient, said method comprising administering to a patient a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, wherein said disease or condition is caused by a microorganism selected from the group consisting of Gram-positive, and Gram-negative pathogens.

According to an embodiment, the present disclosure relates to medicaments that include a compound of Formula I, or Formula (B), or an addition salt of the compound of Formula I or Formula (B), with a pharmaceutically acceptable acid or base. These medicaments find their use in therapeutics, especially in the treatment of bacterial infection caused by both drug sensitive and drug resistance bacterium including quinolone resistance belonging to Gram positive and Gram-negative species; especially of those caused by *Escherichia coli, Pseudomonas aurigenosa, Klebsiella pneumoniae, Acinetobacter baumannii, Enterobacter cloacae, Staphylococcus aureus, Enterococcus faecalis Enterococcus faecium, Legionella pneumophila. Mycoplasma pneumonia, Acinetobacter haemolyticus, Acinetobacter junii, Acinetobacter lwoffi, Burkholderia cepacia, Chlamydophila pneumoniae, Clostridium difficili, Enterobacter aerogenes, Enterobacter cloacae, Moraxella catarrhalis, Neisseria gonorrhoeae, Neisseria meningitides, Proteus mirabilis, Proteus houseri, Citrobacter freundii, Citrobacter kosari, Citrobacter barakii, Seratia marcescens, Klebsiella oxytoca, Morganella morganii, Helicobacter pyroli, Mycobacterium tuberculosis*.

According to an embodiment, the present disclosure relates to the use of a compound of Formula I, or Formula (B), or its stereoisomers, pharmaceutically acceptable salts, complexes, hydrates, solvates, tautomers, polymorphs, racemic mixtures, optically active forms, and pharmaceutically active derivative thereof, in the manufacture of a medicament for the treatment of an infection caused by bacterial species in a warm-blooded animal, wherein the warm-blooded animal is man.

According to an embodiment, the present disclosure relates to the use of a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal, wherein the warm-blooded animal is man.

According to an embodiment, the present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier.

According to an embodiment, the present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier, and in combination with at least one antibiotic.

According to an embodiment, the present disclosure relates to use of a compound of Formula I, or Formula (B), or its stereoisomers, pharmaceutically acceptable salts, complexes, hydrates, solvates, tautomers, polymorphs, racemic mixtures, optically active forms and pharmaceutically active derivatives thereof, in killing or inhibiting the growth of a microorganism selected from the group consisting of bacteria, virus, fungi, and protozoa.

According to an embodiment, the present disclosure relates to a method for treating a bacterial infection caused by bacterial species in a warm-blooded animal such as man, said method including administering to said animal an effective amount of a compound of Formula I, or Formula (B), or a pharmaceutically acceptable salt thereof.

According to an embodiment, the present disclosure relates to a method for producing an antibacterial effect in a warm-blooded animal such as man, said method including administering to said animal an effective amount of a compound of Formula I, or Formula (B), or a pharmaceutically acceptable salt thereof.

According to an embodiment, the present disclosure relates to a compound of Formula I, or a pharmaceutically acceptable salt thereof, for use in the treatment and/or prophylaxis of bacterial infections in a warm-blooded animal, wherein the warm-blooded animal is man.

According to an embodiment, the present disclosure relates to a compound of Formula I, or Formula (B), or a pharmaceutically acceptable salt thereof, for the therapeutic and prophylactic treatment of mammals including humans, in particular in treating bacterial infections caused by bacterial species, is normally formulated in accordance with standard pharmaceutical practice as a pharmaceutical composition.

According to an embodiment, the present disclosure relates to a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, and at least one pharmaceutically acceptable carrier, diluent, or excipient.

According to an embodiment, the present disclosure relates to the use of a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment of a bacterial infection caused by bacterial species in a warm-blooded animal, wherein the warm-blooded animal is man.

According to an embodiment, the present disclosure relates to the use of a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal, wherein the warm-blooded animal is man.

According to an embodiment, the present disclosure relates to a method for treatment of bacterial infection in a subject, said method including administering to said subject an effective amount of a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a compound of Formula I, or Formula (B), as described herein, wherein the bacterial infection is caused by a Gram-positive or a Gram-negative pathogen.

According to an embodiment, the present disclosure relates to a compound of Formula I, or Formula (B), as described herein, wherein the bacterial infection is caused by *Escherichia coli, Pseudomonas aurigenosa, Klebsiella pneumoniae, Acinetobacter baumannii, Enterobacter cloacae, Staphylococcus aureus, Enterococcus faecalis Enterococcus faecium, Legionella pneumophila. Mycoplasma pneumonia, Acinetobacter haemolyticus, Acinetobacter junii, Acinetobacter lwoffi, Burkholderia cepacia, Chlamydophila pneumoniae, Clostridium difficili, Enterobacter aerogenes, Enterobacter cloacae, Moraxella catarrhalis, Neisseria gonorrhoeae, Neisseria meningitides, Proteus mirabilis, Proteus houseri, Citrobacter freundii, Citrobacter kosari, Citrobacter barakii, Serratia marcescens, Klebsiella oxytoca, Morganella morganii, Helicobacter pyroli, Mycobacterium tuberculosis.*

According to an embodiment, the present disclosure relates to a method for treating infection caused by bacterial species in a warm-blooded animal, wherein the warm-blooded animal is man, said method including administering to said animal an effective amount of a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a method for producing an antibacterial effect in a warm-blooded animal such as man, said method including administering to said animal an effective amount of a pharmaceutical composition including a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

According to an embodiment, the present disclosure relates to a pharmaceutical composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, and a pharmaceutically acceptable diluent or carrier.

According to an embodiment, the present disclosure relates to a composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, and a carrier.

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula I or Formula (B) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The present disclosure relates to a process of preparation of a composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a process of preparation of pharmaceutical composition comprising a compound of Formula I, or Formula (B), or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The compositions of the present disclosure may be obtained by conventional procedures using conventional pharmaceutical excipients well known in the art. Thus, compositions intended for oral use may contain, for example, one or more colouring, sweetening, flavouring and/or preservative agents Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents or procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as *arachis* oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant, wherein the anti-oxidant comprises ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the disclosure may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penetrate the cells of interest or stratum corneum, and fuse with the cell membrane, resulting in delivery of the contents of the liposome into the cell. Other suitable formulations can employ niosomes. Niosomes are lipid vesicles similar to liposomes, with membrane consisting largely of nonionic lipids, some forms of which are effective for transporting compounds across the stratum corneum.

Compositions for administration may also be formulated as a depot preparation, which may be administered by implantation or by intramuscular injection. The compositions may be formulated with suitable polymeric or hydrophobic material (as an emulsion in acceptable oil), ion exchange resins, or sparingly soluble derivatives.

The compound of the present disclosure can also be administered in sustained release forms or from sustained release drug delivery systems.

For further information on formulation, drug delivery as well as processing techniques the reader is referred to Remington's Pharmaceutical Sciences (21$^{st}$ Edition, 2005, University of the sciences in Philadelphia, Lippincott William & Wilkins)

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990 and Remington's Pharmaceutical Sciences (21$^{st}$ Edition, 2005, University of the sciences in Philadelphia, Lippincott William & Wilkins).

As stated above the size of the dose required for the therapeutic or prophylactic treatment of a particular disease state will necessarily be varied depending on the host treated, the route of administration and the severity of the illness being treated. Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the disclosure described herein also apply.

The compounds disclosed herein may be applied as a sole therapy or may involve, in addition to a compound of the disclosure, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following: i) other antibacterial agents for example macrolides e.g. erythromycin, azithromycin or clarithromycin; quinolones e.g. ciprofloxacin or levofloxacin; B lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability increasing protein (BPI) products; and/or iv) one or more antibacterial agents useful in the treatment of *Mycobacterium tuberculosis* such as one or more of rifampicin, isoniazid, pyrizinamide, ethambutol, quinolones e.g. moxifloxacin or gatifloxacin, streptomycin and/or v) efflux pump inhibitors.

According to an embodiment, the present disclosure relates to a compound of the Formula I, or Formula (B), or a pharmaceutically acceptable salt thereof and a chemotherapeutic agent selected from: i) one or more additional antibacterial agents; and/or ii) one or more anti-infective agents; and/or iii) biological protein therapeutics for example antibodies, cytokines, bactericidal/permeability increasing protein (BPI) products; iv) one or more antibacterial agents useful in the treatment of pulmonary tuberculosis, extra-pulmonary tuberculosis, *avium* infections, buruli ulcers and/or v) one or more efflux pump inhibitors.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature or could be made from commercially available compounds using adaptations of processes reported in the scientific literature. The reader is further referred to Advanced Organic Chemistry, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, published by John Wiley and Sons, 1991) and as described hereinabove.

EXAMPLES

Abbreviations

APCI—atmospheric pressure chemical ionization;
ATP—adenosine triphosphate;
BSA—bovine serum albumin;
$CDCl_3$—deuterated chloroform;
CLSI—Clinical and Laboratory Standards Institute;
DCM—dichloromethane;
DMAP—4-dimethylaminopyridine;
DMF—dimethylformamide;
DMSO—dimethylsulfoxide;
DTT—dithiothretol;
EtOAc—ethyl acetate;
EDTA—ethylenediamine tetra acetic acid;
HPLC—high pressure liquid chromatography;
LC/MS—liquid chromatography/mass spectrometry;
MPLC—medium pressure liquid chromatography;
MeOD—deuterated methanol, i.e. $D_3COD$;
MeOH— methanol;
MS—mass spectroscopy; ESP (or ES)—electrospray; EI—electron impact;
MTBD—N-methyl-1,5,7-triazabicyclo[4.4.0]dec-5-ene;
NMR—nuclear magnetic resonance spectroscopy;
OD—optical density;
SDS—sodiumdodecylsulphate;
STEB—sucrose tris EDTA buffer;
TAE—tris acetic acid EDTA buffer;
THF—tetrahydrofuran;
TFA—trifluoroacetic acid;
h—hour(s);
min—minute(s);
d—day(s);
v/v—ratio of volume/volume;
Boc—t-butoxycarbonyl;
Cbz—benzyloxycarbonyl;
Bz—benzoyl;
TLC—thin layer chromatography;
atm—atmospheric pressure;
rt—room temperature;
mg—milligram;
ng—nanogram;
g—gram;
μL—microliter;
mL—milliliter;
L—liter;
μM—micromolar;
mM—millimolar;
nm—nanometer.

GENERAL CONSIDERATIONS

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature or could be made from commercially available compounds using adaptations of processes reported in the scientific literature. The reader is further referred to *Advanced Organic Chemistry*, $5^{th}$ Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, 1991) and as described hereinabove.

The following examples provide the details about the synthesis, activities and applications of the compounds of the present disclosure. It should be understood the following is representative only, and that the invention is not limited by the details set forth in these examples.

Material and Methods

Evaporations were carried out by rotary evaporation in vacuo and work up procedures were carried out after removal of residual solids by filtration; temperatures are quoted as ° C.; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kiesel gel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the invention was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (* scale) and peak multiplicities are shown thus: s, singlet; d, doublet; dd, doublet of doublets; dt, doublet of triplets; dm, doublet of multiplets; t, triplet, m, multiplet; br, broad. Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

Example 1

General Procedure for Synthesis of Compounds of Formula I

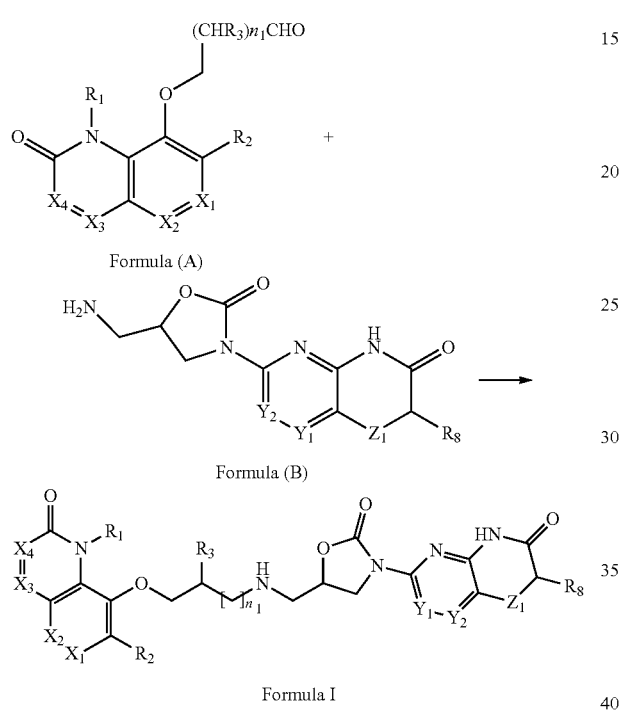

The present invention provides a process for preparing compounds of Formula I, and pharmaceutically acceptable salts thereof; the process involves reacting a compound of Formula (A) and an amine derivative of Formula (B) under reductive amination conditions, wherein $n_1=0$ or 1; $R_8$ is H.

General Procedure to Prepare the Compounds of Formula (A)

Palladium catalysed hydroxylation of halo arenes such as Formula (D) was carried out to obtain the compounds of Formula (C). Further the compounds of Formula (C) were treated with haloalkyl acetal reagent (e.g $BrCH_2(CH_2)n_1CH(OCH_2CH_3)_2$) to obtain the compounds of Formula (A).

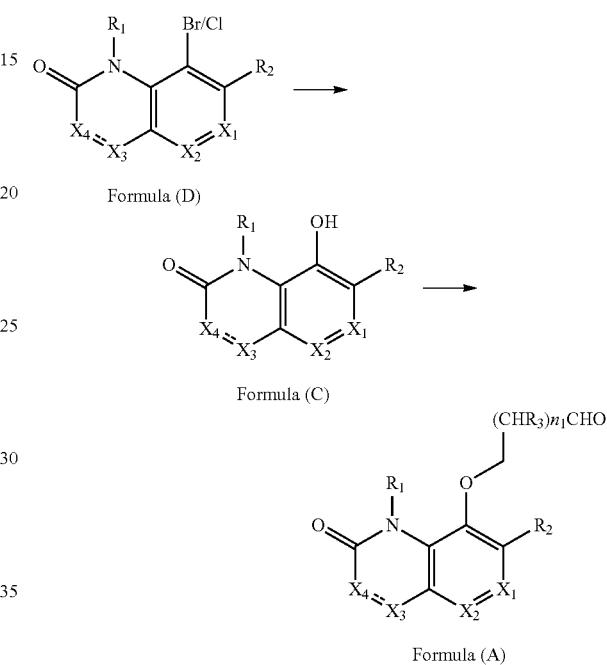

The compounds of Formula Ia and Formula Ib where in $Z_1$ is O; $n_1=0$; $R_3$ is H or OH; and $R_8$ is H; can be prepared by reacting compounds of Formula (E) with compounds of Formula (G) or (F) as shown Scheme 1.

Scheme 1

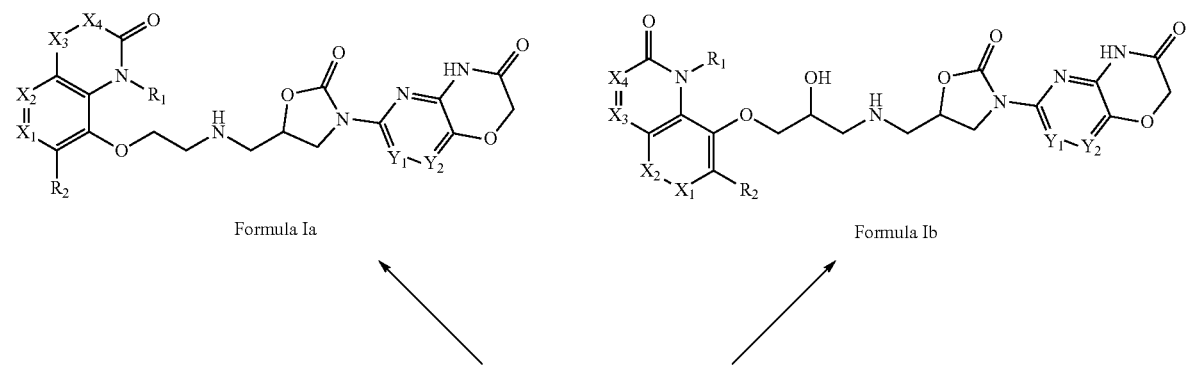

Formula Ia
Formula Ib

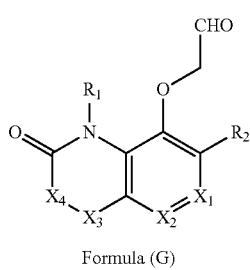

Formula (G)

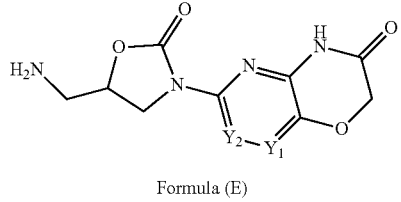

Formula (E)

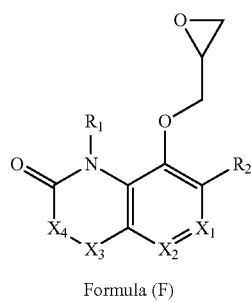

Formula (F)

Compounds of Formula (E) may be prepared from compounds of Formula (H) and compounds of Formula I as summarised in Scheme 2. Palladium catalysed Buchwald coupling of compounds of Formula (H) with Formula (I) under optimal reaction conditions provided the compounds of Formula (J). Further compounds of Formula (J) was converted to compounds of Formula (K) via azidation reaction and reduction of azide functionality provided the compounds Formula (E).

Example 2

Synthesis of Intermediates

Synthesis of 2-((5-methyl-6-oxo-5,6-dihydro-1,5-naphthyridin-4-yl)oxy)acetaldehyde (Intermediate I)

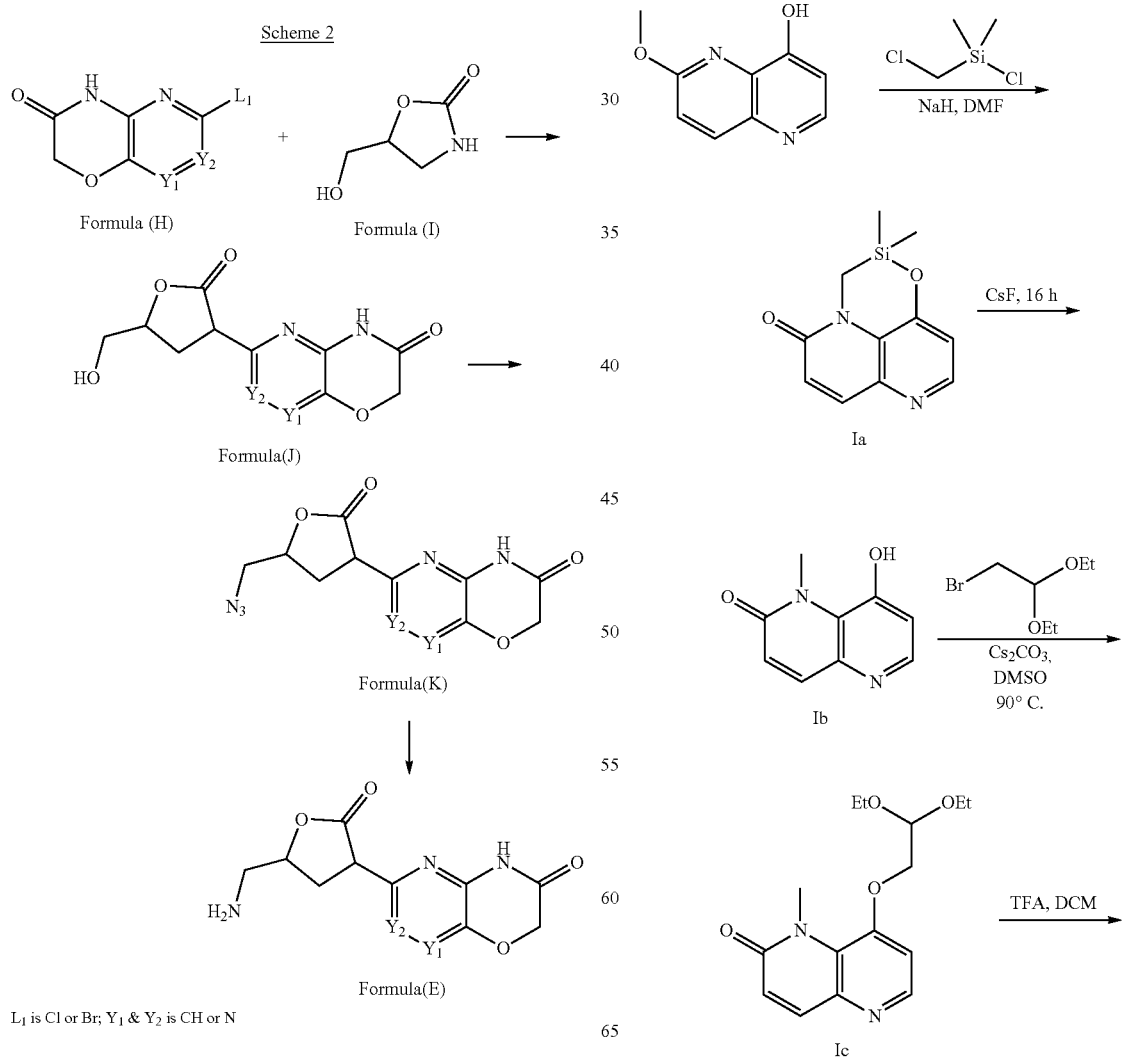

51

-continued

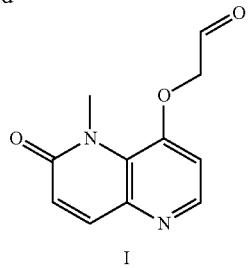

I

Step 1: Synthesis of 2,2-dimethyl-2,3-dihydro-5H-[1,4,2]oxazasilino[6,5,4-de][1,5]naphthyridin-5-one (Ia)

To a stirred suspension of NaH (0.34 g, 8.5 mmol) in dry DMF was added 6-Methoxy-1,5-naphthyridin-4-ol (Combi-Blocks, 1 g, 5.6 mmol) in portion wise at 0° C. The reaction mixture was allowed stir at rt for 1 h. To this was added chloro (chloromethyl) dimethyl silane (1.29 g, 9.09 mmol) at room temperature and the reaction mixture was heated to 100° C. for 16 h. The reaction mixture was concentrated, and the crude product was co-evaporated with toluene to get the crude product Ia (0.5 gm) as off white solid and the material was used as such for next step without further purification. LC-MS Calc. for $C_{11}H_{12}N_2O_2Si$: 232.31; Obs.: 233.1[$M^+$+H].

Step 2: Synthesis of 8-hydroxy-1-methyl-1,5-naphthyridin-2(1H)-one (Ib)

To a stirred solution of Ia (0.5 g, 2.15 mmol) in dry dioxane and MeOH (2:1, 16 mL) was added CsF (0.98 g, 6.46 mmol) and the resulting mixture was heated to 80° C. for 12 h. The reaction mixture was cooled to rt and solvent was evaporated the residue was neutralised with 1.5 N HCl. The organic product was extracted with EtOAc:MeOH (9:1, 50 mL) and washed with brine solution (20 mL). The organic layer was dried over $Na_2SO_4$ and concentrated to get the crude product Ib (0.3 gm) as off-white solid. The crude was used as such for the next step without further purification. LC-MS Calc. for $C_9H_8N_2O_2$: 176.18; Obs.: 177.1 [$M^+$+H]; $^1$H NMR (400 MHz, DMSO-$D_6$): δ 7.95-7.90 (m, 2H), 6.91 (d, J=9.6 Hz, 1H), 6.59 (s, 1H), 3.96 (s, 3H), 3.12 (s, 1H).

Step 3: Synthesis of 8-(2, 2-diethoxyethoxy)-1-methyl-1,5-naphthyridin-2(1H)-one (Ic)

To a stirred solution of Ib (0.3 g, 17.04 mmol) in dry DMSO (6 mL) was added $Cs_2CO_3$ (0.66 g, 2.04 mmol) followed by the addition of bromoacetaldehyde diethylacetal (0.47 g, 2.38 mmol). The resulting mixture was heated to 90° C. for 16 h. The reaction mixture was diluted with EtOAc (50 mL) and washed with water (2×50 mL). The organic layer was dried over $Na_2SO_4$ and concentrated to get the crude product. The crude was purified by column chromatography on silica gel (60-120 mesh, 30% EtOAc in Pet. ether) to afford Ic as yellow viscous liquid (0.2 gm). LC-MS Calc. for $C_{15}H_{20}N_2O_4$: 292.34; Obs.: 293.2 [$M^+$+H].

Step 4: Synthesis of 2-((5-methyl-6-oxo-5,6-dihydro-1,5-naphthyridin-4-yl)oxy)acetaldehyde (I)

A solution of Ic (0.2 g, 0.68 mmol) in dichloromethane (3 mL), was cooled to 0° C., was added trifluoroacetic acid (1

52 mL). The reaction mixture was allowed to stir at rt for 30 min. The reaction mixture was concentrated, and the residue was diluted DCM (5 mL) and neutralized by using 10% $NaHCO_3$ solution. The organic layer was separated, dried over sodium sulphate and concentrated to get the crude product I (0.1 gm). The crude material used was used for the synthesis of Compound 1 without further purification. LC-MS Calc. for $C_{11}H_{10}N_2O_3$: 218.21; Obs.: 219.1 [$M^+$+H].

Synthesis of 2-((7-fluoro-1-methyl-2-oxo-1,2-dihydroquinolin-8-yl)oxy)acetaldehyde (Intermediate II)

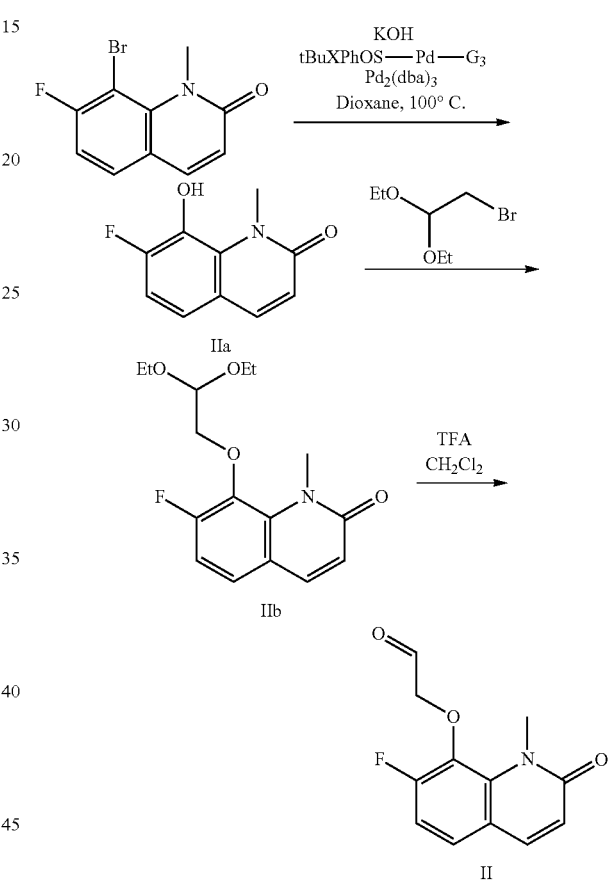

Step 1: Synthesis of 7-fluoro-8-hydroxy-1-methylquinolin-2(1H)-one (IIa)

To a mixture of 8-bromo-7-fluoro-1-methylquinolin-2 (1H)-one (CAS: 1002108-91-9, 1 g, 3.9 mmol) in 1, 4-dioxane (20 mL) was purged N2 for 10 min. To this was added $Pd_2$ (dba) 3 (0.071 g, 0.078 mmol) and t-Butylxphos-Pd-G3 (0.123 g, 0.156 mmol). After 5 minutes under degasification KOH (0.43 g, 7.8 mmol) dissolved in $H_2O$ (5 mL) was added in to the reaction mixture. The resultant mixture stirred at 100° C. for 2 hours. The reaction mixture was cooled and acidified with 1.5N dilute HCl and extracted with ethyl acetate (4×125 mL). The organic layer was washed with brine (2×100 mL), dried over $Na_2SO_4$ and concentrated under reduced pressure. The crude was triturated with petroleum ether to afford pure compound IIa (0.5 gm). LC-MS Calc. for $C_{10}H_8FNO_2$: 193.18; Obs.: 194.2, [$M^+$+H]; $^1$H NMR (400 MHz, DMSO-D₆): δ 10.02 (s, 1H), 7.79 (d, J=9.30 Hz, 1H), 7.11-7.14 (m, 2H), 6.52 (d, J=9.30 Hz, 1H), 3.89 (s, 3H).

Step 2: Synthesis of 8-(2, 2-diethoxyethoxy)-7-fluoro-1-methylquinolin-2(1H)-one (Ib)

To a mixture of IIa (0.5 g, 2.59 mmol) in DMSO (20 mL) was added Cs₂CO₃ (2.52 g, 7.77 mmol) and Bromo acetaldehyde diethylacetal (0.765 g, 3.88 mmol). The resultant mixture stirred at 90° C. for 12 hours. The reaction mixture was cooled and quenched with water extracted with ethyl acetate (4×125 mL). The organic layer was washed with brine (2×100 mL), dried over Na₂SO₄ and concentrated under reduced pressure. The crude was purified by column chromatography using silica gel (230-400 mesh) eluting with 10-15% of ethyl acetate in petroleum ether to afford pure compound IIb (0.5 gm). LC-MS Calc. for C₁₆H₂₀FNO₄: 309.34; Obs.: 310.1, [M⁺+H].

Step 3: Synthesis of 2-((7-fluoro-1-methyl-2-oxo-1,2-dihydroquinolin-8-yl)oxy)acetaldehyde (II)

To a mixture of IIb (0.3 g, 0.96 mmol) in (DCM 3 mL) was cooled to 0° C. was added TFA (4 mL). The reaction mixture was stirred at room temperature for 2 h. Reaction mixture cooled and quenched with 10% sodium bicarbonate solution extracted with DCM. The organic layer was washed with brine (2×100 mL), dried over Na₂SO₄ and concentrated under reduced pressure. The crude was triturated with petroleum ether to afford crude II (0.2 gm) and as such used for next step without further purification. 1H NMR (400 MHz, CDCl₃): δ 9.93 (s, 1H), 7.58 (d, J=9.52 Hz, 1H), 7.27-7.28 (m, 1H), 6.68 (d, J=9.40 Hz, 1H), 4.66 (s, 1H), 3.98 (s, 3H).

Synthesis of 6-bromo-2H-pyrido[3, 2-b][1,4]oxazin-3(4H)-one (Intermediate III)

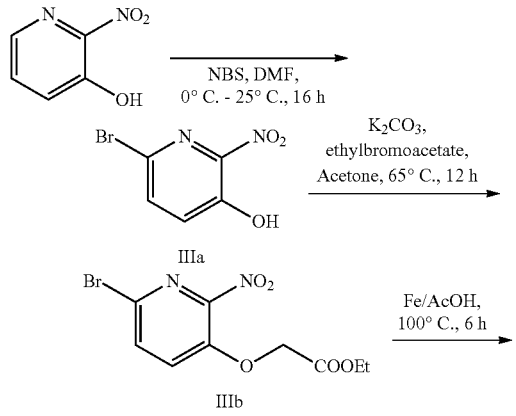

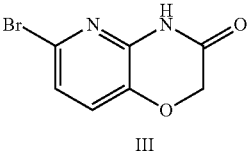

Step 1: Synthesis of 6-bromo-2-nitropyridin-3-ol (IIa)

To a solution of 2-nitropyridin-3-ol (20 g, 0.142 mol) in DMF (400 ml), N-bromosuccinimide (32.52 g, 0.187 mol) was added portion wise over a period of 5 hours at 0° C. The reaction mixture was stirred for room temperature for 12 h. After completion of the reaction, the reaction mixture was concentrated in vacuo. The residue was taken up in the ether and the mixture was stirred for 30 min. The precipitate was removed by filtration and the filtrate was concentrated in vacuo to get 6-bromo-2-nitropyridin-3-ol, IIa (40 g, 46%) as a mixture of mono and di bromo compound. The crude LCMS showed 46% of expected mono-bromo compound, this material was used as such for next step without further purification. LC-MS Calc. for C₅H₃BrN₂O₃: 218.99; Obs.: 219.2.

Step 2: Synthesis of ethyl 2-((6-bromo-2-nitropyridin-3-yl)oxy)acetate (IIIb)

To solution of 6-bromo-2-nitropyridin-3-ol, IIIa (40 g, 0.182 mol) in acetone (400 ml), cooled to 0° C., potassium carbonate (50.41 g, 0.365 mol), was added and stirred for 5 min. Then, ethyl bromoacetate (39.7 g, 0.237 mol) was added slowly and refluxed at 65° C. for 12 h. After completion of the reaction, it was filtered, and the filtrate was concentrated in vacuo. The crude was diluted with water and extracted with ethyl acetate (2×600 mL). The combined organic layers were washed with brine solution, dried over Na₂SO₄, filtered and concentrated in vacuo. It was purified by column chromatography on silica gel with gradient elution of 20-22% of ethyl acetate in pet ether to obtain ethyl 2-((6-bromo-2-nitropyridin-3-yl)oxy)acetate, IIIb (21 g, 75.32%) as a pale yellow solid. LC-MS Calc. for C₉H₉BrN₂O₅: 305.38; Obs.: 306.2.

Step 3: Synthesis of 6-bromo-2H-pyrido[3,2-b][1,4]oxazin-3(4H)-one (III)

To a stirred solution of ethyl 2-((6-bromo-2-nitropyridin-3-yl)oxy)acetate, IIIb (21 g, 0.0687 mol) in glacial acetic acid (400 ml), Iron powder (11.51 g, 0.2063 mol) was added and heated to 100° C. for 6 hours. After completion of the reaction, reaction mixture was filtered through celite bed using ethyl acetate, 10% Methanol and concentrated in vacuo. It was washed with methanol to obtain pure 6-bromo-2H-pyrido[3,2-b][1,4]oxazin-3(4H)-one, III (12 g, 76.28%). LC-MS Calc. for C₇H₈BrN₂O₂: 229.03; Obs.: 230.2.

Synthesis of 6-(5-(aminomethyl)-2-oxooxazolidin-3-yl)-2H-pyrido[3,2-b][1,4]oxazin-3(4H)-one (Intermediate IV)

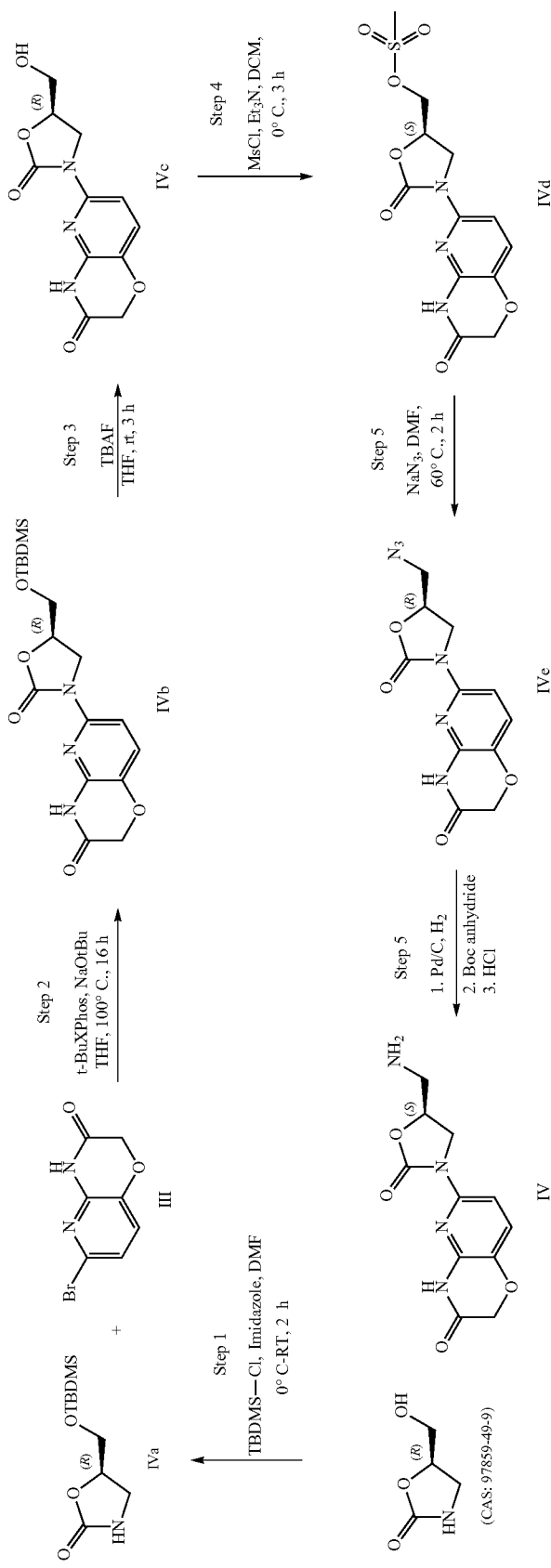

Step 1: (R)-5-(((tert-butyldimethylsilyl)oxy)methyl) oxazolidin-2-one (IVa)

To a stirred solution of TBDMS-Cl (38.46 g, 0.256 mol), imidazole (23.2 g, 0.341 mol), DMAP (2.08 g, 0.017 mol) in DMF (200 mL), cooled to 0° C., (R)-5-(hydroxymethyl)oxazolidin-2-one (CAS: 97859-49-9, 20 g, 0.1709 mmol) in DMF (25 mL) was added and stirred at 25° C. for 2 h. After completion of the reaction, reaction mixture was quenched with water and extracted with ethyl acetate. The separated organic layer was washed with water, brine solution, dried over $Na_2SO_4$, filtered and concentrated under reduced pressure. It was purified by column chromatography on silica gel (230-400 mesh, 20-25% ethyl acetate in pet ether) to obtain IVa (32 g, 81%). LC-MS Calc. for $C_{10}H_{21}NO_3Si$: 231.37; Obs.: 232.1; $^1H$ NMR (400 MHz, $CDCl_3$): δ5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H).

Step 2: (R)-6-(5-(((tert-butyldimethylsilyl)oxy) methyl)-2-oxooxazolidin-3-yl)-2H-pyrido[3,2-b][1, 4]oxazin-3(4H)-one (IVb)

To a stirred solution of IVa (32 g, 0.139 mol) and III (31.7 g, 0.139 mol) in dry 1,4-dioxane (50 mL), were added t-butyl-X-Phos mesyl chloride complex (5.5 g, 0.0069 mol) and sodium tert-butoxide (19.94 g, 0.207 mol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford IVb (45.6 g, 86%). LC-MS Calc. for $C_{17}H_{25}N_3O_5Si$: 379.49; Obs.: 380.0; $^1H$ NMR (400 MHz, DMSO-$d_6$): δ 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H).

Step 3: (R)-6-(5-(Hydroxymethyl)-2-oxooxazolidin-3-yl)-2H-pyrido[3,2-b][1,4]oxazin-3(4H)-one (IVc)

To a stirred solution of IVb (45 g, 0.118 mol) in TH (250 mL), cooled to 0° C., tert-butyl ammonium fluoride (1 M in THF) (296 mL, 0.296 mol) was added drop wise and stirred at 25° C. for 3 hours. After completion of the reaction, reaction mixture was quenched with water obtained solid filtered and dried in vacuum to obtain white solid of IVc (29 g, 92%). LC-MS Calc. for $C_{11}H_{11}N_3O$: 265.23; Obs.: 265.9; H NMR (400 MHz, DMSO-$d_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-4.07 (m, 1H), 3.92-3.88 (m, 1H), 3.69-3.65 (m, 1H), 3.54-3.34 (m, 1H).

Step 4: (R)-(2-oxo-3-(3-oxo-3,4-dihydro-2H-pyrido [3,2-b][1,4]oxazin-6-yl)oxazolidin-5-yl)methyl methanesulfonate (IVd)

To a stirred solution of IVc (29 g, 0.109 mol) in dry DMF (300 mL), cooled to 0° C., triethylamine (45.7 mL, 0.328 mol) and mesyl chloride (17 mL, 0.218 mol) were added and stirred at 25° C. for 2 h. After completion of the reaction, reaction mixture was quenched with water obtained solid filtered dried in vacuum to obtain white solid of IVd (30 g, 80%). LC-MS Calc. for $C_{12}H_{13}N_3O_7S$: 343.31; Obs.: 344.0; $^1H$ NMR (400 MHz, DMSO-d6): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H).

Step 5: (R)-6-(5-(azidomethyl)-2-oxooxazolidin-3-yl)-2H-pyrido[3,2-b][1,4]oxazin-3(4H)-one (IVe)

To a stirred solution of IVd (30 g, 0.087 mol) in DMF (300 mL), cooled to 0° C., sodium azide (17 g, 0.262 mol) was added and heated at 60° C. for 3 h. After completion of the reaction, reaction mixture was quenched with water obtained solid filtered and dried in vacuo to obtain white solid of IVe (22 g, 87%). LC-MS Calc. for $C_{11}H_{10}N_6O_4$: 290.24; Obs.: 290.9; $^1H$ NMR (400 MHz, DMSO-$d_6$): δ 11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.70-3.84 (m, 3H).

Step 6: (S)-6-(5-(aminomethyl)-2-oxooxazolidin-3-yl)-2H-pyrido[3,2-b][1,4]oxazin-3(4H)-one (IV)

To a stirred solution of IVe (22 g, 0.075 mol) in THF: MeOH (1:1) (400 ml), 10% palladium on carbon (7 g) was added and stirred at 25° C. under $H_2$ for 4 h. After completion of the reaction, reaction mixture was filtered through celite bed using THE and MeOH and concentrated under reduced pressure to obtain IV (15 g, 75%). LC-MS Calc. for $C_{11}H_{12}N_4O_4$: 264.24; Obs.: 265.1.

Purification of Intermediate IV:

Boc Protection: To a stirred solution of crude IV (15 g, 0.056 mol) in 1, 4 dioxane:water (1:1, 200 mL) was added $Na_2CO_3$ (12 g, 0.113 mol) followed by the addition of $(Boc)_2O$ (25 g, 0.113 mol) at 0° C. and allowed to stir at rt for 12 h. The reaction mixture was diluted with EtOAc (250 mL) and washed with water (2×250 mL). The combined organic layers were washed with brine (50 mL), dried over sodium sulphate and evaporated under reduced pressure to get the crude. Crude was purified by column chromatography (230/400 mesh, 4% DCM in MeOH) to get desire Boc protected IV as white solid (12 g, 58%). LC-MS Calc. for $C_{16}H_{20}N_4O_6$: 364.36; Obs.: 265.1; $^1H$ NMR (400 MHz, DMSO-D6): δ 11.23 (s, 1H), 7.61 (d, 1H, J=8.8 Hz), 7.45 (d, 1H, J=8.8 Hz), 7.24 (m, 1H), 4.71 (m, 1H), 4.60 (s, 2H), 4.16-4.11 (m, 1H), 3.84-3.80 (m, 1H), 3.25 (m, 2H), 1.36 (s, 9H).

The Boc protected IV (12 g, 0.033 mmol) was taken in 1, 4 dioxane (60 mL) and was added 4M HCl in dioxane (120 mL) at 0° C. to it. The resulting mixture was stirred at rt for 3 h. The reaction mixture was concentrated to obtain crude amine HCl salt. The crude was dissolved in dry MeOH/DCM (200 mL) and neutralized with resin, filtered and concentrated to afford pure amine IV as off white solid (8 g, 92%). LC-MS Calc. for $C_{11}H_{12}N_4O_4$: 264.24; Obs.: 265.1 [M+H]; $^1H$ NMR (400 MHz, DMSO-D6): δ 11.05 (brs, 1H), 7.62 (d, 1H, J=8.8 Hz), 7.45 (d, 1H, J=8.8 Hz), 7.05 (brs, 2H), 4.83 (m, 1H), 4.62 (s, 2H), 4.23-4.20 (m, 1H), 3.87-3.82 (m, 1H), 3.19-3.10 (m, 2H).

Synthesis of 6-chloro-2H-pyrazino[2,3-b][1,4] oxazin-3(4H)-one (Intermediate Va)

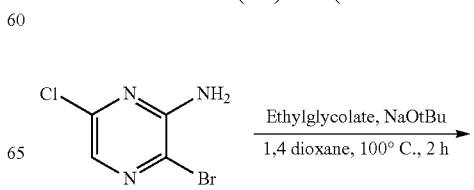

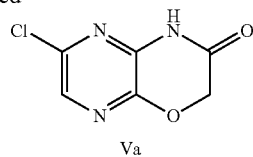

To a stirred solution of 3-bromo-6-chloropyrazin-2-amine (75 g, 0.3598 mol) in 1,4-dioxane (1500 mL) at room temperature under nitrogen atmosphere was added sodium tert-butoxide (110.65 g, 1.1514 mol) and stirred for 30 minutes. Then ethyl glycolate (112.37 g, 1.0794 mol) was added dropwise over a period of 30 minutes at room temperature. The resulting mixture was heated to 100° C. and stirred for 2 hours. The progress of the reaction was monitored by TLC.

After that the reaction mixture was cooled to room temperature and concentrated under reduced pressure to remove the dioxane. The residue obtained was diluted with water (750 mL) and neutralized using HCl (1.5 N). The precipitated solid was filtered out and dried under vacuum to get the compound Va as an off white solid. Yield: 60 g, 89.9%; LC-MS Calc. for $C_6H_4CN_3O_2$, 185.57, Observed 184.0 (M−1H); $^1$H NMR (400 MHz, DMSO-d6): δ 11.86 (s, 1H), 7.87 (s, 1H), 4.90 (s, 2H).

Synthesis of (S)-6-(5-(aminomethyl)-2-oxooxazolidin-3-yl)-2H-pyrazino[2,3-b][1,4]oxazin-3(4H)-one, (Intermediate V)

100° C. for 16 h. After completion of the reaction, reaction mixture was concentrated under reduced pressure. It was purified by column chromatography on silica gel (230-400 mesh, 25-30% ethyl acetate in pet ether) to afford Vb (3 g, 59%). LC-MS Calc. for $C_{16}H_{24}N_4O_5Si$, 380.48, Observed 381.1 (M$^+$1H); $^1$H NMR (400 MHz, DMSO-d$_6$): δ 11.61 (s, 1H), 8.37-8.35 (m, 1H), 4.85-4.79 (m, 3H), 4.12-4.06 (m, 1H), 3.89-3.74 (m, 3H), 0.84-0.71 (m, 9H), 0.03-0.00 (m, 6H).

Step 2: (R)-6-(5-(hydroxymethyl)-2-oxooxazolidin-3-yl)-2H-pyrazino[2,3-b][1,4]oxazin-3(4H)-one (Vc)

To a stirred solution of Vb (3 g, 7.89 mmol) in THF (30 mL), cooled to 0° C., tert-butyl ammonium fluoride (1 M in THF) (15.8 mL, 15.78 mmol) was added dropwise and stirred at room temperature for 3 hours. After completion of the reaction, reaction mixture was quenched with water, extracted with ethyl acetate, dried over sodium sulphate and evaporated. The crude was purified by column chromatography on silica gel (230-400 mesh, 50-50% ethyl acetate in pet ether) to afford Vc (1.5 g, 71%). LC-MS Calc. for $C_{10}H_{10}N_4O$, 266.21, Observed 267.1 (M$^+$1H); $^1$H NMR (400 MHz, DMSO-d$_6$): δ 11.62 (s, 1H), 8.38 (s, 1H), 5.23-5.07 (m, 2H), 5.03 (s, 1H), 4.86-4.73 (m, 1H), 4.10-3.86 (m, 2H), 3.70-3.48 (m, 2H).

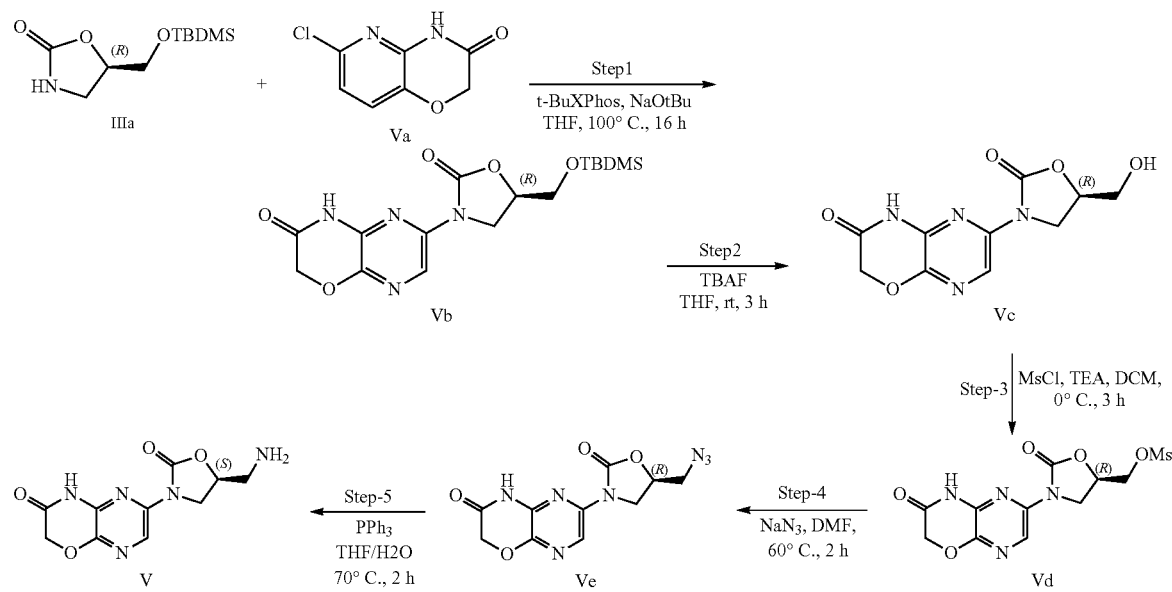

Step 1: (R)-6-(5-(((tert-butyldimethylsilyl)oxy)methyl)-2-oxooxazolidin-3-yl)-2H-pyrazino[2,3-b][1,4]oxazin-3(4H)-one (Vb)

To a stirred solution of Va (2.5 g, 13.51 mmol) and IIIa (3.43 g, 14.86 mmol) in dry 1,4-Dioxane (40 mL), were added t-butyl-X-Phos mesyl chloride complex (0.53 g, 0.67 mmol) and sodium tert-butoxide (1.94 g, 20.27 mmol) and degassed for 20 mins. Then, it was heated in sealed tube at Alternative Route for the Synthesis of Vc

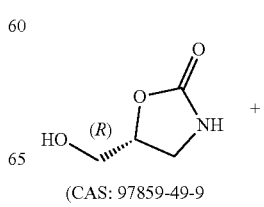

(CAS: 97859-49-9)

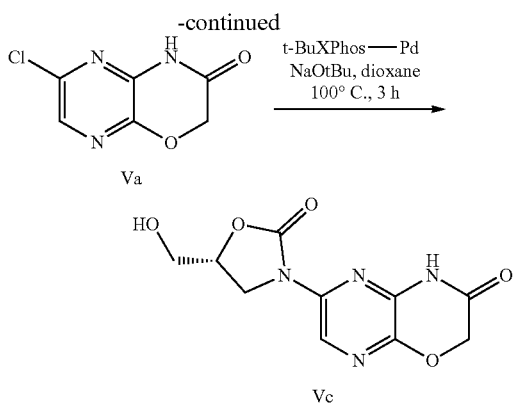

To a stirred solution of Va (40.0 g, 0.215 mol) and (R)-5-(hydroxymethyl)oxazolidin-2-one (CAS: 97859-49-9, 28.0 g, 0.237 mol) in 1,4-dioxane (600 mL) was added sodium tert-butoxide (31.08 g, 0.323 mol) at room temperature. The resulting mixture was degassed with a stream of nitrogen and was added t-butyl-X-Phos Palladacycle (8.56 g, 0.0107 mol) at room temperature. The resulting mixture was then heated to 100° C. and stirred for 3 hours. After that, the reaction mixture was cooled to room temperature, concentrated in vacuo. The residue obtained was diluted with water (500 mL), neutralised with 1.5 N HCl (pH~7). The solid precipitated out was filtered and washed with diethyl ether, dried under vacuo to get compound Vc as brown solid. Yield: 55.0 g (crude), 95.9%.

Step 3: (R)-(2-oxo-3-(3-oxo-3,4-dihydro-2H-pyrazino[2,3-b][1,4]oxazin-6-yl)oxazolidin-5-yl)methyl methanesulfonate (Vd)

To a stirred solution of Vc (1.5 g, 5.63 mmol) in dry DMF (15 mL), cooled to 0° C., Triethylamine (2.3 mL, 16.91 mmol) and mesyl chloride (0.69 mL, 8.45 mmol) were added and stirred at 25° C. for 2 h. After completion of the reaction, reaction mixture was quenched with water, the resultant solid was filtered, washed with pet ether and dried by vacuum to afford brown solid of Vd (1.2 g, 63%). LC-MS Calc. for $C_{11}H_{12}N_4O_7S$, 344.30, Observed 345.0 (M+1H); $^1$H NMR (400 MHz, DMSO-$d_6$): δ 11.67 (s, 1H), 8.38 (s, 1H), 5.06-5.04 (m, 1H), 4.87 (s, 2H), 4.57-4.54 (m, 2H), 4.23-4.20 (m, 1H), 3.86-3.82 (m, 1H), 3.28 (s, 3H), 3.25-3.23 (m, 1H).

Step 4: (R)-6-(5-(azidomethyl)-2-oxooxazolidin-3-yl)-2H-pyrazino[2,3-b][1,4]oxazin-3(4H)-one (Ve)

To a stirred solution of Vd (1.2 g, 3.48 mmol) in DMF (12 mL), cooled to 0° C., sodium azide (0.56 g, 8.72 mmol) was added and heated at 65° C. for 3 h. After completion of the reaction, reaction mixture was quenched with water, the obtained solid was filtered, washed with pet ether and dried to afford the brown solid Ve (0.7 g, 70%). LC-MS Calc. for $C_{10}H_9N_7O_4$, 291.23, Observed 290.1 (M−1H); $^1$H NMR (400 MHz, DMSO-$d_6$): δ 11.66 (s, 1H), 4.94-4.86 (m, 3H), 4.18-4.13 (m, 1H), 3.81-3.75 (m, 3H).

Step 5 (S)-6-(5-(aminomethyl)-2-oxooxazolidin-3-yl)-2H-pyrazino[2,3-b][1,4]oxazin-3(4H)-one (V)

To a stirred solution of Ve (0.7 g, 2.40 mmol) in THF:MeOH (1:1) (40 ml) was added PPh$_3$ (1.9 g, 7.21 mmol) at room temperature. The reaction mixture was heated at 70° C. for 3 h. After completion of the reaction by TLC, reaction mixture was cooled to room temperature, and was extracted with ethyl acetate (2×100 ml) for 2 times. Further the aqueous layer was concentrated and dried to afford V (0.3 g, 47%). LC-MS Calc. for $C_{10}H_{11}NO_4$, 265.23, Observed 264.1 (M−1H); $^1$H NMR (400 MHz, DMSO-$d_6$): δ 8.38 (s, 1H), 4.85 (s, 2H), 4.69-4.67 (m, 1H), 4.11-4.06 (m, 1H), 3.88-3.84 (m, 1H), 3.17 (s, 1H), 2.91-2.83 (m, 2H).

Synthesis of (R)-6-(5-(aminomethyl)-2-oxooxazolidin-3-yl)-2H-pyrazino[2,3-b][1,4]oxazin-3(4H)-one (Intermediate VI)

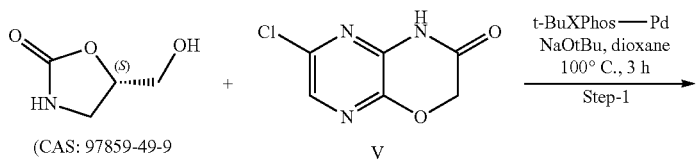

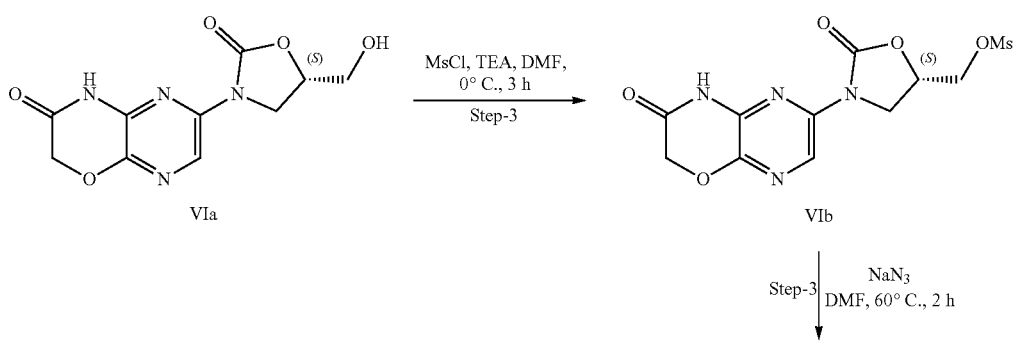

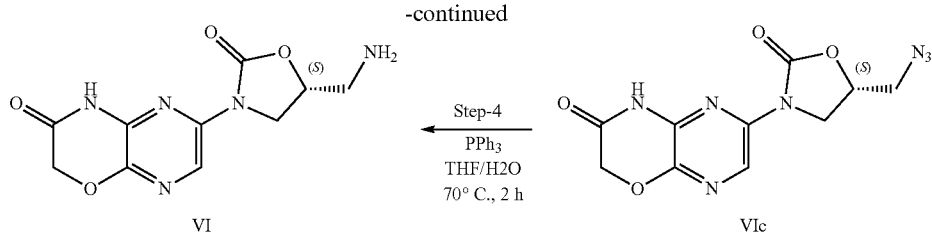

Intermediate VI was synthesized using scheme and procedures analogues to Intermediate V involving (S)-5-(hydroxymethyl)oxazolidin-2-one (CAS: 97859-49-9) and 6-chloro-2H-pyrazino[2,3-b][1,4]oxazin-3(4H)-one (Va) as starting materials. LC-MS Calc. for $C_{10}H_{11}N_5O_4$, 265.23, Observed 264.2 (M−1H); $^1$H NMR (400 MHz, DMSO-$d_6$): δ 8.36 (s, 1H), 4.84 (s, 2H), 4.69-4.65 (m, 1H), 4.12-4.06 (m, 1H), 3.89-3.84 (m, 1H), 3.16 (s, 1H), 2.92-2.83 (m, 2H).

Synthesis of 6-chloro-2H-pyrazino[2,3-b][1,4]thiazin-3(4H)-one, VIIa

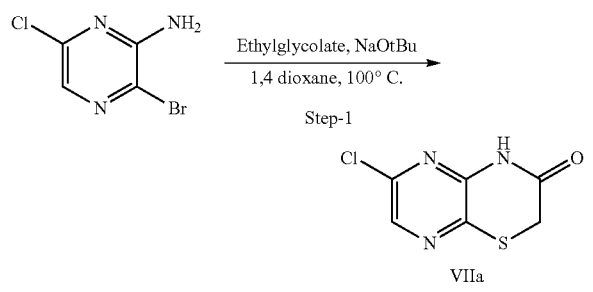

To a stirred solution of 3-bromo-6-chloropyrazin-2-amine I (10 g, 0.0479 mol) in 1, 4-dioxane (1.5 L) at room temperature under nitrogen atmosphere was added sodium tert-butoxide (14.75 g, 0.1535 mol) and stirred for 30 minutes. Then ethyl thioglycolate (11.53 g, 0.0959 mol) was added in dropwise over a period of 30 minutes at room temperature. The resulting mixture was heated to 100° C. and stirred for 2 hours. The progress of the reaction was monitored by TLC.

After that, the reaction mixture was cooled to room temperature and concentrated under reduced pressure to remove the dioxane. The residue obtained was diluted with water (750 mL) and neutralized using HCl (1.5 N). The precipitated solid was filtered out and dried to get the compound VIIa as an off white solid. Yield: 6 g, 62.5%; LC_MS: Calc. for $C_6H_4CN_3O_S$: 201.63; Obs.: 199.9 [M−1H]. $^1$H-NMR (400 MHz, DMSO-$d_6$): δ 11.54 (s, 1H), 8.25 (s, 1H), 3.83 (s, 2H).

Synthesis of (S)-5-(aminomethyl)-3-(3-oxo-3,4-dihydro-2H-pyrazino[2,3-b][1,4]thiazin-6-yl)oxazolidin-2-one (Intermediate VII)

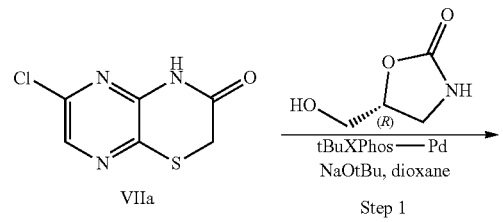

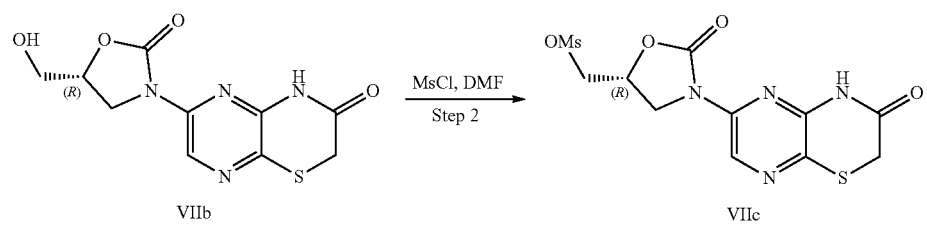

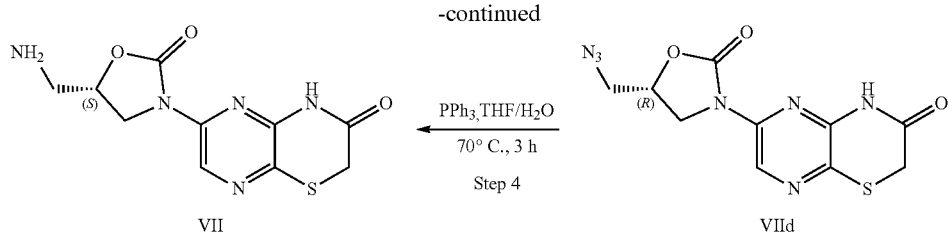

Step 1: (R)-5-(hydroxymethyl)-3-(3-oxo-3,4-dihydro-2H-pyrazino[2,3-b][1,4]thiazin-6-yl)oxazolidin-2-one (VIIb)

To a stirred solution of compound VIIa (6 g, 0.0297 mol) and (R)-5-(hydroxymethyl)oxazolidin-2-one (CAS: 97859-49-9, 3.83 g, 0.0327 mol) in 1.4-dioxane (100 mL) was added sodium tert-butoxide (4.29 g, 0.0446 mol) at room temperature. The resulting mixture was degassed with a stream of nitrogen for 10 minutes. Then t-butyl-X-Phos Palladacycle (1.18 g, 0.0014 mol) was added at room temperature and again degassed with nitrogen for 5 minutes. The resulting mixture was then heated to 100° C. and stirred for 5 hours. After that, the reaction mixture was cooled to room temperature and concentrated in vacuo. The residue obtained was diluted with water (50 mL), neutralized with aqueous HCl (1.5 N, pH~7). The solid precipitated out was filtered and washed with diethyl ether, dried under vacuo to get compound VIIb as brown solid. Yield: 4 g (crude), which was taken for the next step without any further purification. LC_MS: Calc. for $C_{10}H_{10}N_4O_4S$: 282.27; Obs.: 283.2 [M+H]+. $^1$H NMR (300 MHz, DMSO-$d_6$): δ 11.24 (s, 1H), 8.24 (s, 1H), 5.27-5.24 (m, 1H), 4.80-4.76 (m, 1H), 4.09 (t, J=9.36 Hz, 1H), 3.91-3.87 (m, 1H), 3.78-3.68 (m, 3H), 3.60-3.57 (m, 1H).

Step 2: (R)-(2-oxo-3-(3-oxo-3,4-dihydro-2H-pyrazino[2,3-b][1,4]thiazin-6-yl)oxazolidin-5-yl)methyl methanesulfonate (VIIb)

To a stirred solution of VIIa (4 g, 0.0141 mol) in dry DMF (40 mL) at 0° C. under nitrogen atmosphere were added triethylamine (5.5 mL, 0.0425 mol) and mesyl chloride (2.43, 0.0215 mol) successively. The reaction mixture was then warmed to room temperature and stirred for 2 h. After that the reaction mixture was quenched with water, the solid formed was filtered, washed with petroleum ether and dried to get compound VIIb as a brown solid (3 g, crude), which was taken for the next step without any further purification. LC_MS: Calc. for $C_{11}H_2N_4O_6S_2$: 360.36; Obs.: 361.00 [M+H]+.

Step 3: (R)-5-(azidomethyl)-3-(3-oxo-3,4-dihydro-2H-pyrazino[2,3-b][1,4]thiazin-6-yl)oxazolidin-2-one (VIIc)

To a stirred solution of VIIb (3.0 g, 0.0083 mol) in DMF (30 mL) at 0° C. under nitrogen atmosphere was added sodium azide (2.16 g, 0.033 mol). The reaction mixture was then heated to 65° C. and stirred for 3 h. After that, reaction mixture was quenched with water, the solid obtained was filtered, washed with petroleum ether and dried to get compound VIIc as a brown solid (1.7 g, 66.66%). LC_MS: Calc. for $C_{10}H_9N_7O_3S$: 307.29; Obs.: 307.9 [M+H]+.

Step 4: (S)-5-(aminomethyl)-3-(3-oxo-3,4-dihydro-2H-pyrazino[2,3-b][1,4]thiazin-6-yl)oxazolidin-2-one (VII)

To a stirred solution of compound VIIc (1.7 g, 0.0055 mol) in a mixture of THF:$H_2O$ (1:1) (80 mL) under nitrogen atmosphere was added PPh$_3$ (4.34 g, 0.0165 mol) at room temperature. The reaction mixture was heated to 70° C. and stirred for 3 hours. After completion of the reaction by TLC, the reaction mixture was cooled to room temperature and extracted with ethyl acetate (2×100 mL). The aqueous layer was separated and concentrated in vacuo to get compound VII (0.9 g, 58.06%). LC_MS: Calc. for $C_{10}H_{11}N_5O_3S$: 281.29; Obs.: 282.1 [M+H]+.

Synthesis of 2-(6-Fluoro-4-methyl-3-oxo-3,4-dihydroquinoxalin-5-yl)acetaldehyde, (Intermediate VIII)

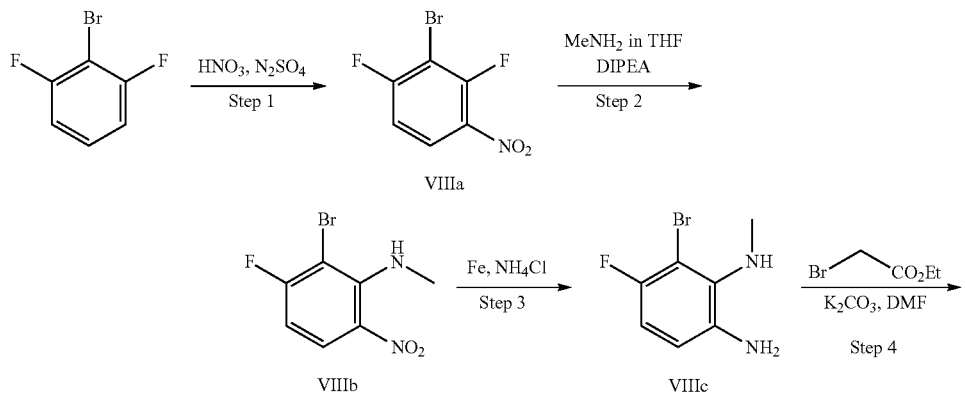

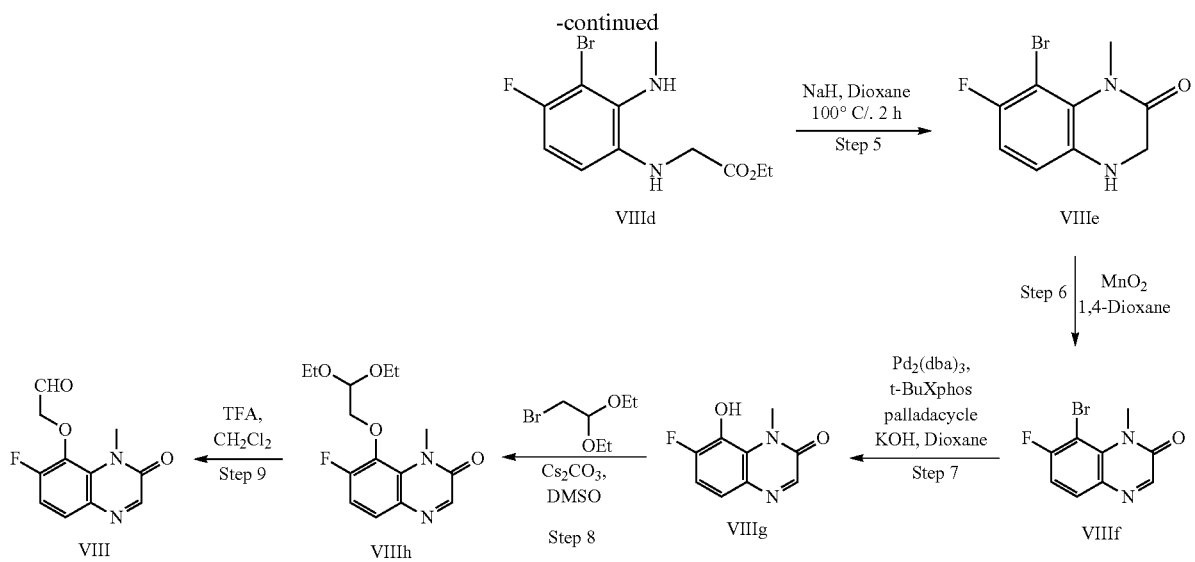

Step 1: 2-Bromo-1, 3-difluoro-4-nitrobenzene (VIIIa)

To a stirred solution of 2-bromo-1,3-difluorobenzene (CAS 64248-56-2, 10.0 g, 51.8 mmol) in $H_2SO_4$ (30 mL) at 0° C. under nitrogen atmosphere was added $HNO_3$ (65%, 25 mL) in dropwise. The resulting mixture was warmed to room temperature and stirred for 1 hour. After that, the reaction mixture was poured onto ice and vigorously stirred for 5 minutes. The resulting suspension was extracted with $CH_2Cl_2$ (4×125 mL), washed with brine (200 mL), dried over $Na_2SO_4$ and concentrated in vacuo to get compound VIIIa (crude). The obtained crude product was taken for the next step without any further purification. Yield: 9.00 g, 72.99%. $^1$H-NMR (400 MHz, DMSO-$d_6$): δ 8.34-8.29 (m, 1H), 7.56-7.51 (m, 1H).

Step 2: 2-Bromo-3-fluoro-N-methyl-6-nitroaniline (VIIIb)

To a stirred solution of compound VIIIa (9.00 g, 37.8 mmol) and DIPEA (13.3 mL, 75.6 mmol) in THF (90 mL) at room temperature under nitrogen atmosphere was added methylamine (2M in THF, 37.8 mL, 75.6 mmol). The resulting mixture was heated to 60° C. and stirred for 3 hours. After that, the reaction mixture was concentrated under reduced pressure and the residue obtained was purified by column chromatography using silica gel (60-120 mesh) eluting with petroleum ether to give compound VIIb as pale yellow colour solid. Yield: 7.70 g, 81.74%. $^1$H-NMR (400 MHz, DMSO-$d_6$): δ 7.91-7.87 (m, 1H), 6.80-6.76 (m, 2H), 2.75 (s, 3H).

Step 3: 6-Bromo-5-fluoro-$N_1$-methylbenzene-1, 2-diamine (VIIIc)

To a stirred solution of compound VIIb (7.70 g, 30.9 mmol) in a mixture of methanol/water (400 mL, 3:1) were added ammonium chloride (8.20 g, 154.6 mmol) and iron powder (6.90 g, 123.7 mmol) successively. The resulting mixture was heated at reflux for 16 hours. After that, the reaction mixture was filtered to the solid material and the filtrate was concentrated under reduced pressure. The residue obtained was diluted with water and extracted with ethyl acetate (2×300 mL). The combined organic phase was washed with brine, dried over $Na_2SO_4$ and concentrated in vacuo. The obtained residue was further purified by column chromatography using silica gel (230-400 mesh) eluting with 15-20% ethyl acetate in petroleum ether to get compound VIIIc as pale brown colour solid. Yield: 3.50 g, 51.69%; $^1$H NMR (400 MHz, DMSO-$d_6$): δ 6.70 (t, J=8.6 Hz, 1H), 6.61-6.59 (m, 1H), 4.82 (brs, 2H), 3.92 (brs, 1H), 2.61 (s, 3H).

Step 4: Ethyl (3-bromo-4-fluoro-2-(methylamino) phenyl) glycinate (VIIId)

To a stirred solution of compound VIIIc (3.50 g, 16.0 mmol) in DMF (70 mL) at 0° C. under nitrogen atmosphere were added $K_2CO_3$ (3.30 g, 23.9 mmol) and ethyl bromoacetate (2.10 mL, 19.2 mmol) successively. The resulting mixture was heated to 75° C. and stirred for 1 hour. Upon completion, the reaction mixture was quenched with ice cold water (50 mL) and extracted with ethyl acetate (4×100 mL). The combined organic phase was washed with brine, dried over $Na_2SO_4$ and concentrated in vacuo. The obtained crude product was purified by column chromatography using silica gel (230-400 mesh) eluting with 10-15% of ethyl acetate in petroleum ether to get compound VIIId. Yield: 3.50 g, 71.86%. $^1$H-NMR (400 MHz, DMSO-$d_6$): δ 6.84 (t, J=8.6 Hz, 1H), 6.41-6.38 (m, 1H), 5.39-5.37 (m, 1H), 4.16-4.08 (m, 1H), 4.01-3.94 (m, 1H), 2.59 (d, J=5.7 Hz, 3H), 1.18 (t, J=7.0 Hz, 3H).

Step 5: 8-Bromo-7-fluoro-1-methyl-3,4-dihydroquinoxalin-2(1H)-one (VIIIe)

To a stirred solution of compound VIIId (3.50 g, 11.5 mmol) in 1, 4-Dioaxne (70 mL) at 0° C. under nitrogen atmosphere was added NaH (60% dispersion in oil, 0.14 g, 3.44 mmol). The resulting mixture was heated 100° C. and stirred for 2 hours. After that, reaction mixture was quenched with ice cold water (50 mL) and extracted with ethyl acetate (3×100 mL). The combined organic phase was washed with brine (100 mL), dried over $Na_2SO_4$ and concentrated in vacuo. The obtained crude product was further purified by column chromatography using silica gel (230-400 mesh) eluting with 25-30% of ethyl acetate in petroleum ether to get compound VIIIe as off-white solid. Yield: 2.70 g, 90.91%. $^1$H-NMR (400 MHz, DMSO-$d_6$): δ 6.99-6.94 (m, 1H), 6.88-6.84 (m, 1H), 6.24 (s, 1H), 3.60 (s, 2H), 3.35 (s, 3H).

Step 6: 8-Bromo-7-fluoro-1-methylquinoxalin-2(1H)-one (VIIIf)

To a stirred solution of compound VIIIe (2.7 g, 10.42 mmol) in 1, 4-dioxane (30 mL) at room temperature under nitrogen atmosphere was added MnO$_2$ (5.44 g, 62.54 mmol) at once. The resulting mixture was heated to 100° C. and stirred for 2 hours. After that the reaction mixture was cooled to room temperature, filtered through celite pad and thoroughly washed with ethyl acetate. The combined filtrate was concentrated under reduced pressure to get compound VIIIf (crude) as a pale brown solid, which was used for the next step without any further purification. Yield: 2.1 g (crude). $^1$H-NMR (300 MHz, DMSO-$d_6$): δ 8.24 (s, 1H), 7.91-7.86 (m, 1H), 7.46-7.40 (m, 1H), 3.91 (s, 3H).

Step 7: 7-Fluoro-8-hydroxy-1-methylquinoxalin-2(1H)-one (VIIIg)

A stirred solution of compound VIIIf (2.1 g, 8.17 mmol) in a mixture of 1,4-dioxane (25 mL) and water (15 mL) at room temperature was degassed with a stream of nitrogen for 15 minutes. Then t-BuXPhos Palladacycle (0.19 g, 0.24 mmol) and tris (dibenzylideneacetone)dipalladium (0) (0.15 g, 0.16 mmol) were added successively. The resulting mixture was again degassed with stream of nitrogen for 10 minutes. Then KOH (0.91 g, 16.34 mmol) was added to the reaction mixture under nitrogen atmosphere. The resulting mixture was then heated to 100° C. and stirred for 16 hours.

After that the reaction mixture was cooled to 0° C., quenched with water and washed with ethyl acetate (2×50 mL). The aqueous phase was then acidified with 1.5 HCl (5 mL) and extracted with ethyl acetate (3×50 mL). The combined organic phase was washed with brine solution (50 mL), dried over Na$_2$SO$_4$ and concentrated in vacuo to get compound VIIIg (crude) as a pale brown solid. The crude product was taken for the next step without any further purification. Yield: 1.1 g, 69.62%. LC_MS: Calc. for C$_9$H$_7$FN$_2$O$_2$ 194.17; Obs.: 194.9 [M+H]$^+$.

Step 8: 8-(2,2-Diethoxyethoxy)-7-fluoro-1-methylquinoxalin-2(1H)-one (VIIIh)

To a stirred solution of compound VIIIg (1.1 g, 5.67 mmol) in dimethyl sulfoxide (11 mL) at room temperature under nitrogen atmosphere were added cesium carbonate (2.57 g, 7.93 mmol) and bromoacetaldehyde diethyl acetal (1.4 mL, 8.50 mmol) successively. The resulting mixture was heated to 90° C. and stirred for 16 hours. After that the reaction mixture was diluted with water (20 mL) and extracted with ethyl acetate (3×25 mL). The combined organic phase was washed with brine solution, dried over Na$_2$SO$_4$ and concentrated in vacuo. The obtained crude product was further purified by column chromatography using silica gel (230-400 mesh) eluting with 15% ethyl acetate in petroleum ether to get compound VIIIh as a pale brown solid. Yield: 1.2 g, 70.58%. LC_MS: Calc. for C$_{15}$H$_{19}$FN$_2$O$_4$ 310.33; Obs.: 311.2 [M+H]$^+$.

Step 9: 2-((6-Fluoro-4-methyl-3-oxo-3,4-dihydroquinoxalin-5-yl)oxy)acetaldehyde (VIII)

To a stirred solution of compound VIIIh (1.2 g, 3.86 mmol) in dichloromethane (15 mL) at 0° C. under nitrogen atmosphere was added trifluoroacetic acid (6 mL, 5 volume) in dropwise. The resulting mixture was allowed to stir at room temperature for 2 hours. After that the reaction mixture was concentrated, basified with 10% NaHCO$_3$ solution, extracted with dichloromethane (3×50 mL), dried over Na$_2$SO$_4$ and concentrated in vacuo to get compound VIII (crude) as a brown solid. The crude product was used as such for the next step without further purification. Yield: 0.6 g. LC_MS: Calc. for C$_{11}$H$_9$FN$_2$O$_3$ 236.2; Obs: 237.0 [M+H]$^+$.

Synthesis of 2-(7-fluoro-1, 4-dimethyl-2-oxo-1,2-dihydroquinolin-8-yl)acetaldehyde, (Intermediate IX)

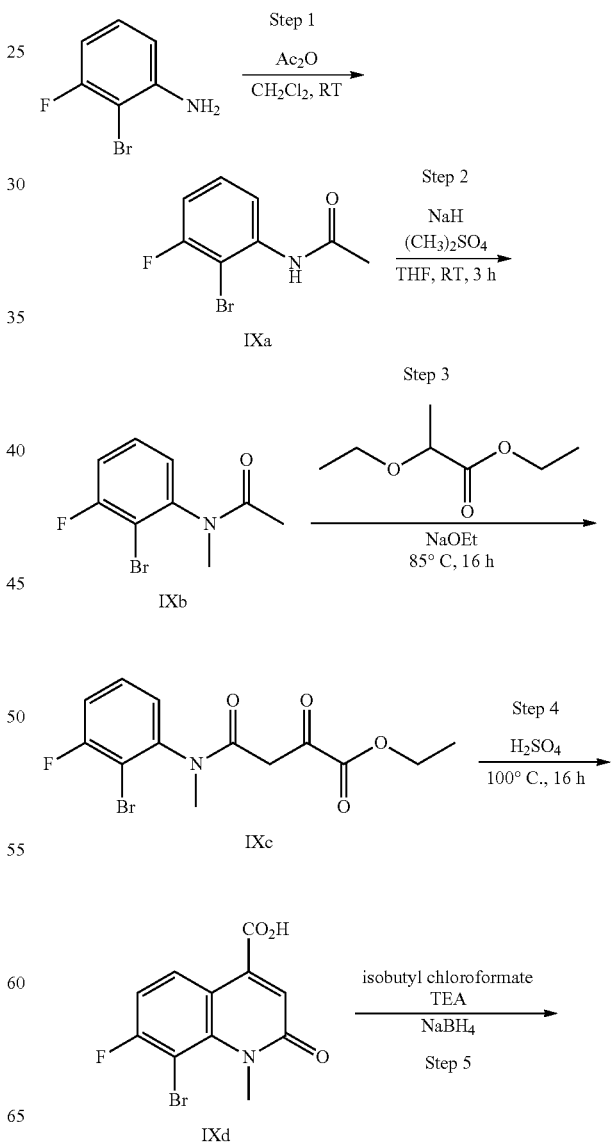

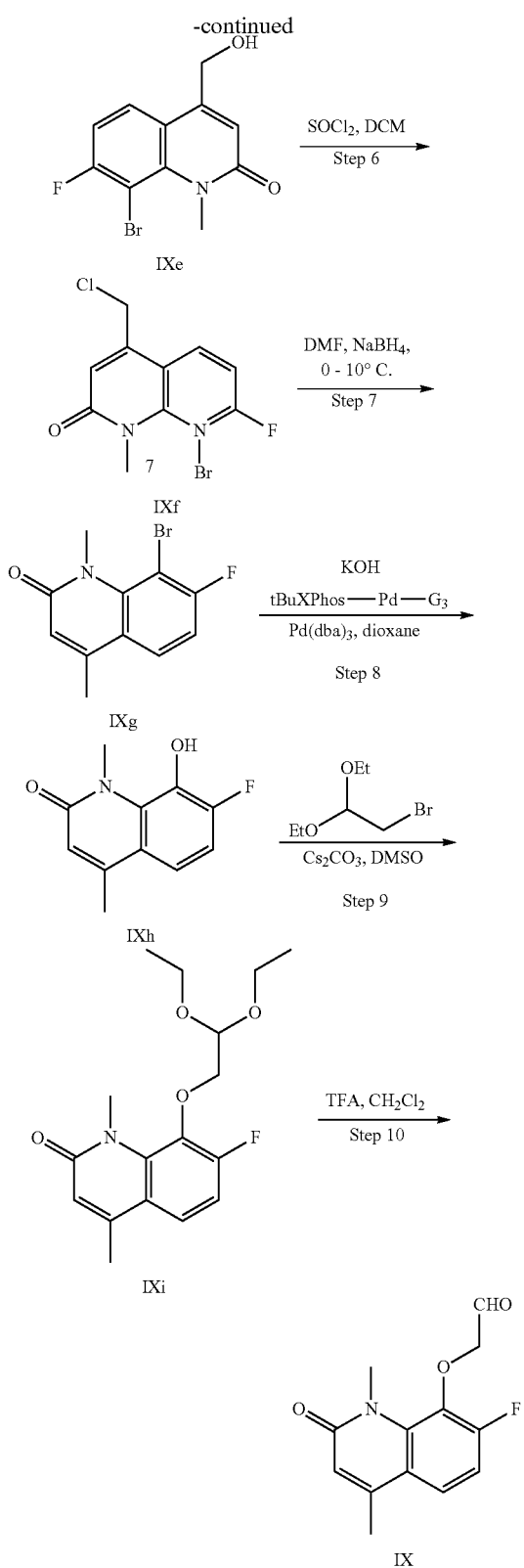

Step 1: N-(2-Bromo-3-fluorophenyl) acetamide (IXa)

To a stirred solution of 2-bromo-3-fluoro aniline (25.0 g, 131.57 mmol) in dichloromethane (500 mL) at 0° C. under nitrogen was added acetic anhydride (18.65 mL, 197.36 mmol). The resulting mixture was warmed to room temperature and stirred for 16 hours. After that, the reaction mixture was diluted water and extracted with dichloromethane (2×500 mL). The combined organic phase was washed with brine, dried over anhydrous $Na_2SO_4$ and concentrated in vacuo to get compound IXa (crude), which was taken as such for the next step without further purification. Yield: 25 g, 81.91%. LC-MS Calc. for $C_8H_7BrFNO$, 232.05; Obs.; 232.0 $[M^+]$; $^1$H-NMR (300 MHz, DMSO-$d_6$): δ 9.57 (s, 1H), 7.49-7.34 (m, 2H), 7.20-7.14 (m, 1H), 2.09 (s, 3H).

Step 2: N-(2-Bromo-3-fluorophenyl)-N-methylacetamide (IXb)

To a stirred solution of compound IXa (25.0 g, 107.73 mmol) in dry THF (500 mL) under nitrogen atmosphere was added sodium hydride (60% in mineral oil, 5.38 g, and 134.66 mmol) and stirred for 30 minutes. Then dimethyl sulphate (13.79 mL, 145.44 mmol) was added to the reaction mixture at 0° C. The resulting mixture was warmed to room temperature and stirred at room temperature for 3 hours. After that, the reaction mixture was diluted with water and extracted with ethyl acetate (2×500 mL). The combined organic phase was washed with brine, dried over sodium sulfate and concentrated in vacuo to get compound IXb as a white solid, which was used as such for the next step without further purification. Yield: 20 g, 75.47%. LC-MS Calc. for $C_9H_9BrFNO$ 246.08; Obs.: 248.0; $[M^++2H]$; $^1$H NMR (300 MHz, DMSO-$d_6$): δ 7.58-7.32 (m, 3H), 3.05 (s, 3H), 1.67 (s, 3H).

Step 3: Ethyl 4-((2-bromo-3-fluorophenyl)(methyl)amino)-2,4-dioxobutanoate (IXc)

To a stirred solution of compound IXb (20.0 g, 81.95 mmol) in sodium ethoxide (20% in ethanol, 55 mL, 163.90 mmol) at room temperature under nitrogen atmosphere was added diethyl oxalate (47.89 g, 327.81 mmol). The resulting mixture was then heated at 80° C. and stirred for 16 hours. After that, the reaction mixture was completely evaporated under reduced pressure to get crude compound, which was further purified by column chromatography silica gel (230-400 mesh, 40% EtOAc in Petroleum ether) to get compound IXc as a colorless oil. Yield: 15.0 g, 53.32%. LC-MS Calc. for $C_{13}H_3BrFNO_4$ 346.15; Obs.: 347.0 $[M^++H]$; $^1$H NMR (400 MHz, DMSO-$d_6$): δ 7.63-7.48 (m, 3H), 5.37 (s, 1H), 4.18-4.13 (m, 2H), 3.22 (s, 3H), 1.30-1.15 (m, 3H).

Step 4: 8-Bromo-7-fluoro-1-methyl-2-oxo-1, 2-dihydroquinoline-4-carboxylic acid (IXd)

A solution of compound IXc (23.0 g, 66.44 mmol) in Con $H_2SO_4$ (230 mL) was heated to 90° C. and stirred for 16 hours. After that, the reaction mixture was quenched with ice cold water and extracted with ethyl acetate (2×500 mL), washed with water, brine, dried over sodium sulfate and concentrated in vacuo. The obtained crude product was further triturated with diethyl ether, filtered and dried to get compound IXd as a white solid, which was used as such for the next step without further purification. Yield: 15 g, 75.26%. LC-MS Calc. for $C_{11}H_7BrFNO_3$ 300.08; Obs.: 300.0; $[M^+]$; $^1$H NMR (400 MHz, DMSO-$d_6$): δ 14.22 (s, br, 1H), 8.25-8.22 (m, 1H), 7.40-7.35 (m, 1H), 6.95 (s, 1H), 3.81 (s, 3H).

Step 5: 8-Bromo-7-fluoro-4-(hydroxymethyl)-1-methylquinolin-2(1H)-one (IXe)

To a stirred solution of compound IXd (12.0 g, 40.00 mmol) in THF (120 mL) at 0° C. under nitrogen atmosphere were added triethylamine (7.23 mL, 52.00 mmol) and isobutyl chloroformate (6.55 g, 48 mmol) successively and stirred for 1 hour. Then NaBH$_4$ (3.80 g, 100.00 mmol) in portions and methanol (10 mL) were added to the reaction mixture and continued to stir for 10 minutes. After that, the reaction mixture was diluted with water and extracted with ethyl acetate (2×500 mL). The combined organic phase was washed with brine, dried over sodium sulfate and concentrated in vacuo. The obtained crude product was purified by column chromatography silica gel (230-400 mesh, 40% EtOAc in petroleum ether) to get compound IXe as a white solid. Yield: 6.5 g, 56.82%. LC-MS Calc. for C$_{11}$H$_9$BrFNO$_2$, 286.10; Obs.: 288.0 [M$^+$+2H]; $^1$H NMR (400 MHz, DMSO-d$_6$): δ 7.82-7.78 (m, 1H), 7.34-7.30 (m, 1H), 6.68 (s, 1H), 5.61-5.58 (m, 1H), 4.74-4.72 (m, 2H), 3.80 (s, 3H).

Step 6: 8-Bromo-4-(chloromethyl)-7-fluoro-1-methylquinolin-2(1H)-one (IXf)

To a stirred solution of compound IXe (3.0 g, 10.48 mmol) in dichloromethane (60 mL) at 0° C. under nitrogen atmosphere was added thionyl chloride (2.34 mL, 31.46 mmol) in dropwise. The resulting mixture was then warmed to room temperature and stirred for 5 hours. After that, the reaction mixture was quenched with 10% aqueous NaHCO$_3$ solution and extracted with dichloromethane (2×100 mL). The combined organic extract was washed with brine, dried over sodium sulfate and concentrated in vacuo. The obtained crude product was further purified by column chromatography using silica gel (230-400 mesh) eluting with 20% EtOAc in petroleum ether) to get compound IXf as an off-white solid. Yield: 1.5 g, 47.16%. LC-MS Calc. for C$_{11}$H$_8$BrClFNO, 304.54; Obs.: 306.0 [M$^+$+2H]; $^1$H-NMR (300 MHz, DMSO-d$_6$): δ 7.98-7.93 (m, 1H), 7.44-7.39 (m, 1H), 6.87 (s, 1H), 5.04 (s, 2H), 3.81 (s, 3H).

Step 7: 8-Bromo-7-fluoro-1,4-dimethylquinolin-2(1H)-one (IXg)

To a stirred solution of compound IXf (1.5 g, 4.93 mmol) in DMF (30 mL) at 0° C. under nitrogen atmosphere was added NaBH$_4$ (93 mg, 2.46 mmol). The resulting mixture was warmed to room temperature and stirred for 3 hours. After that, the reaction mixture was cooled to 0° C., quenched with water (60 mL) and extracted with ethyl acetate (2×100 mL). The combined organic phase was washed with brine, dried over sodium sulfate and concentrated in vacuo. The obtained crude product was further purified by column chromatography using silica gel (230-400 mesh) 20% ethyl acetate in petroleum ether) to get compound IXg as an off-white solid. Yield: 0.7 g, 53.84%. LC-MS Calc. for C$_{11}$H$_9$BrFNO, 270.10; Obs.: 272.0 [M$^+$+2H]; $^1$H NMR (400 MHz, DMSO-d$_6$): δ 7.83 (m, 1H), 7.31 (m, 1H), 6.55 (s, 1H), 3.78 (s, 3H), 2.40 (s, 3H).

Step 8: 7-Fluoro-8-hydroxy-1,4-dimethylquinolin-2(1H)-one (IXh)

A stirred solution of compound IXg (1.0 g, 3.7037 mmol) in a mixture of 1,4-dioxane (15 mL) and water (5 mL) at room temperature was degassed with a stream of nitrogen for 15 minutes. Then t-BuXPhos Palladacycle (90 mg, 0.1111 mmol) and tris (dibenzylideneacetone)dipalladium (0) (68 mg, 0.074 mmol) were added successively. The resulting mixture was again degassed with stream of nitrogen for 10 minutes. Then KOH (0.415 g, 7.4074 mmol) was added to the reaction mixture under nitrogen atmosphere at room temperature. The resulting mixture was then heated to 100° C. and stirred for 16 hours.

After that the reaction mixture was cooled to 0° C., quenched with water and washed with ethyl acetate (2×50 mL). The aqueous phase separated was then acidified with HCl (1.5 N, 5 mL) and extracted with ethyl acetate (3×50 mL). The combined organic phase was washed with brine solution (50 mL), dried over Na$_2$SO$_4$ and concentrated in vacuo to get compound IXh (crude) as a pale brown solid, which was taken for the next step without any further purification. Yield: 0.5 g, 65.86%. LC_MS: Calc. for C$_{11}$H$_{10}$FNO$_2$ 207.2; Obs.: 208.1 [M+H]$^+$.

Step 9: 8-(2,2-Diethoxyethoxy)-7-fluoro-1,4-dimethylquinolin-2(1H)-one (IXi)

To a stirred solution of compound IXh (0.5 g, 2.41 mmol) in dimethyl sulfoxide (10 mL) at room temperature under nitrogen atmosphere were added cesium carbonate (1.1 g, 3.38 mmol) and bromoacetaldehyde diethyl acetal (0.55 mL, 3.62 mmol). The reaction mixture was then heated to 90° C. and stirred for 16 hours. After that the reaction mixture was diluted with water (20 mL) and extracted with ethyl acetate (3×25 mL). The combined organic phase was washed with brine solution, dried over Na$_2$SO$_4$ and concentrated in vacuo. The obtained crude product was further purified by column chromatography using silica gel (230-400 mesh) eluting with 15% ethyl acetate in petroleum ether to get compound IXi as a pale brown solid. Yield: 0.5 g, 64.1%. LC_MS: Calc. for C$_{17}$H$_{22}$FNO$_4$ 323.36; Obs.: 324.1 [M+H]$^+$.

Step 10: 2-((7-Fluoro-1,4-dimethyl-2-oxo-1,2-dihydroquinolin-8-yl)oxy)acetaldehyde (IX)

To a stirred solution of compound IXi (0.5 g, 1.54 mmol) in dichloromethane (10 mL) at 0° C. under nitrogen atmosphere was added trifluoroacetic acid (5 mL, 10 volume) in dropwise. The resulting mixture was allowed to stir at room temperature for 2 hours. After that the reaction mixture was concentrated, basified with 10% NaHCO$_3$ solution, extracted with dichloromethane (3×50 mL). The combined organic extract was dried over anhydrous Na$_2$SO$_4$ and concentrated in vacuo to get compound IX (crude) as a brown solid, which was used for the next step without further purification. Yield: 0.25 g. LC_MS: Calc. for C$_{13}$H$_2$FNO$_3$ 249.24; Obs. 250.1 [M+H]+; $^1$H-NMR (300 MHz, DMSO-d$_6$): δ 9.67 (s, 1H), 7.60-7.55 (m, 1H), 7.29-7.22 (m, 1H), 6.53 (s, 1H), 4.88 (s, 2H), 3.79 (s, 3H), 2.49 (s, 3H).

Synthesis of 7-Fluoro-1-methyl-8-(2-oxopropoxy)quinolin-2(1H)-one (Intermediate X)

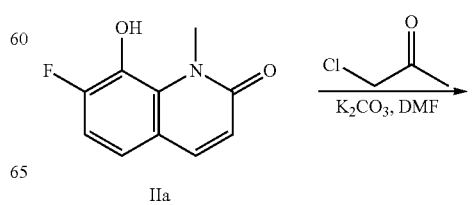

IIa

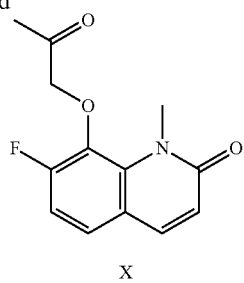

X

To a stirred solution of compound IIa (0.6 g, 3.10 mmol) in DMF (6 mL) at room temperature under nitrogen atmosphere were added potassium carbonate (0.65 g, 4.66 mmol) and chloroacetone (0.46 g, 4.96 mmol successively. The reaction mixture was then warmed to room temperature and stirred for 16 hours. After that the reaction mixture was diluted with water (20 mL) and extracted with ethyl acetate (3×25 mL). The combined organic phase was washed with brine solution, dried over $Na_2SO_4$ and concentrated in vacuo. The obtained crude product was further purified by column chromatography using silica gel (230-400 mesh) eluting with 10% ethyl acetate in petroleum ether to get compound X as a brown solid. Yield: 0.26 g, 33.76%. LC_MS: Calc. for $C_{13}H_{12}FNO_3$ 249.24; Obs.: 250.1 [M+H]$^+$.

Synthesis of 2-((6-fluoro-2,4-dimethyl-3-oxo-3,4-dihydroquinoxalin-5-yl)oxy)acetaldehyde, (Intermediate XI)

Step 1: 8-Bromo-7-fluoro-1, 3-dimethylquinoxalin-2(1H)-one (XIa)

To a stirred solution of compound VIIIc (3.00 g, 13.7 mmol) in ethanol (15 mL) at room temperature under nitrogen atmosphere were added ethyl pyruvate (1.52 mL, 13.7 mmol) and acetic acid (15 mL) successively. The resulting mixture was heated to reflux and stirred for 16 hours. After that, the reaction mixture was concentrated under reduced pressure. The residue obtained was diluted with water (100 mL) and extracted with ethyl acetate (2×50 mL). The combined organic phase was washed with brine (50 mL), dried over $Na_2SO_4$ and evaporated in vacuo. The obtained crude product was further purified by column chromatography using silica gel (230-400 mesh) eluting with 20-30% ethyl acetate in petroleum ether to get compound XIa as an off-white solid. Yield: 2.30 g, 61.99%; $^1$H-NMR (400 MHz, DMSO-d$_6$): δ 7.82-7.78 (m, 1H), 7.41-7.37 (m, 1H), 3.91 (s, 3H), 2.42 (s, 3H).

Step 2: 7-Fluoro-8-hydroxy-1,3-dimethylquinoxalin-2(1H)-one (XIb)

A stirred solution of compound XIa (2.1 g, 7.74 mmol) in a mixture of 1,4-dioxane (25 mL) and water (15 mL) at room temperature was degassed with a stream of nitrogen for 15 minutes. Then t-BuXPhos Palladacycle (0.18454 g, 0.234 mmol) and tris (dibenzylideneacetone)dipalladium (0) (0.141 g, 0.16 mmol) were added successively. The resulting mixture was again degassed with stream of nitrogen for 10 minutes. Then KOH (0.867 g, 15.48 mmol) was added to the reaction mixture under nitrogen atmosphere. The resulting mixture was then heated to 100° C. and stirred for 16 hours. After that the reaction mixture was cooled to 0° C., quenched with water and washed with ethyl acetate (2×50

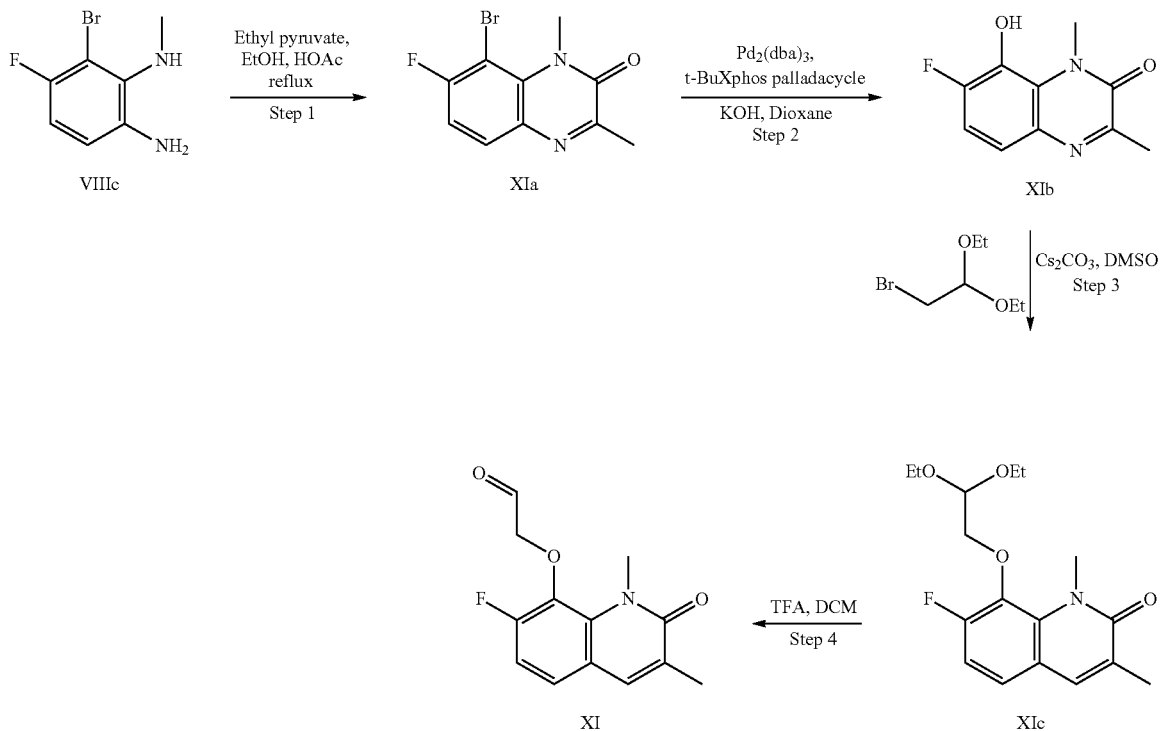

mL). The aqueous phase was then acidified with aqueous HCl (1.5 N, 5 mL) and extracted with ethyl acetate (3×50 mL). The combined organic phase was washed with brine solution (50 mL), dried over $Na_2SO_4$ and concentrated in vacuo to get compound XIb (crude) as a pale brown solid, which was taken for the next step without any further purification. Yield: 1.0 g, 62.5%. LC_MS: Calc. for $C_{10}H_9FN_2O_2$ 208.19; Obs.: 209.0 $[M+H]^+$.

Step 3: 8-(2,2-Diethoxyethoxy)-7-fluoro-1,3-dimethylquinoxalin-2(1H)-one (XIc)

To a stirred solution of compound XIb (1.0 g, 4.807 mmol) in dimethyl sulfoxide (10 mL) at room temperature under nitrogen atmosphere were added cesium carbonate (2.34 g, 7.21 mmol) and bromoacetaldehyde diethyl acetal (1.2 mL, 7.69 mmol successively. The resulting mixture was heated to 90° C. and stirred for 16 hours. After that the reaction mixture was diluted with water (20 mL) and extracted with ethyl acetate (3×25 mL). The combined organic phase was washed with brine solution, dried over $Na_2SO_4$ and concentrated in vacuo. The obtained crude product was further purified by column chromatography using silica gel (230-400 mesh) eluting with 15% ethyl acetate in petroleum ether to get compound XIc as a pale brown solid. Yield: 1.1 g, 73.33%. LC_MS: Calc. for $C_{16}H_{21}FN_2O_4$ 324.35; Obs.: 324.9 $[M+H]^+$.

Step 4: 2-((6-Fluoro-2,4-dimethyl-3-oxo-3,4-dihydroquinoxalin-5-yl)oxy)acetaldehyde (XI)

To a stirred solution of compound XIc (1.1 g, 3.39 mmol) in dichloromethane (15 mL) at 0° C. under nitrogen atmosphere was added trifluoroacetic acid (5.5 mL, 5 volume) in dropwise. The resulting mixture was allowed to stir at room temperature for 2 hours. After that the reaction mixture was concentrated, basified with 10% $NaHCO_3$ solution and extracted with dichloromethane (3×50 mL). The combined organic phase was dried over $Na_2SO_4$ and concentrated in vacuo to get compound XI (crude) as a brown solid, which was used as such for the next step without further purification. Yield: 0.4 g. LC_MS: Calc. for $C_{12}H_{11}FN_2O_3$ 250.23; Obs. 250.9 $[M+H]+$.

Synthesis of 2-((3-Chloro-5-methyl-6-oxo-5,6-dihydro-1,5-naphthyridin-4-yl)oxy)acetaldehyde, (Intermediate XII)

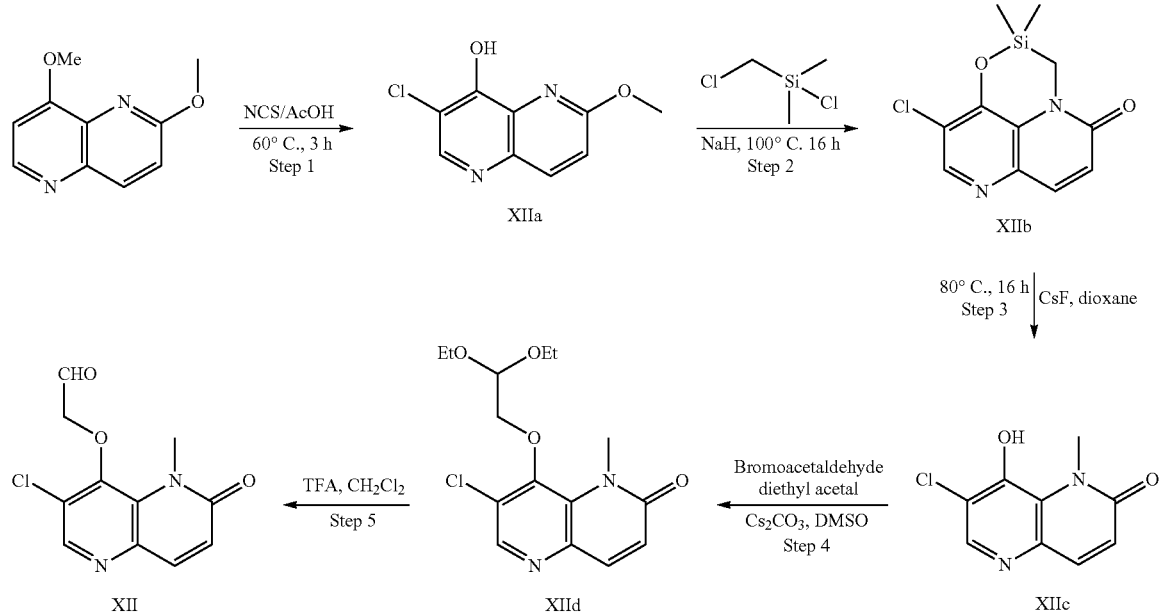

Step 1: 3-Chloro-6-methoxy-1,5-naphthyridin-4-ol (XIIa)

To a stirred solution of 6-methoxy-1,5-naphthyridin-4-ol (10.0 g, 56.76 mmol) in glacial acetic acid (150 mL) at room temperature under nitrogen atmosphere was added N-chlorosuccinimide (8.48 g, 63.57 mmol). The reaction mixture was heated to 60° C. and stirred for 3 hour. After that, the reaction mixture was cold to room temperature and solid precipitated was filtered, washed with n-hexane and dried under vacuo to get compound XIIa as a white solid, which was used as such for the next step without any further purification. Yield: 10.0 g (crude), 85.03%. LC_MS Calc. for $C_9H_7ClN_2O_2$, 210.62; Obs: 211.0 $[M^++H]$; $^1H$-NMR (300 MHz, DMSO-$d_6$): δ 8.40 (s, 1H) 7.99 (d, J=11.60 Hz, 1H), 7.20 (d, J=12.0 Hz, 1H), 3.95 (s, 3H), 3.33 (brs, 1H).

Step 2: 10-Chloro-2,2-dimethyl-2,3-dihydro-5H-[1,4,2]oxazasilino[6,5,4-de][1,5]naphthyridin-5-one (XIIb)

To a stirred solution of compound XIIa (2.0 g, 9.49 mmol) in DMF (60 mL) at 0° C. under nitrogen atmosphere was added sodium hydride (0.57 g, 14.24 mmol, 60% dispersed in mineral oil). The resulting mixture was warmed to room temperature and stirred for 1 hour. Then chloro (chloromethyl)dimethylsilane (2.02 mL, 15.19 mmol) was added to the reaction mixture at room temperature and allowed to stir for another 1.5 hour. The reaction mixture then heated to 100° C. and stirred for 16 hours. After that, the reaction mixture was quenched with methanol (1 mL) and concentrated completely in vacuo. The obtained crude product was triturated with diethyl ether, filtered and dried under vacuo to get compound XIIb as a pale orange solid, which was used as such for the next step without any purification. Yield: 3.0 g (crude). LC_MS Calc. for $C_{11}H_{11}ClN_2O_2Si$, 266.76; Obs: 266.8; $^1$H-NMR (400 MHz, DMSO-$d_6$): δ 8.45 (s, 1H) 7.88 (d, J=9.60 Hz, 1H), 6.89 (d, J=9.60 Hz, 1H), 3.62 (s, 2H), 0.47 (s, 6H).

Step 3: 7-Chloro-8-hydroxy-1-methyl-1,5-naphthyridin-2(1H)-one (XIIc)

To a stirred solution of compound XIIb (3.0 g, 11.27 mmol) in a mixture of 1,4-dioxane/methanol (113 mL, 2:1) at room temperature under nitrogen atmosphere was added cesium fluoride (5.13 g, 33.82 mmol). The reaction mixture was then heated to 80° C. and stirred for 16 hours. After that, the reaction mixture was concentrated in vacuo. The residue obtained was dissolved in water (5 mL) and neutralized with 1.5 N HCl (adjusted pH~6-7). The solid precipitated out was filtered and dried under vacuo to get compound XIIc as an off white solid, which was used as such for the next step without any purification. Yield: 2.0 g (crude). LC_MS Calc. for $C_9H_7ClN_2O_2$, 210.62; Obs.; 211.1; $[M^++H]$; $^1$H-NMR (400 MHz, DMSO-$d_6$): δ 12.53 (brs, 1H), 8.29 (s, 1H), 7.69 (d, J=9.20 Hz, 1H), 6.84 (d, J=9.60 Hz, 1H), 3.98 (s, 3H).

Step 4: 7-Chloro-8-(2,2-diethoxyethoxy)-1-methyl-1,5-naphthyridin-2(1H)-one (XIId)

To a stirred solution of compound XIIc (0.5 g, 2.37 mmol) in DMSO (5 mL) at room temperature under nitrogen atmosphere were added bromoacetaldehyde diethyl acetal (0.45 mL, 2.85 mmol) and cesium carbonate (1.16 g, 3.56 mmol) successively. Then the reaction mixture was heated to 100° C. and stirred for 16 hours. After that, the reaction mixture quenched with water and extracted with ethyl acetate (3×50 mL). The combined organic phase was washed with brine solution (50 mL), dried over anhydrous sodium sulfate and concentrated in vacuo. The obtained crude product was further purified by column chromatography using silica gel (60-120 mesh) eluting with 30% ethyl acetate in petroleum ether to get compound XIId as a brown solid. Yield: 0.3 g, 38.34%. LC_MS Calc. for $C_{15}H_{19}ClN_2O_4$, 326.78; Obs.; 327.1; $[M^++H]$; $^1$H-NMR (400 MHz, DMSO-$d_6$): δ 8.34 (s, 1H), 8.08 (d, J=10.00 Hz, 1H), 6.86 (d, J=10.40 Hz, 1H), 4.74 (s, 1H), 4.41 (d, J=4.80 Hz, 2H), 3.95 (s, 3H), 3.66-3.60 (m, 2H), 3.47-3.40 (m, 2H), 1.03-1.00 (m, 6H).

Step 5: 2-((3-Chloro-5-methyl-6-oxo-5,6-dihydro-1,5-naphthyridin-4-yl)oxy)acetaldehyde (XII)

To a stirred solution of compound 5 (0.3 g, 0.92 mmol) in dichloromethane (3 mL) at 0° C. under nitrogen atmosphere were added trifluoroacetic acid (3 mL). The resulting mixture was then warmed to room temperature and stirred for 3 hours. After that, the reaction mixture quenched with 10% NaHCO$_3$ solution and extracted with ethyl acetate (3×20 mL). The combined organic phase was washed with brine solution (20 mL), dried over anhydrous sodium sulfate and concentrated in vacuo to get compound 6 as a pale brown solid, which was used as such for the next step without any purification. Yield: 0.2 g (crude). LC_MS Calc. for $C_{11}H_9CN_2O_3$, 252.65; Obs: 250.8 $[M^+–H]$; $^1$H-NMR (300 MHz, DMSO-$d_6$): δ 9.62 (s, 1H), 8.28-8.24 (m, 1H) 8.02 (d, J=14.0 Hz, 1H), 6.86-6.82 (m, 1H), 4.20-4.02 (m, 2H), 3.93 (s, 3H)

Further, the compounds of Formula I were prepared utilizing the intermediates above.

Synthesis of (S)-6-(5-(((2-((5-methyl-6-oxo-5,6-dihydro-1,5-naphthyridin-4-yl)oxy)ethyl)amino)methyl)-2-oxoxazolidin-3-yl)-2H-pyrido[3,2-b][1,4]oxazin-3(4H)-one (Compound 1)

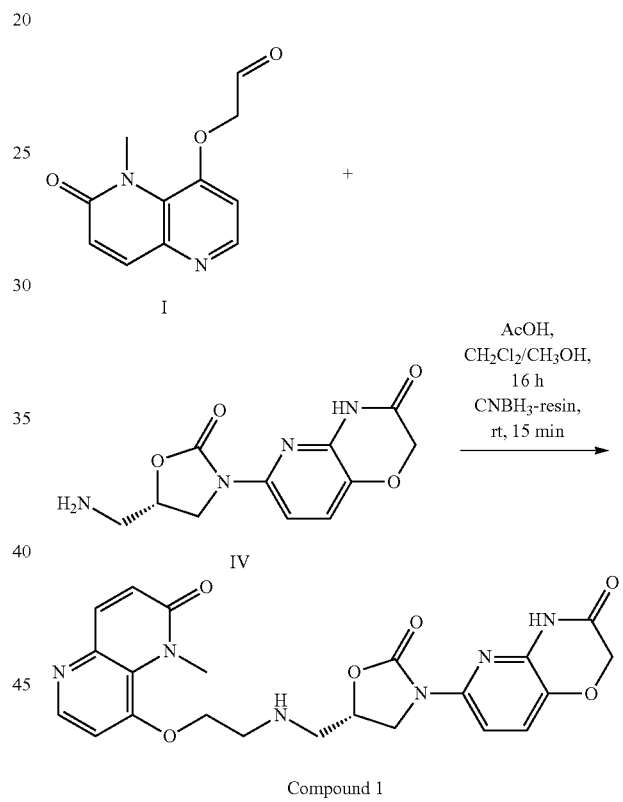

To a mixture of aldehyde, I (0.1 g, 0.45 mmol) and amine IV (0.12 g, 0.45 mmol) in dry methanol (10 mL) and dry dichloromethane (10 mL) was added AcOH (0.10 mL) and allowed to stir for 16 hours at room temperature. To this was added cyanoborohydride resin (0.34 g, 0.68 mmol) and stirred for another 15 minutes at room temperature. The reaction mixture was filtered, and the filtrate was concentrated to get the crude. The crude was purified by preparative HPLC to afford the pure product (Compound 1) as formate salt (off-white solid, 13 mg, 6%). LC-MS Calc. for $C_{22}H_{22}N_6O_6$: 466.45; Obs.: 467.2 $[M^++H]$; $^1$H NMR (400 MHz, DMSO-D$_6$): δ 11.16 (s, 1H), 8.34 (m, 1H), 7.83 (d, J=8.4 Hz, 1H), 7.57 (d, J=8.4, Hz, 1H), 7.38 (d, J=9 Hz, 1H), 7.21 (m, 1H), 6.82 (d, J=9.8 Hz, 1H), 4.76 (brs, 1H), 4.62 (s, 2H), 4.23 (m, 2H), 4.13-4.11 (m, 1H), 3.87 (m, 1H), 3.80 (s, 3H), 3.08 (m, 2H), 2.96 (m, 3H).

Synthesis of (S)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 2)

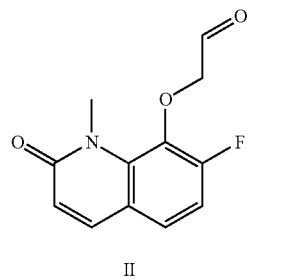

Synthesis of (R)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 3)

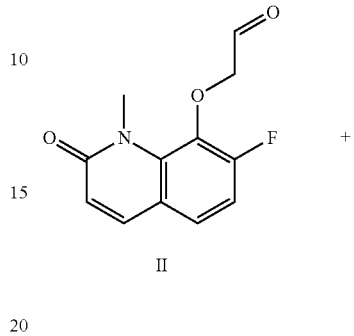

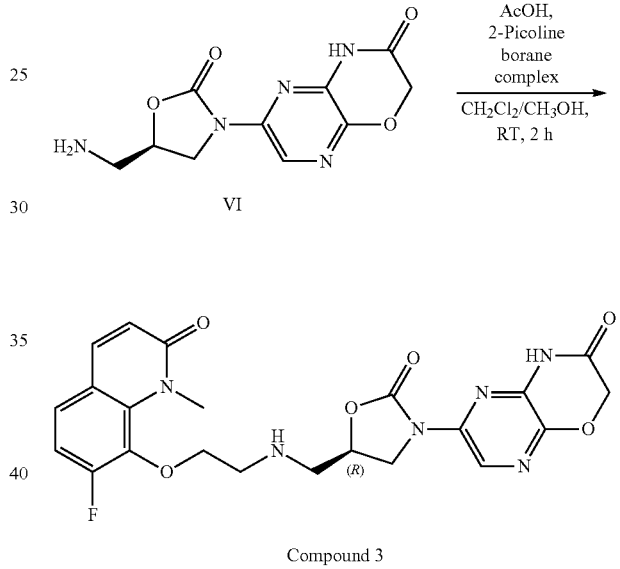

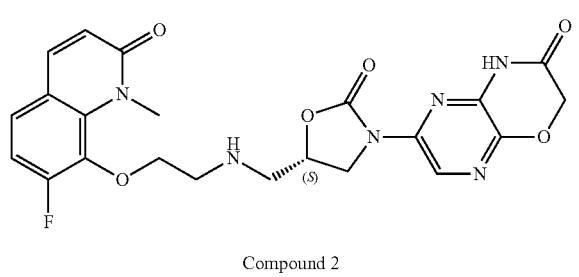

Compound 2

To a mixture of aldehyde I (0.2 g, 0.85 mmol) and amine VI (0.22 g, 0.85 mmol) in dry MeOH (10 mL) and DCM (10 mL) was added AcOH (0.25 mL) and allowed to stir for 16 h. To this was added cyanoborohydride resin (2.05 mmol %, 0.63 g, 1.27 mmol) and stirred for 5 min. The reaction mixture was filtered, and the filtrate was concentrated to get the crude product. The crude was purified by reverse phase preparative HPLC method to afford the Compound 2 as off-white solid (Formate salt, 50 mg). LC-MS Calc. for $C_{22}H_{21}FN_6O_6$: 484.44; Obs.: 485.1; [M$^+$+H]; $^1$H NMR (400 MHz, DMSO-D$_6$): δ 8.39 (s, 1H), 8.23 (s, 1H), 7.85 (d, J=9.44 Hz, 1H), 7.49-7.50 (m, 1H), 7.22 (t, J=10.08 Hz, 1H), 6.56 (d, J=9.36 Hz, 1H), 4.79-4.81 (m, 3H), 4.03-4.04 (m, 3H), 3.83-3.85 (m, 5H), 2.93-2.94 (m, 4H).

To a mixture of compound H (0.5 g, 1.88 mmol) and compound VI (0.443 g, 1.88 mmol) in a mixture of dry MeOH (20 mL) and CH$_2$Cl$_2$ (20 mL) at room temperature under nitrogen atmosphere were added AcOH (0.5 mL) followed by 2-picoline borane complex (2.05 mmol %) (0.120 g, 1.13 mmol). The reaction mixture was continued to stir at room temperature for 1 hour. The reaction mixture was quenched with 1% HCOOH in water and concentrated in vacuo to get the crude. The obtained crude was purified by column chromatography by eluting with 8-10% methanol in dichloromethane. The pure product obtained was further triturated with diethyl ether to afford Compound 3 as an off-white solid (Formate salt). Yield: 0.2 g, 21.95%. LC-MS Calc. for $C_{22}H_{21}FN_6O_6$: 484.44; Obs.: 485.1; [M$^+$+H]; $^1$H NMR (400 MHz, DMSO-d$_6$): δ 11.63 (S, 1H), 8.39 (s, 1H), 8.14 (s, 1H), 7.87 (d, J=9.44 Hz, 1H), 7.54-7.51 (m, 1H), 7.24 (t, J=10.08 Hz, 1H), 6.57 (d, J=9.20 Hz, 1H), 4.86-4.81 (m, 3H), 4.17-4.11 (m, 3H), 3.88-3.83 (m, 4H), 3.33-3.11 (m, 4H). HPLC Purity=96.21%, Column: X-Bridge C8 (50×4.6) mm, 3.5 μm, Mobile Phase A: 0.1% TFA in water, Mobile Phase B: 0.1% TFA in acetonitrile.

Synthesis of 6-((5S)-5-(((1-((7-fluoro-1-methyl-2-oxo-1,2-dihydroquinolin-8-yl)oxy)propan-2-yl)amino)methyl)-2-oxooxazolidin-3-yl)-2H-pyrazino[2,3-b][1,4]oxazin-3(4H)-one (Compound 4)

Synthesis of (S)-6-(5-(((2-((7-fluoro-1,4-dimethyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 5)

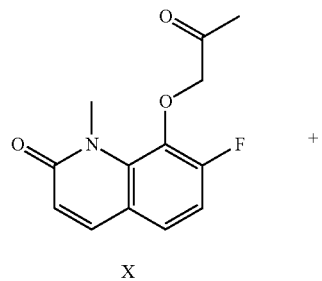

X

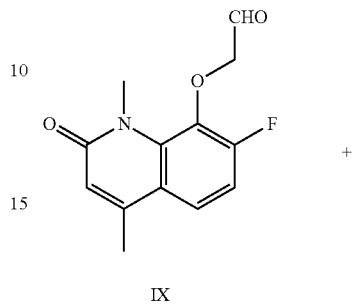

IX

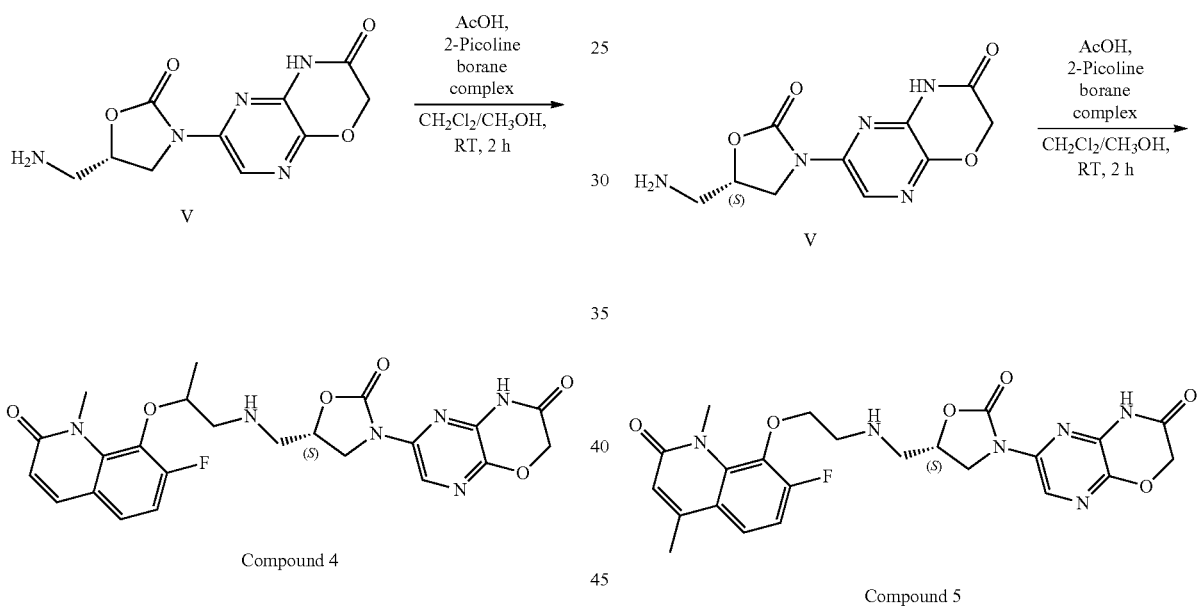

Compound 4

Compound 5

To a stirred mixture of compound X (260 mg, 1.0 mmol) and compound V (275 mg, 1.0 mmol) in a mixture of dry MeOH/dichloromethane (30 mL, 1:1) at room temperature under nitrogen atmosphere were added AcOH (0.6 mL) and 2-picoline-borane complex (110 mg, 1.0 mmol) successively. The reaction mixture was continued to stir at room temperature for 16 hours. After that, the reaction mixture was quenched with 0.1% HCOOH in water and concentrated under reduced pressure. The obtained crude product was further purified by PREP HPLC to get Compound 4 as an off-white solid. Yield: 100 mg, 50.20%. LC_MS Calc. for $C_{23}H_{23}FN_6O_6$, 498.47; Obs.: 499.1 [M$^+$+H]. $^1$H-NMR (300 MHz, DMSO-d$_6$): δ 11.60 (brs, 1H), 8.38-8.35 (m, 1H), 7.85-7.82 (d, J=9.3 Hz, 1H), 7.52-7.47 (t, J=6.6 Hz, 1H), 7.24-7.18 (t, J=9.3 Hz, 1H), 6.57-6.53 (d, J=9.3 Hz, 1H), 4.84 (brs, 3H), 4.15-4.09 (m, 1H), 3.95-3.85 (m, 2H), 3.80 (s, 3H), 3.19-3.04 (m, 4H), 1.17-1.14 (d, 3H); HPLC Purity=99.25% (HPLC Column: XBridge C8 (50×4.6) mm, 3.5 μm, Mobile Phase A: 0.1% TFA in water, Mobile Phase B: 0.1% TFA in Acetonitrile.

To a stirred mixture of compound IX (250 mg, 1.00 mmol) and compound V (280 mg, 1.00 mmol) in a mixture of dry MeOH/dichloromethane (20 mL, 1:1) at room temperature under nitrogen atmosphere were added AcOH (0.5 mL) and 2-picoline-borane complex (64 mg, 0.6024 mmol) successively. The reaction mixture was continued stirred at room temperature for 1 hour. After that, the reaction mixture was quenched with 0.1% HCOOH in water and concentrated under reduced pressure. The obtained crude product was further purified by PREP HPLC to get Compound 5 as an off-white solid. Yield: 50 mg, 10.0%. LC_MS Calc. for $C_{24}H_{25}FN_6O_6$, 512.50; Obs.: 513.1 [M$^+$+H]; $^1$H-NMR (400 MHz, DMSO-d$_6$): δ 11.65 (brs, 1H), 8.39 (s, 1H), 7.62-7.58 (m, 1H), 7.31-7.26 (t, J=10.0 Hz, 1H), 6.54 (d, J=5.2 Hz, 1H), 4.87-4.83 (m, 3H), 4.24-4.17 (m, 2H), 3.83 (s, 3H), 3.78-3.74 (m, 1H), 2.98 (brs, 2H), 2.50 (s, 3H), 2.06 (brs, 2H); HPLC Purity=96.24% (HPLC Column: Atlantis dC18 (250*4.6) mm 5 μm, Mobile Phase A: 0.1% TFA in water, Mobile Phase B: Acetonitrile.

Synthesis of (S)-6-(5-(((2-((3-chloro-5-methyl-6-oxo-5,6-dihydro-1,5-naphthyridin-4-yl)oxy)ethyl)amino)methyl)-2-oxooxazolidin-3-yl)-2H-pyrazino[2,3-b][1,4]oxazin-3(4H)-one (Compound 6)

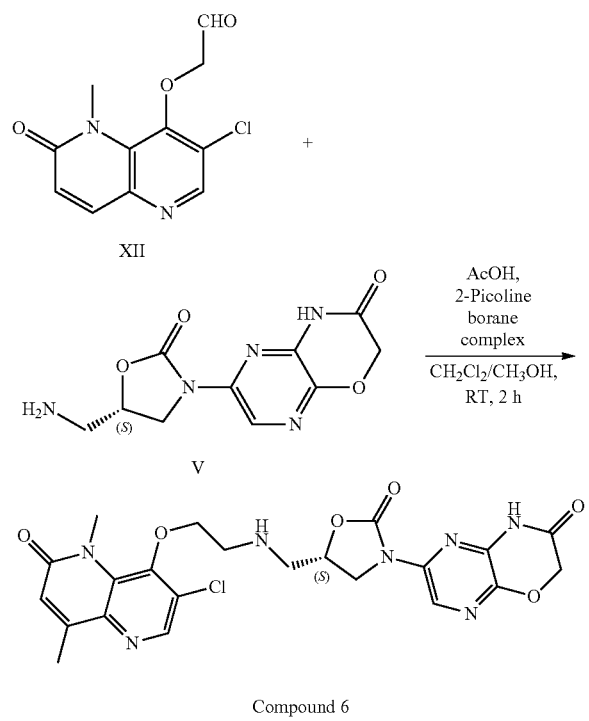

To a stirred solution of compound XII (0.2 g, 0.79 mmol) and compound V (0.232 g, 0.87 mmol) in a mixture of dry MeOH/dichloromethane (8 mL, 1:1) at room temperature under nitrogen atmosphere was added AcOH (0.2 mL) and allowed to stir for 10 mins. Then 2-picoline borane complex (0.051 g, 0.477 mmol) was added at 0° C. The reaction mixture was then warmed to room temperature and stirred for 3 hours. After that the reaction mixture was quenched with 1% formic acid in water and concentrated in vacuo. The obtained crude product was further purified by PREP HPLC (reverse phase) to get Compound 6 as a white solid (Formate salt). Yield: 0.010 g. LC_MS Calc. for $C_{21}H_{20}ClN_7O_6$, 501.88; Obs.: 502.2 [M+H]+.

Synthesis of ((S)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 7)

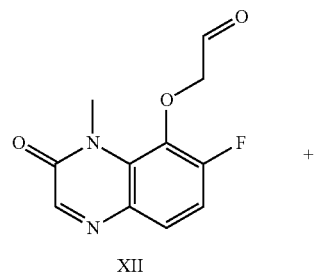

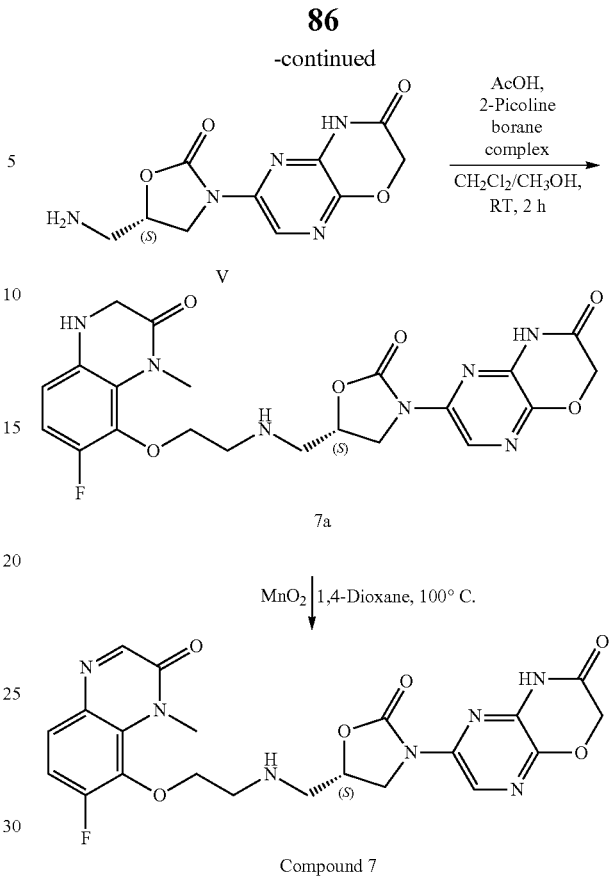

To a stirred solution of compound VII (0.15 g, 0.635 mmol) and compound V (0.17 g, 0.635 mmol) in a mixture of dry methanol/dichloromethane (40 mL, 1:1) at room temperature under nitrogen atmosphere were added AcOH (0.3 mL) and Pic-BH$_3$ (32 mg, 0.38 mmol). The resulting mixture was continued to stir at room temperature for 1 hour. The progress of the reaction was monitored by TLC. After that the reaction mixture was quenched with water (3 mL) and concentrated under reduced pressure. The obtained crude product was further purified by column chromatography using silica gel (230-400 mesh) eluting with 5% Methanol in DCM to get compound 7a as a brown solid. Yield: 0.12 g, 38.7%. LC_MS: Calc. for $C_{21}H_{22}FN_7O_6$ 487.45; Obs.: 486.3 [M−H]+.

To a stirred solution of compound 7a (0.12 g, 0.2462 mmol) in 1, 4-dioxane (4 mL) at room temperature under nitrogen atmosphere was added MnO$_2$ (12 mg, 0.1478 mmol) at once. The resulting mixture was heated to 100° C. and stirred for 2 hours. After that the reaction mixture was cooled to room temperature, filtered through celite pad and thoroughly washed with ethyl acetate and DCM (1:1). The combined filtrate was concentrated under reduced pressure to get crude compound as a pale brown solid, which was further purified by PREP HPLC to get compound Compound 7 as trifluoro acetic acid salt: Off white amorphous powder; Yield: 50 mg, 420%.

LC_MS: Calc. for $C_{21}H_2OFN_7O_6$ 485.43; Obs.: 486.1 [M+H]+; $^1$H-NMR (400 MHz, DMSO-d$_6$): δ 11.68 (s, 1H), 9.32 (bs, 2H), 8.40 (s, 1H), 8.23 (s, 1H), 7.71-7.68 (m, 1H), 7.44-7.39 (t, J=9.32 Hz, 1H), 5.13 (bs, 1H), 4.89 (s, 2H), 4.35-4.34 (m, 2H), 4.26-4.24 (m, 1H), 3.86 (s, 3H), 3.84-3.82 (m, 1H), 3.55-3.51 (m, 4H). LC_MS: Calc. for $C_{21}H_2OFN_7O_6$ 485.43; Obs.: 486.1 [M+H]+; HPLC: 1.95 min; 98.77%; HPLC Column: X-Bridge C8 (50×4.6) mm, 3.5 μm, Mobile Phase A: 0.1% TFA in H₂O, Mobile Phase B: Acetonitrile.

Synthesis of ((R)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 8)

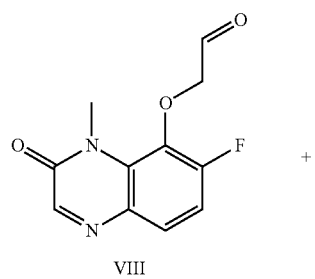

VIII

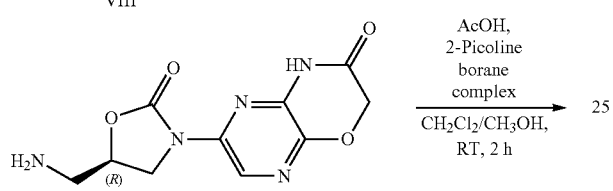

VI

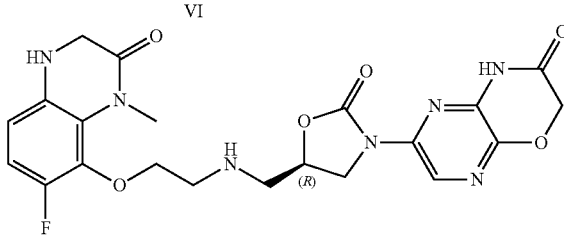

8a

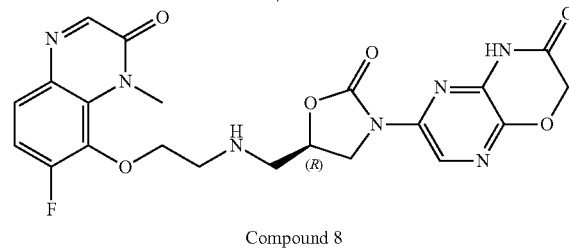

Compound 8

To a stirred solution of compound VIII (0.250 g, 1.06 mmol) and compound VI (0.280 g, 1.06 mmol) in a mixture of dry MeOH/dichloromethane (20 mL, 1:1) at room temperature under nitrogen atmosphere was added AcOH (0.5 mL) and allowed to stir for 10 mins. The reaction mixture was cold to 0° C. and was added 2-picoline borane complex (0.067 g, 0.63 mmol). The reaction mixture was then warmed to room temperature and stirred for 3 hours. After that the reaction mixture was quenched with water and concentrated in vacuo. The obtained crude product was purified by column chromatography using silica gel (60-120 mesh) eluting with 4% of methanol in dichloromethane to get compound 8a. Yield: 0.150 g, 30.91%; LC_MS Calc. for C₂₁H₂₂FN₇O₆, 487.45; Obs.: 487.8 [M⁺+H].

To a stirred solution of compound 8a (0.150 g, 0.307 mmol) in 1, 4-dioxane (3 mL) at room temperature under nitrogen atmosphere was added MnO₂ (0.192 g, 2.15 mmol). The reaction mixture was then heated to 100° C. and stirred for 2 hours. After that, the reaction mixture was filtered through celite, washed with dichloromethane/methanol (100 mL, 1:1) and concentrated in vacuo. The obtained crude product was purified by PRPE HPLC (reverse phase) to get Compound 8 as formate salt; White amorphous powder; Yield: 0.020 g, 13.29%.

LC_MS Calc. for C₂₁H₂₀FN₇O₆, 485.43; Obs.: 483.9 [M⁺−H]; ¹H-NMR (400 MHz, DMSO-d₆): δ 8.36 (s, 2H), 8.15 (s, 1H), 7.61-7.58 (m, 1H), 7.34-7.30 (m, 1H), 4.84 (s, 2H), 4.81-4.78 (m, 1H), 4.12-4.4.07 (m, 3H), 3.86-3.82 (m, 4H), 3.00-2.97 (m, 2H), 2.94-2.89 (m, 2H). HPLC Purity=91.42%, Column: X-Bridge C8 (50×4.6) mm, 3.5 μm, Mobile Phase A: 0.1% TFA in water, Mobile Phase B: Acetonitrile.

Synthesis of (S)-6-(5-(((2-((6-fluoro-2,4-dimethyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 9)

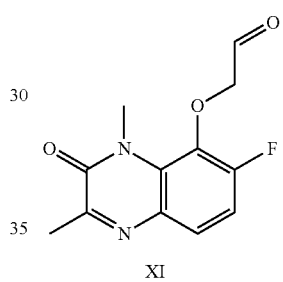

XI

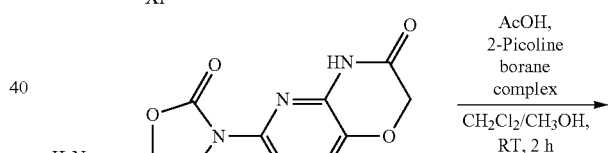

V

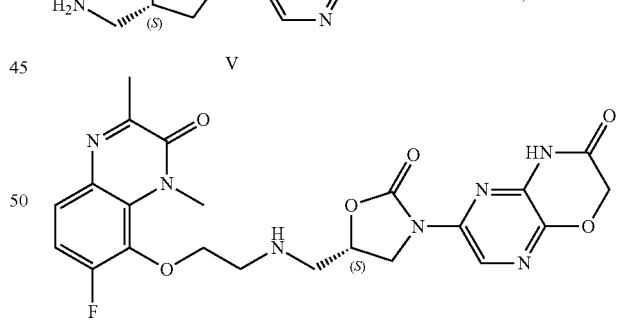

Compound 9

To a stirred mixture of compound XI (0.2 g, 0.8 mmol) and compound V (210 mg, 0.8 mmol) in a mixture of dry MeOH/dichloromethane (30 mL, 1:1) at room temperature under nitrogen atmosphere were added AcOH (0.4 mL) and 2-picoline-borane complex (51 mg, 0.48 mmol). The reaction mixture was continued to stir at room temperature for 1 hour. After that, the reaction mixture was quenched with 0.1% HCOOH in water and concentrated under reduced pressure. The obtained crude product was further purified by PREP HPLC to get Compound 9 as an off-white solid as a trifluoro acetic acid salt. Yield: 50 mg, 12.82%. LC_MS Calc. for $C_{22}H_{22}FN_7O_6$, 499.46; Obs.: 500.0 [M$^+$+H]; $^1$H NMR (400 MHz, DMSO-d$_6$): δ 11.69 (brs, 1H), 9.32 (brs, 2H), 8.40 (s, 1H) 7.62-7.58 (m, 1H), 7.39-7.34 (m, 1H), 5.16-5.12 (m, 1H), 4.89 (s, 2H), 4.36-4.24 (m, 2H), 3.87 (s, 3H), 3.85-3.83 (m, 2H), 3.57-3.52 (m, 4H), 2.33 (s, 3H); HPLC Purity=97.03% (HPLC Column: X-Bridge C8(50× 4.6) mm, 3.51 μm, Mobile Phase A: 0.1% TFA in water, Mobile Phase B: Acetonitrile.

Synthesis of (S)-5-(((2-((6-fluoro-4-methyl-3-oxo-3,4-dihydroquinoxalin-5-yl)oxy)ethyl)amino)methyl)-3-(3-oxo-3,4-dihydro-2H-pyrazino[2,3-b][1,4]thiazin-6-yl)oxazolidin-2-one (Compound 10)

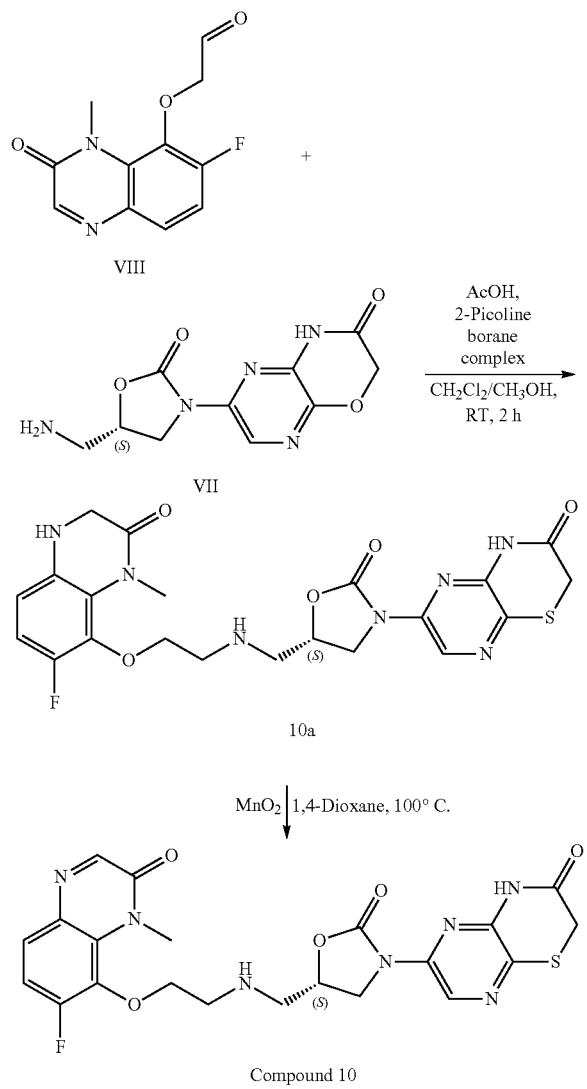

To a stirred solution of compound VIII (0.150 g, 0.63 mmol) and compound VII (0.179 g, 0.63 mmol) in a mixture of dry MeOH/dichloromethane (12 mL, 1:1) at room temperature under nitrogen atmosphere was added AcOH (0.3 mL) and allowed to stir for 10 mins. Then 2-picoline borane complex (0.040 g, 0.38 mmol) was added at 0° C. The resulting mixture was warmed to room temperature and stirred for 3 hours. After that the reaction mixture was quenched with water and concentrated in vacuo. The obtained crude product was purified by column chromatography using silica gel (60-120 mesh) eluting with 5% of methanol in dichloromethane to get compound 10a. Yield: 0.1 g, 31.65%; LC_MS Calc. for $C_{21}H_{22}FN_7O_5S$ 503.51; Obs.: 504.1 [M$^+$+H]$^+$.

To a stirred solution of compound 10a (0.1 g, 0.198 mmol) in 1, 4-dioxane (2 mL) at room temperature under nitrogen atmosphere was added manganese dioxide (0.124 g, 1.39 mmol). The reaction mixture was then heated to 100° C. and stirred for 2 hours. After that, the reaction mixture was filtered through celite pad, washed with dichloromethane/methanol (1:1, 100 mL) and concentrated in vacuo. The obtained crude product was purified further by PRPE HPLC (reverse phase) to get Compound 10 as formate salt. White amorphous powder: Yield: 0.020 g, 20.14%. LC_MS Calc. for $C_{21}H_{20}FN_7O_5S$ 501.49; Obs.: 499.8 [M$^+$–H]; $^1$H NMR (400 MHz, DMSO-d$_6$): δ 11.96 (brs, 1H), 8.78 (s, 1H), 8.30 (bs, 1H), 8.15 (s, 1H), 7.61-7.57 (m, 1H), 7.34-7.29 (m, 1H), 4.84-4.80 (m, 1H), 4.12-4.4.07 (m, 3H), 3.86-3.82 (m, 4H), 3.76 (s, 2H), 2.98-2.91 (m, 4H); HPLC Purity=99.55%, Column: X-Bridge C8 (50×4.6) mm, 3.5 μm, Mobile Phase A: 0.1% TFA in water, Mobile Phase B: Acetonitrile.

Example 3

Biological Activity

Antibacterial Activity:

The compounds of Formula I are of interest due to their potent antibacterial effects. The ability of the compounds of the present disclosure as disclosed herein, to achieve an antibacterial effect may be evaluated with regards to their ability to inhibit the growth of bacterial species like *Escherichia coli* ATCC 25922, *Staphylococcus aureus* ATCC 29213, *Klebsiella pneumoniae* ATCC 13883, *Acinetobacter baumannii* ATCC 19606, *Pseudomonas aeruginosa* ATCC 27853, *Enterococcus faecalis* ATCC 29212, *Enterococcus faecalis* ATCC 29212, *Proteus mirabilis* ATCC 43071, *Enterobacter cloacae* ATCC 13047, *Citrobacter freundii* ATCC 43864 and *Morganella morganii* ATCC 25830 using an assay based on the following Minimum Inhibitory Concentration (MIC) protocol.

The test bacteria were grown in Luria Bertani Broth (HIMEDIA M1245), 25 grams of the powder was dissolved in 1000 ml distilled water and sterilized by autoclaving at 15 lbs pressure (121° C.) for 20 minutes. The medium sterility was checked by incubating at 37° C. for a period of 48 h.

Bacterial cultures that were stored as glycerol stocks at −80° C. were sub cultured on LB agar plates to obtain isolated colonies. A single colony of each strain was cultured in LB broth. The cultures were incubated at 37° C., 200 rpm till they reach an optical density (OD at 600 nm) of 0.8 to 1. This log phase culture was diluted in LB broth to a cell number of 5-8×10^5 CFU/mL to be used as inoculum for MIC experiments. Test compounds were dissolved in dimethyl sulfoxide (DMSO) to a stock concentration of 4 mg/ml. A two-fold dilution series of this DMSO stock was prepared in a 96 well V bottom microtitre plate from rows A to H. A 3 μL volume of these dilutions were transferred to a 96-well flat bottom microtitre assay plate. Controls to monitor the effects of DMSO and media sterility were included. Each well was inoculated with 150 μL of the above diluted culture. The plates were incubated at 37° C. overnight in a humidified incubator. The following morning, the plates were read using a Spectrophotometer at 600 nM wavelength.

Minimum Inhibitory Concentration (MIC) is defined as the lowest drug concentration containing well that shows 90% inhibition of bacterial growth. The antibacterial activity (MIC) determined against representative Gram-positive (*Staphylococcus aureus* ATCC 29213, *Enterococcus faecalis* ATCC 29212) and Gram-negative (*Escherichia coli* ATCC25922, *Klebsiella pneumoniae* ATCC 13883, *Acinetobacter baumannii* ATCC 19606, *Pseudomonas aeruginosa* ATCC 27853, *Proteus mirabilis* ATCC 43071, *Enterobacter cloacae* ATCC 13047, *Citrobacter freundii* ATCC 43864, *Morganella morganii* ATCC 25830) pathogen were reported in Table 1. The exemplified compounds belonging to Formula I demonstrated potent antibacterial activity both Gram-positive and Gram-negative pathogens.

spermidine, 4 mM $MgCl_2$, 2 mM DTT, 6.5% (w/v) glycerol, 0.1 mg/mL BSA, and 1 mM ATP. The reaction was then stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH 8, 1 mM EDTA, 0.5 mg/ml Bromophenol Blue) and the supercoiled/relaxed forms of plasmid DNA were separated by agarose gel electrophoresis. The 1% agarose gels were run for 3 h at 4 V/cm in 1×TAE (40 mM Tris, 20 mM acetic acid, 1 mM EDTA). To visualize the DNA the gels were stained for 10 min with 0.7 µg/mL ethidium bromide and excess dye was removed by several washes with water. $IC_{50}$ values were determined by quantifying the supercoiled and relaxed DNA

TABLE 1

MIC studies in LB Media

| | Minimum Inhibitory Concentration (µg/mL) in LB Media | | | | | | | | | |
|---|---|---|---|---|---|---|---|---|---|---|
| Compound | S. au | E. fa | E. co | P. ae | K. pn | A. ba | C. fr | E. cl | M. mo | P. mi |
| 1 | 0.25 | 1 | 0.5 | 4 | 1 | 2 | 1 | 8 | 2 | 16 |
| 2 | ≤0.015 | 0.06 | 0.03 | 0.5 | 0.06 | 0.06 | ≤0.03 | 0.125 | 0.125 | 0.125 |
| 3 | 0.015 | 0.06 | 0.06 | 0.5 | 0.06 | 0.06 | 0.06 | 0.125 | 0.03 | 0.125 |
| 4 | 0.06 | 0.125 | 0.25 | 2 | 0.25 | 0.25 | 0.5 | 0.5 | 1 | 2 |
| 5 | 0.125 | 0.125 | 0.06 | 1 | 0.25 | 0.25 | ND | ND | ND | ND |
| 6 | >4 | >4 | >4 | >4 | >4 | >4 | >4 | >4 | >4 | >4 |
| 7 | ≤0.015 | 0.06 | 0.03 | 0.25 | 0.06 | 0.06 | 0.06 | 0.125 | 0.06 | 0.25 |
| 8 | ≤0.015 | 0.06 | 0.03 | 0.5 | 0.06 | 0.06 | 0.06 | 0.125 | 0.03 | 0.25 |
| 9 | ≤0.06 | 0.25 | 0.125 | 4 | 0.5 | 0.125 | 0.25 | 1 | 0.5 | 2 |
| 10 | ≤0.003 | 0.025 | 0.025 | 0.25 | 0.025 | 0.013 | 0.025 | 0.05 | 0.025 | 0.125 |
| Cifrofloxacin | 0.4 | 0.4 | 0.012 | 0.1 | 0.05 | 0.4 | ≤0.006 | 0.0125 | ≤0.006 | 0.025 |

S. au: S. aureus ATCC 29213;
E. fa: E. faecalis ATCC 29212;
E. co: E. coli ATCC 25922;
P. ae: P. aurigenosa ATCC 27853;
K. pn: K. pneumoniae ATCC 13883;
A. ba: A. baumannii ATCC 19606;
C. fr: Citrobacter freundii ATCC 43864;
E. cl: Enterobacter cloacae ATCC 13047;
M. mo: Morganella morganii ATCC 25830;
P. mi; Proteus mirabilis ATCC 43071

Enzyme Inhibition Assay: Determination $IC_{50}$ Value Against *E. coli* Gyrase Supercoiling and *E. coli* Topo IV Decatenation The compounds of Formula I or its stereoisomers, pharmaceutically acceptable salts, complexes, hydrates, solvates, tautomers, polymorphs, racemic mixtures, optically active forms and pharmaceutically active derivative thereof, were evaluated for use in killing or inhibiting the growth of Gram-positive and Gram-negative bacteria through inhibition of bacterial Type II topoisomerases namely, DNA gyrase and Topo IV. The present disclosure also provides evidence for treating infection caused both Gram-positive and Gram-negative bacteria through the inhibition of bacterial topoisomerases using *E. coli*, DNA gyrase and Topo IV enzymes.

Procedure for *E. coli* DNA Gyrase Supercoiling Assay

*E. coli* gyrase supercoiling and its inhibition was assayed using a kit procured from Inpiralis ($K_{0001}$) and the protocol (PMID: 2172086) was adapted with necessary modifications. The compounds to be tested were incubated for 10 min with 2.5 nM of *E. coli* DNA gyrase in a 30 µl volume reaction and 3.2% DMSO. The reactions were then started with the addition of 60 ng relaxed pBR322 plasmid DNA and continued for 45 min at 37° C. The reaction mixture contained 35 mM Tris.HCl (pH 7.5), 24 mM KCl, 1.8 mM in each of the reactions from a gel image by a densitometric method using the Quantity One Software (Bio-rad).

Procedure for *E. coli* Topoisomerase IV Decatenation Assay

*E. coli* topoisomerase IV decatenation activity and its inhibition was assayed using a kit procured from Inpiralis (D4002) and the kit protocol was adapted with necessary modifications similar to the gyrase supercoiling assays. The compounds to be tested were incubated for 10 minutes with 5 nM of *E. coli* topoisomerase IV in a 30 µl volume reaction and 3.2% DMSO. The reactions were started with the addition of 60 ng of kDNA and continued for 40 min at 37° C. The final reaction mixture contains 40 mM Tris-HCl (pH 7.6), 100 mM potassium glutamate, 10 mM magnesium acetate, 10 mM DTT, 1 mM ATP, and 50 µg/ml albumin. The reactions were stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH 8, 1 mM EDTA, 0.5 mg/ml Bromophenol Blue) and the kDNA/minicircles forms were separated by agarose gel electrophoresis. The 1% agarose gels were run for 3 h at 4V/cm in 1×TAE (40 mM Tris, 20 mM acetic acid, 1 mM EDTA). To visualize the DNA, the gels were stained for 10 min with 0.7 µg/mL ethidium bromide and excess dye was removed by several washes with water. $IC_{50S}$ were determined by quantifying the Kinetoplast DNA (kDNA) band inside the gel well and decatenated minicircles that migrate into the gel in each of the reactions from a gel image by a densitometric method using the Quantity One Software (Bio-rad).

Representing compounds of Formula I were evaluated against of E. coli DNA gyrase and Topo IV enzyme using gel based supercoiling assay for gyrase inhibition and decatenation assay for Topo IV inhibition. The results of bacterial Type II Topo isomerases (Gyrase and Topo IV) have been presented in the Table 2 below.

The results presented in the Table 2 indicate that the compounds of Formula I exerts antibacterial activity through inhibition bacterial type II topoisomerase activity and signifies the dual mode of bacterial topoisomerases (Gyrase and Topo IV) inhibition for observed antibacterial activity of the compounds.

TABLE 2

Evaluation of compounds of Formula I against of E. coli DNA gyrase and Topo IV enzyme

| Compound | E. coli DNA Gyrase IC50 ($\mu$M) | E. coli Topo IV IC50 ($\mu$M) |
|---|---|---|
| 1 | <0.250 | <0.250 |
| 2 | 0.012 | 0.045 |
| 3 | 0.011 | ND |
| 4 | 0.03 | <0.350 |
| 5 | 0.033 | <0.187 |
| 6 | 6.33 | 17.70 |
| 7 | 0.015 | <0.220 |
| 9 | 0.04 | ND |
| 10 | 0.022 | <0.370 |
| Ciprofloxacin | 0.233 | 14.4 |

The $IC_{50}$ values for majority of the compounds belonging to Formula I was found to be ≤0.250 for both E. coli DNA Gyrase and E. coli Topo IV. On the other hand, $IC_{50}$ values for Compound 2 was found to be ≤0.05 for both the enzymes. This denotes that compounds of Formula I exert their antibacterial activity through inhibition of bacterial topoisomerases (Gyrase and Topo IV enzymes) inside the bacterial cell.

In order to test the ability of compounds to retain the antibacterial activity against clinical strains of bacteria, antibacterial susceptibility studies ($MIC_{50}$ and $MIC_{90}$ determination) were carried for a representative compound (Compound 2) from the series using clinical strains of five Gram-negative bacterial species (E. coli, P. aurigenosa, K. pneumoniae, A. baumanni, E. cloacae) according the standard CLSI guidelines and the results are presented Table 3 below. The standard drugs ciprofloxacin and meropenem were used as positive controls in the study.

TABLE 3

Susceptibility ($MIC_{50}$ and $MIC_{90}$ determination) studies

| E. coli | Ciprofloxacin | Meropenem | Compound 2 |
|---|---|---|---|
| Number of strain | 201 | 201 | 176 |
| ATCC25922 | 0.015 | 0.06 | 0.03 |
| Minimum | 0.015 | 0.03 | 0.03 |
| $MIC_{50}$ ($\mu$g/ml) | 16 | 0.06 | 0.25 |
| $MIC_{90}$ ($\mu$g/ml) | 16 | 4 | 0.25 |

| Aba | Ciprofloxacin | Meropenem | Compound 2 |
|---|---|---|---|
| Number of strain | 169 | 169 | 132 |
| ATCC19606 | 0.5 | 0.5 | 0.06 |
| Minimum | 0.06 | 0.03125 | 0.03 |
| $MIC_{50}$ ($\mu$g/ml) | 16 | 8 | 0.06 |
| $MIC_{90}$ ($\mu$g/ml) | 16 | 32 | 0.25 |

| Kpn | Ciprofloxacin | Meropenem | Compound 2 |
|---|---|---|---|
| Number of strain | 211 | 211 | 88 |
| ATCC13883 | 0.03 | 0.06 | 0.06 |
| Minimum | 0.015 | 0.03 | 0.06 |
| $MIC_{50}$ ($\mu$g/ml) | 4 | 1 | 0.125 |
| $MIC_{90}$ ($\mu$g/ml) | 16 | 16 | 0.5 |

| Pae | Ciprofloxacin | Meropenem | Compound 2 |
|---|---|---|---|
| Number of strain | 215 | 215 | 176 |
| ATCC27853 | 0.25 | 0.5 | 0.5 |
| Minimum | 0.015 | 0.03 | 0.031 |
| $MIC_{50}$ ($\mu$g/ml) | 0.125 | 2 | 1 |
| $MIC_{90}$ ($\mu$g/ml) | 16 | 8 | 1 |

| E. cloacae | Ciprofloxacin | Meropenem | Compound 2 |
|---|---|---|---|
| Number of strain | 88 | 88 | 88 |
| Minimum | 0.06 | 0.06 | 0.03 |
| $MIC_{50}$ ($\mu$g/ml) | 0.06 | 0.25 | 0.125 |
| $MIC_{90}$ ($\mu$g/ml) | 16 | 16 | 0.25 |

The antibacterial susceptibility studies illustrated in the Table 3 indicates that compounds of Formula I work against both drug sensitive and resistant clinical strains of gram-negative bacterial species and retain the antibacterial activity. The $MIC_{90}$ values of Compound 2 are 0.25 to 1 $\mu$g/ml range for 5 bacterial species and it is found to be superior in comparison to standard drugs used in the study.

hERG Inhibition Assay

To test if the compounds of the present disclosure have any safety risk by inhibiting cardiac ion channel, particularly the potassium channel (Kr, hERG), compounds were tested using electrophysiological assays to evaluate its potential activity on hERG ion channel. The compounds were tested for inhibition of the human ether a go-go related gene (hERG) K+ channel using QPatch HTX automated electrophysiology. 6-Point concentration-response curves were generated using three-fold serial dilutions from a maximum final test concentration of 300 $\mu$M and the results are presented in table 4.

Compounds of Formula I were solubilised to 100 mM in DMSO before dilution in HBPS to 300 $\mu$M. 6-Point concentration-response curves were generated using 3.16-fold serial dilutions from the top test concentration.

Procedure:

Electrophysiological recordings were made from a Chinese Hamster Ovary cell line stably expressing the full-length hERG potassium channel. Single cell ionic currents were measured in whole-cell patch clamp configuration at room temperature (21-23° C.) using the QPatch HTX platform (Sophion). Intracellular solution contained (mM): 120 KF, 20 KCl, 10 EGTA, 10 HEPES and was buffered to pH 7.3. The extracellular solution (HEPES-buffered physiological saline, HBPS) contained (mM): 145 NaCl, 4 KCl, 2 $CaCl_2$), 1 $MgCl_2$, 10 HEPES, 10 glucose, buffered to pH7.4. Cells were clamped at a holding potential of −80 mV. Cells were stepped to +20 mV for 2 s then −40 mV for 3 s before returning to the holding potential. This sweep was repeated 10 times at 10 s intervals. hERG currents were measured from the tail step and referenced to the holding current. Compounds were then incubated for 2 minutes prior to a second measurement of ion channel current using an identical pulse train.

TABLE 4 hERG IC$_{50}$ values

| Compound | hERG IC$_{50}$ (μM) |
|---|---|
| 1 | >100 |
| 2 | 124 |
| 3 | 25 |
| 4 | 36 |
| 5 | 71 |
| 7 | >300 |
| 8 | 58 |
| 10 | 19 |
| Cisapride | 0.15 |

Intravenous Formulation of Compound 2 for Pharmacokinetic (PK) Studies

Compound 2 was formulated in 10% L-Ascorbic acid solution in water to achieve the desirable solubility for intravenous route of administration and adjusted to pH 4 by 1N NaOH.

Procedure: Weighed appropriate amount of the Compound 2 to be tested and dissolved in 1 ml of the 10% ascorbic acid solution. (Vortex for a few seconds if the compound doesn't dissolve instantly). Sonicated the compound solution at 37° C. for 5 minutes using a bath sonicator to obtain a visually clear solution. The above prepared solution was pH adjusted to pH~4 with 1N NaOH solution (w/v) with sonication (final Formulation pH~4). The details of the Formulation solubility of Compound 2 is given in the Table 5.

TABLE 5

IV Formulation solubility

| Formulation Composition | Solubility in 10% L-ascorbic acid in fresh MilliQ water(v/v), Final pH~2.8 |
|---|---|
| Compound 2 15% L-Ascorbic acid | 15 mg/ml |
| Water for injection or Fresh MiliQ water | |
| 1N NaOH solution for pH adjustment | |

The prepared IV formulation of Compound 2 were observed to be stable at room temperature for more than 24 hours.

In Vivo Pharmacokinetic (PK) Studies in Rats

The rat pharmacokinetic studies were carried out in Sprague-Dawley (SD) rats to estimate the plasma clearance, volume of distribution, terminal half-life and oral bioavailability of Compound 2 following 1 hr intravenous infusion (IV) and oral gavge.

The Compound 2 exhibited moderate clearance, low volume of distribution and moderate half life and good oral bioavailability in SD rats. Dose proportional increase in AUC and Cmax was observed during IV infusion and Oral dosing of Compound 2 at 5, 10, 30 & 100 mg/kg doses in SD rats. This study suggest that the Compound 2 has desirable pharmacokinetic profile to keep blood levels of the parent above the MICs to demonstrate efficacy in rat infection models by IV infusion administration.

Procedure: The objective of this study was to investigate the pharmacokinetic profile of Example 12, following single ascending doses via intravenous (IV) constant rate infusion for 1 h, in male Sprague Dawley rats. The study was performed using the following study design (n=3/group). For Oral dosing, Rats were dosed orally by gavage needle. The required dose volume of the appropriate test formulations were taken in a graduated syringe and administered slowly. Overnight fasted animals were used for dosing and feed was provided 4 hr post dosing. The pharmacokinetic experimental design for Compound 2 is tabulated in the Table 6 below:

TABLE 6

Pharmacokinetic experimental design for Compound 2

| Treatment | Group | Route | No. of animals | Dose (mg/kg) | Conc. in formulation (mg/mL) | Infusion rate (mL/min/Kg) | Dose Volume (mL/kg) | Formulation vehicle |
|---|---|---|---|---|---|---|---|---|
| | G1 | G1 to | 3 | 5 | 0.5 | 0.167 | 10 | 10% L-ascorbic |
| | G2 | G4 | 3 | 30 | 3 | | mL/kg | acid solution in |
| | G3 | IV | 3 | 100 | 10 | | for IV | water for injection |
| | G4 | [Infusion] | 3 | 150 | 15 | | infusion | and adjusted to pH4 |
| | G5 | G5 to | 3 | 30 | 3 | | | by using 1N NaOH |
| | G6 | G7 | 3 | 100 | 10 | | | 15% L-ascorbic |
| | G7 | PO | 3 | 300 | 30 | | | acid solution in |
| | | | | | | | | water for injection |
| | | | | | | | | used for |
| | | | | | | | | 150 mg/kg PK |
| | | | | | | | | Tween80: 2% |
| | | | | | | | | HPMC in water |
| | | | | | | | | (1:99 v/v) for oral |
| | | | | | | | | gavage |

Serial blood sampling was used for blood collection. Blood samples were collected at pre-dose, 0.25, 0.5 h (during infusion), 1 h (end of infusion) and 0.033, 0.25, 0.5, 1, 2, 4, 8 and 24 h, post infusion. At each time point about 100 µL of blood was collected from the jugular vein into a labeled microfuge tube containing 200 mM $K_2$EDTA solution (20 µL per mL of blood) and equivalent volume of heparinized saline was replaced following sample collection. The blood samples were processed to obtain the plasma samples within 30 min of scheduled sampling time. All plasma samples were stored below −60° C. until bioanalysis.

Plasma samples were analyzed for Compound 2 using a fit-for purpose LC-MS/MS method with a lower limit of quantification (LLOQ) of 8.1 ng/mL. The pharmacokinetic parameters of Compound 2 were calculated using the non-compartmental analysis tool of validated Phoenix® WinNonlin® software (version 6.4) with linear up and log down method for estimating AUC.

Male Sprague Dawley rats (8-12 weeks of age, weighing 280±20 g at the time of dosing) used in the study were obtained from Invigo Research laboratories, USA. Anesthetic solution (Ketamine and xylazine) was prepared by mixing 2 mL of Ketamine (50 mg/mL) with 0.5 mL of Xylazine (20 mg/mL). Rats were anaesthetized by ketamine and xylaxine solution by intra-peritoneal route at 1 mL/kg dose. The jugular and femoral veins of rat were cannulated, and the study was performed 48 h post cannulation. All animals were fasted overnight before dose administration and food was provided 4 h post dose administration. All animals received water ad libitum during the study period. The IV and Oral pharmacokinetic profile Compound 2 presented in Table 7.

TABLE 7

Pharmacokinetic profile Compound 2

| Parameter | 5 mg/kg, IV | 30 mg/kg, IV | 100 mg/kg, IV | 150 mg/kg, IV |
|---|---|---|---|---|
| $C_{max}$ (µg/ml) | 2.8 ± 0.97 | 25.17 ± 0.61 | 93.44 ± 4.4 | 111.8 ± 7.58 |
| $T_{max}$ (h) | 0.76 ± 0.02 | 1.0 ± 0.0 | 1.0 ± 0.0 | 2 ± 0.0 |
| $AUC_{inf}$ (h*µg/ml) | 1.87 ± 0.35 | 21.80 ± 0.15 | 118.1 ± 13.6 | 172.18 ± 10.74 |
| $AUC_{last}$ (h*µg/ml) | 1.87 ± 0.35 | 21.78 ± 0.15 | 118.0 ± 13.6 | 172.1 ± 10.75 |
| Vd (L/kg) | 6.4 ± 1.07 | 4.94 ± 1.8 | 5.57 ± 0.56 | 5.38 ± 1.1 |
| CLp (L/h/kg) | 2.74 ± 0.52 | 1.38 ± 0.1 | 0.85 ± 0.1 | 0.87 ± 0.06 |
| Vss (L/kg) | 1.09 ± 0.13 | 0.62 ± 0.05 | 0.69 ± 0.02 | 0.73 ± 0.07 |
| $t_{1/2}$ (h) | 1.53 ± 0.07 | 2.45 ± 0.78 | 4.53 ± 0.12 | 4.24 ± 0.67 |

| Parameter | 10 mg/kg PO | 30 mg/kg, PO | 100 mg/kg, PO | 300 mg/kg, PO |
|---|---|---|---|---|
| $C_{max}$ (µg/ml) | 2.58 ± 0.075 | 8.50 ± 2.4 | 9.79 ± 1.1 | 11.11 ± 3.1 |
| $T_{max}$ (h) | 0.25 ± 0 | 0.5 ± 0 | 0.33 ± 0.14 | 1.0 ± 0 |
| $AUC_{inf}$ (h*µg/ml) | 1.24 ± 0.1 | 7.54 ± 1.62 | 14.39 ± 4.6 | 27.24 ± 17.5 |
| Bioavailability* (F, %) | 33.3 ± 3.1 | 66.8 ± 14.4 | 38.4 ± 12.4 | 24.23 ± 15.6 |
| $t_{1/2}$ (h) | 1.84 ± 0.15 | 1.70 ± 0.5 | 5.32 ± 2.1 | 2.2 |

*5 mg/kg IV infusion PK AUC used for calculating the oral bioavaiability

In Vivo Efficacy of Compound 2 in Rat Infection Models:
In Vivo Efficacy in Rat Thigh *E. coli* and *K. pneumoniae* Model:

Compound 2 was tested in rat thigh infection model following intravenous infusion of compound at doses of 100 mg/kg once, 30 mg/kg once daily over a period of 1 hr to assess its efficacy. This study was performed following all ethical practices as laid down in the guidelines for animal care (Registration number No. 1852/PO/Rc/S/16/CPCSEA). The study was approved by the Institutional Animals Ethics Committee (IAEC) of the test facility. The formulation used was 10% of L-ascorbic acid in fresh MilliQ water (w/v) with pH adjusted to 4.0 with 1N NaOH. On Day-4 (4 days prior to the desired date of infection), each rat was dosed with a single intra-peritoneal injection of cyclophosphamide equivalent to 150 mg/kg and returned to its cage. On Day-1 (a day prior to infection) each rat received a dose equivalent to 100 mg/kg of Cyclophosphamide. This procedure ensured that animals will be neutropenic on day 0. On the day of the infection, the overnight culture of the appropriate microorganisms [*E. coli* [ATCC25922]/*A. baumannii* [ATCC19606]/*K. pneumoniae* [ATCC13883] was adjusted to 1 OD [equal to ~109 CFU/mL], centrifuged and the cells pelleted. The pelleted cells were suspended in sterile normal saline to obtain 107 CFU/ml and used for infection. The inoculum was serially diluted ten-fold in sterile CSDB broth and 0.05 ml of six dilutions were plated onto CSDA agar plates to determine the viable count (CFU/ml) of inoculum. All animals were divided into different groups as specified in the experimental design for each microorganism. All infections were conducted in a biological safety cabinet, with appropriate personnel protection. Infection was done by injecting 0.2 ml of inoculum [approximately 1×107 CFU/ml in broth] of the appropriate microorganism using a 1.0 ml syringe and needle, post-laterally into the right thigh of the animal [approximately 2×106 CFU/thigh]. A gentle shaking/mixing of inoculum between two animals was followed for uniform distribution.

Two hours post infection, animals in groups 4, 5 and 6 were administered intravenously with Compound 2, as a constant rate infusion (duration of infusion 1 h), under Ketamine 60 mg/kg IP+Xylazine 10 mg/kg IP anesthesia, at a dose volume of 10 ml/kg, at the rate of 0.16 ml/min. The dose levels of Compound 2 were 10, 30 and 100 mg/kg. Ciprofloxacin [10 mg/kg] and vehicle [10% of L-ascorbic acid in fresh MilliQ water (w/v) with pH adjustment [to pH~4.0] with 1N Sodium hydroxide solution (w/v)] were dosed intravenously as single bolus doses. The total duration of the study was 10 h.

Animals were sacrificed 10 hr post infection and thigh tissues were harvested to enumerate the bacterial CFU count. Thigh muscles were aseptically excised, weighed, and placed into 1 ml of sterile CSDB broth, and homogenized (Omni Tip (220 V hand held)). Serial ten-fold dilutions of the thigh homogenates were prepared in sterile lactose broth and 0.05 mL of four dilutions for each thigh was plated onto CSDA agar plates. Bacterial colonies were enumerated following overnight incubation at 370 C. Bacterial densities were estimated as Log 10 CFU/gram thigh. The Mean±SD Log 10 CFU/gram thigh was estimated in each group. Significant differences between group means and control will be analyzed by One-way ANOVA, followed by a Dunnett's multiple comparison test, using Graphpad Prism at 95% confidence levels. A P value of <0.05 was considered as significant. The results of the efficacy study are presented in Table 8.

TABLE 8

Efficacy of Compound 2 against *E. coli* [ATCC25922] in a Neutropenic Thigh Infection Model in Rat

| Treatment | $Log_{10}$ CFU/g thigh | | | MEAN ± SD ($Log_{10}$ CFU/g thigh) | Mean Log 10 CFU/thigh reduction (wrt 2 h PI control: 5.04 $Log_{10}$CFU/g thigh) |
|---|---|---|---|---|---|
| Early Infection Control [2 h PI] | 5.94 | 5.62 | 6 | 5.85 ± 0.2 | NA |
| Infection control [vehicle] | 6.72 | 7.74 | 7.24 | 7.23 ± 0.51 | −1.38 |
| Ciprofloxacin [10 mg/kg, i.v. bolus] | 3.74 | 3.94 | 3.52 | 3.73 ± 0.21* | 2.12 |
| Compound 2[3 mg/kg, i.v., 1 h infusion] | 5.37 | 4.64 | 5.23 | 5.08 ± 0.39# | 0.77 |
| Compound 2[10 mg/kg, i.v., 1 h infusion] | 4.44 | 4.57 | 4.21 | 4.41 ± 0.18* | 1.44 |
| Compound 2 [30 mg/kg, i.v., 1 h infusion] | 2.66 | 2.6 | 3.24 | 2.83 ± 0.35* | 3.02 |

TABLE 9

Efficacy of Compound 2 against *K. pneumoniae* [ATCC13883] in a Neutropenic Thigh Infection Model in Rat

| Treatment | $Log_{10}$ CFU/g thigh | | | MEAN ± SD ($Log_{10}$ CFU/g thigh) | Mean Log 10 CFU/thigh reduction (wrt 2 h PI control: 5.04 $Log_{10}$CFU/g thigh) |
|---|---|---|---|---|---|
| Early Infection Control [2 h PI] | 4.54 | 5.14 | 5.43 | 5.04 ± 0.45 | |
| Infection control [vehicle] | 6.45 | 6.69 | 6.92 | 6.69 ± 0.24 | −1.65 |
| Ciprofloxacin [10 mg/kg, i.v. bolus] | 3.22 | 3.25 | 3.42 | 3.30 ± 0.11* | 1.74 |
| Compound 2[3 mg/kg, i.v., 1 h infusion] | 3.95 | 3.87 | 3.91 | 3.91 ± 0.04* | 1.13 |
| Compound 2[10 mg/kg, i.v., 1 h infusion] | 3.74 | 3.26 | 3.84 | 3.61 ± 0.31* | 1.43 |
| Compound 2|30 mg/kg, i.v., 1 h infusion] | 2.48 | 2.29 | 2.92 | 2.56 ± 0.32* | 2.48 |

Example 2 showed significant dose dependent bactericidal efficacy with respect to 2 h Post Infection (PI) control at 3, 10 and 30 mg/kg, and the efficacy was comparable to standard drug ciprofloxacin at similar dose (10 mg/kg).

*(P<0.05) Significantly different from Infection control 2 hr PI:
(P<0.05) Significantly different from Infection control 10 hr PI.

In Vivo Efficacy in Rat Urinary Tract Infection (UTI) *E. coli* Model:

The purpose of this study is to assess the efficacy of Compound 2 against *E. coli* [ATCC25922] following single dose intravenous infusion doses of 3, 10 and 30 mg/kg in a Urinary Tract Infection Rat Model.

Procedure

Prior to the start of the infection process all animals were divided into different groups. All grouped cages of animals were carried to a procedure room, close to a biological safety cabinet. All infections were conducted in a biological safety cabinet, with appropriate personnel protection. Animals were anaesthetized by intraperitoneal injection of ketamine & xylazine (60+10 mg/kg i.p.) cocktail. Once the animals were in a sufficiently deep plane of anaesthesia as monitored by pedal reflex, the abdominal wall of each rat was shaved with electric clippers and the skin was cleansed with 10% povidine iodine. After a 1.5 to 2 cm lower abdominal wall incision, the abdominal wall muscles were separated with blunt dissection. The urinary bladder was isolated and exposed, the urine inside the bladder was removed and 0.1 ml of sterile saline or bacterial culture *E. coli* (approximately 1×108 CFU/animal) was injected into the bladder. After the replacement of the bladder to its original location, the abdominal muscles were approximated using suture and the skin was closed. The wounds were cleansed using 10% povidine iodine.

The IV formulation vehicle used was 10% of L-ascorbic acid in fresh MilliQ water (w/v) with pH adjusted to 4.0 with 1N Sodium hydroxide solution (w/v), and the dose volume was 10 mL/kg. Meropenem was prepared in MilliQ water and the pH of solution was adjusted to 4.5 using HCl. Four hours post infection, animals were dosed intravenously, as single doses (for test compounds), as a constant rate infusion, under Ketamine 60 mg/kg IP+Xylazine 10 mg/kg IP anesthesia, at a dose volume of 10 ml/kg, at the rate of 0.03 ml/min. The dose levels of the test compounds were 3, 10 and 30 mg/kg. Meropenem was administered as a single bolus dose at a dose volume of 5 ml/kg.

All the animals were sacrificed at 24 h post infection, as specified in experimental design, by an overdose of $CO_2$ in an appropriate exposure chamber. The group 1 animals were sacrificed at 4 h post infection.

The euthanized animals were dipped into 70% ethanol for surface decontamination. The organs were removed aseptically; the bladder was cut away near the urethra, and the kidneys were removed by blunt dissection to avoid bleeding. The bladder and each kidney separately were be homogenized in PBS. The CFU per milliliter homogenate of bladder, & kidney were determined after 18 to 24 h of incubation at 37° C. The number of bacteria per organ was enumerated and the results of the study are presented in Table 9 and 10.

TABLE 10

Efficacy of Compound 2 against E. coli [ATCC25922] in Urinary Tract Infection Rat Model-Kidneys

| Treatment | Log$_{10}$ CFU/g (Left Kidney) | | | Log$_{10}$ CFU/g (Right Kidney) | | | MEAN ± SD (Log$_{10}$ CFU/g kidneys) | Mean Log$_{10}$CFU/g kidney reduction (wrt 4 h PI control: 4.53 Log$_{10}$CFU/g kidneys) |
|---|---|---|---|---|---|---|---|---|
| Early Infection Control [4 h PI] | 4.66 | 4.22 | 4.89 | 4.28 | 4.61 | 4.51 | 4.53 ± 0.25 | |
| Infection control [vehicle 10 h PI] | 5.29 | 5.32 | 5.11 | 5.18 | 5.24 | 5.48 | 5.27 ± 0.13 | −0.74 |
| Meropenem [30 mg/kg, i.v. bolus] | 3.61 | 3.92 | 4.06 | 3.41 | 4.12 | 3.87 | 3.83 ± 0.27* | 0.70 |
| Compound 2 [3 mg/kg, i.v., 1 h infusion] | 5.39 | 5.17 | 5.24 | 4.68 | 4.90 | 5.39 | 5.13 ± 0.28# | −0.60 |
| Compound 2 [10 mg/kg, i.v., 1 h infusion] | 4.12 | 3.78 | 4.46 | 4.11 | 3.65 | 3.61 | 3.95 ± 0.33* | 0.58 |
| Compound 2 [30 mg/kg, i.v., 1 h infusion] | 3.22 | 3.36 | 2.80 | 2.77 | 2.75 | 2.55 | 2.91 ± 0.31* | 1.62 |

*($P < 0.05$) significantly different from Infection control 4 hr PI;
($P < 0.05$) significantly different from Infection control 24 hr PI.

TABLE 11

Efficacy of Compound 2 against E. coli [ATCC25922] in Urinary Tract Infection Rat Model-bladder

| Treatment | Log$_{10}$ CFU/ml Bladder | | | MEAN ± SD (Log$_{10}$ CFU/ml Bladder) | Mean Log$_{10}$ CFU/ml Bladder reduction (wrt 4 h PI control: 5.72 CFU/ml Bladder) |
|---|---|---|---|---|---|
| Early Infection Control [4 h PI] | 5.53 | 6.26 | 5.38 | 5.72 ± 0.47 | |
| Infection control [vehicle 10 h PI] | 7.43 | 7.52 | 7.13 | 7.36 ± 0.2 | −1.64 |
| Meropenem [30 mg/kg, i.v. bolus] | 4.87 | 4.33 | 4.89 | 4.69 ± 0.32* | 1.03 |
| Compound 2 [3 mg/kg, i.v., 1 h infusion] | 5.43 | 6.16 | 6.08 | 5.89 ± 0.4# | −0.17 |
| Compound 2 [10 mg/kg, i.v., 1 h infusion] | 5.02 | 4.61 | 4.76 | 4.8 ± 0.2# | 0.92 |
| Compound 2 [30 mg/kg, i.v., 1 h infusion] | 4.19 | 3.90 | 3.58 | 3.89 ± 0.3* | 1.83 |

*($P < 0.05$) significantly different from Infection control 4 hr PI;
($P < 0.05$) significantly different from Infection control 24 hr PI.

Compound 2 showed significant dose dependent bactericidal effect with respect to 4 h PI control at 10 and 30 mg/kg and was bacteriostatic at 3 mg/kg when compared to the 4 h PI control and the efficacy was better than standard drug meropenem at similar dose (30 mg/kg).

In Vivo Efficacy in Rat Lung P. aeruginosa Model:

The purpose of this study was to evaluate the efficacy of Compound 2 against P. aeruginosa [ATCC27853], following single dose intravenous infusion doses of 10, 30 and 100 mg/kg in a neutropenic lung infection model in rats.

Procedure

Prior to the start of the infection process, all animals were divided into different groups. All grouped cages of animals were carried to a procedure room, close to a biological safety cabinet. All infections were conducted in a biological safety cabinet, with appropriate personnel protection. Animals were placed into an induction chamber and anaesthesia was induced by exposing the animals to 3-5% Isoflurane in an oxygen flow set at approximately (~) 1 liter per minute (LPM). Once the animals were in a sufficiently deep plane of anaesthesia as monitored by pedal reflex, they were removed and infected (2). Infection was initiated by instilling 0.07 ml (containing ~1×10$^9$ CFU/ml) of the inoculum; 35 µl into each nostril of the anesthetized animal using 100 µl pipette (~7×10$^7$ CFU/animal). A gentle mixing of inoculum between two animals was followed for uniform distribution.

The IV formulation vehicle used for Compound 2 was 10% of L-ascorbic acid in fresh MilliQ water (w/v) with pH adjusted to 4.0 with 1N Sodium hydroxide solution (w/v), and the dose volume was 10 mL/kg. Meropenem was formulated in saline. Four hours post infection, animals were dosed intravenously, as single doses, by infusion, under Ketamine 60 mg/kg IP+Xylazine 10 mg/kg IP anesthesia, at a dose volume of 10 ml/kg, at a constant rate of 0.03 ml/min. The dose levels of the test Compound 2 were 10, 30 and 100 mg/kg.

All the animals in groups were sacrificed at 24 h post infection, as specified in experimental design, by an overdose of $CO_2$ in an appropriate exposure chamber. The group 1 animals were sacrificed at 4 hrs post infection. The euthanized animals were dipped into 70% ethanol for surface decontamination. Entire Lung was aseptically isolated, weighed and placed into 1 mL of sterile CSDB broth, and homogenized (Omni Tip (220 V hand held)). Serial ten-fold dilutions of the lungs homogenates were prepared in sterile CSD broth and 0.05 mL of four dilutions for each tissue was plated onto CSDA agar plates. Bacterial colonies were enumerated following overnight incubation at 37° C. Bacterial densities were estimated as Log$_{10}$ CFU/g lung. The Mean±SD Log$_{10}$ CFU/g lung was estimated in each group. Significant differences between group means and control were analyzed by One-way ANOVA, followed by a Dunnett's multiple comparison test, using Graphpad Prism at 95% confidence levels. A P value of <0.05 was considered as significant and the results of the study was presented in Table 10.

TABLE 12

Efficacy of Compound 2 against *P. aeruginosa* [ATCC27853] in a Neutropenic Lung Infection Model in Rat

| Treatment | $Log_{10}$ CFU/g Lung | | | MEAN ± SD ($Log_{10}$ CFU/g Lung) | Mean Log 10 CFU/g lung reduction (wrt 4 h PI control: 6.52 $Log_{10}$CFU/g lung) |
|---|---|---|---|---|---|
| Early Infection Control [4 h PI] | 6.96 | 6.32 | 6.27 | 6.52 ± 0.38 | NA |
| Infection control [vehicle] | 9.05 | 9.03 | 9.09 | 9.05 ± 0.03 | −2.53 |
| Meropenem [30 mg/kg, i.v. bolus] | 5.35 | 5.36 | 5.59 | 5.43 ± 0.14* | 1.09 |
| Compound 2 [3 mg/kg, i.v., 1 h infusion] | 7.99 | 8.02 | 8.26 | 8.09 ± 0.14# | −1.57 |
| Compound 2 [10 mg/kg, i.v., 1 h infusion] | 7.34 | 6.98 | 6.46 | 6.93 ± 0.44# | −0.41 |
| Compound 2 [30 mg/kg, i.v., 1 h infusion] | 5.30 | 5.63 | 5.14 | 5.35 ± 0.25* | 1.17 |
| Compound 2 [100 mg/kg, i.v., 1 h infusion] | 3.12 | 3.20 | 2.98 | 3.1 ± 0.12* | 3.42 |

Data analysis: One-way Annova followed by Dunnett's Multiple Comparison Test; *($P < 0.05$) significantly different from Infection control 4 hr PI.
($P < 0.05$) significantly different from Infection control 24 hr PI.

Compound 2 showed significant efficacy at 30 mg/kg and 100 mg/kg doses with respect to early infection control and the efficacy was comparable to standard drug meropenem at similar dose (30 mg/kg).

Advantage

The above-mentioned implementation examples as described on this subject matter and its equivalent thereof have many advantages, including those which are described.

The compounds of the present disclosure show high antibacterial activity against various pathogens including Gram-positive and Gram-negative bacteria through the inhibition of bacterial topoisomerase via a novel mechanism.

The compounds of the present disclosure demonstrate high degree of selectivity against hERG channel (cardiac potassium channel) and may be devoid of cardio toxicity in animal and human.

Representative exemplification of the present disclosure demonstrates of desirable pharmacokinetic profile in rat and efficacious in various rat infection models thus confirming in vivo proof of principle in animal through inhibition of bacterial topoisomerase Although the subject matter has been described in considerable detail with reference to certain embodiments thereof, other embodiments are possible. As such, the spirit and scope of the invention should not be limited to the description of the embodiments contained herein.

We claim:
1. A compound of Formula I

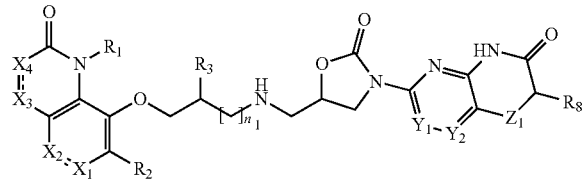

Formula I or its stereoisomers, pharmaceutically acceptable salts, hydrates, solvates, tautomers, polymorphs, racemic mixtures, or optically active forms, thereof,
wherein
$R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated, carbocyclyl or heterocyclyl ring, wherein the heterocyclyl ring is optionally substituted with up to three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with up to three heteroatoms independently selected from O, N or S;
$R_9$ is selected from hydrogen, or $C_{1-6}$ alkyl; $R_2$ is selected from hydrogen, fluorine, chlorine, cyano, $C_{1-6}$ alkoxy, or hydroxyl;
$R_3$ is selected from hydrogen, $C_{1-6}$ alkyl, fluorine, $C_{1-6}$ alkoxy, hydroxyl, or amino;
$X_1$ is N or $CR_4$;
$R_4$ is selected from hydrogen, halogen, cyano, $C_{1-6}$ alkoxy, $C_{1-6}$ haloalkyl, $C_{1-6}$ haloalkoxy, or $C_{1-6}$ alkyl;
$X_2$ is N or $CR_5$;
$R_5$ is selected from hydrogen, halogen, cyano, $C_{1-6}$ alkoxy, $C_{1-6}$ haloalkyl, $C_{1-6}$ haloalkoxy, or $C_{1-6}$ alkyl;
$X_3$ is N or $CR_6$; and $X_4$ is $CR_6$ when dotted line (----) represents a bond;
$R_6$ is selected from hydrogen, cyano, $C_{1-6}$ alkyl, $C_{1-6}$ alkylamino, $C_{1-6}$ alkoxy, $C_{1-6}$ haloalkoxy, or COOH; or
$X_3$ is $CH_2$ or O; and $X_4$ is $CH_2$ when dotted line (----) represents no bond;
$n_1$ is 0 to 2;
$Y_1$, and $Y_2$ are independently selected from N or $CR_7$;
$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;
$Z_1$ is selected from O, S, NH, or $CH_2$; and
$R_8$ is selected from hydrogen, hydroxyl, $C_{1-6}$ alkyl, or fluorine.

2. The compound as claimed in claim 1, or its stereoisomers, pharmaceutically acceptable salts, hydrates, solvates, tautomers, polymorphs, racemic mixtures, or optically active forms thereof,
wherein
$R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with up to three heteroatoms independently selected from O, N or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_9$, $SO_2NHR_9$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino or 3-7 membered saturated or unsaturated heterocyclyl ring optionally substituted with up to three heteroatoms independently selected from O, N or S; $R_9$ is selected from hydrogen, or $C_{1-6}$ alkyl; $R_2$ is selected from hydrogen, fluorine, chlorine, $C_{1-4}$ alkoxy, cyano, or hydroxyl; $R_3$ is selected from hydrogen, fluorine, $C_{1-4}$ alkoxy, hydroxyl, or amino; $X_1$ is N or $CR_4$; $R_4$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_2$ is N or $CR_5$; $R_5$ is selected from hydrogen, halogen, cyano, $C_{1-4}$ alkoxy, $C_{1-4}$ haloalkyl, $C_{1-4}$ haloalkoxy, or $C_{1-4}$ alkyl; $X_3$ is N or $CR_6$; and $X_4$ is $CR_6$ when dotted line (----) represents a bond; $R_6$ is selected from hydrogen, cyano, $C_{1-4}$ alkyl, $C_{1-4}$ alkylamino, $C_{1-4}$ alkoxy, $C_{1-4}$ haloalkoxy, and COOH; or $X_3$ is $CH_2$ or O; and $X_4$ is $CH_2$ when dotted line (----) represents no bond; $n_1$ is 0 to 2; $Y_1$, and $Y_2$ are independently selected from N or $CR_7$; $R_7$ is selected from hydrogen, halogen, cyano, $C_{1-4}$ alkoxy, $C_{1-4}$ haloalkyl, $C_{1-4}$ haloalkoxy, or $C_{1-4}$ alkyl; $Z_1$ is selected from O, S, NH, or $CH_2$; and $R_8$ is selected from hydrogen, hydroxyl, $C_{1-6}$ alkyl, or fluorine.

3. The compound as claimed in claim 1, or its stereoisomers, pharmaceutically acceptable salts, hydrates, solvates, tautomers, polymorphs, racemic mixtures, or optically active forms thereof, wherein $R_1$ is selected from $C_{1-4}$ alkyl, $C_{3-4}$ cycloalkyl, $C_{1-4}$ alkylamino, or 4-7 membered saturated carbocyclyl or heterocyclyl ring, wherein the heterocyclyl ring is optionally substituted with up to three heteroatoms independently selected from O, N or S, wherein $C_{1-4}$ alkyl, $C_{1-4}$ haloalkyl, $C_{3-4}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, $O-PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ aminocycloalkyl, $C_{3-5}$ cycloalkylhydroxy, $C_{1-4}$ alkylamino, or 3-7 membered saturated or unsaturated heterocyclyl ring optionally substituted with up to three heteroatoms independently selected from O, N or S; $R_2$ is selected from hydrogen, fluorine, $C_{1-2}$ alkoxy, cyano, or hydroxyl; $R_3$ is selected from hydrogen, fluorine, $C_{1-2}$ alkoxy, hydroxyl, or amino; $X_1$ is N or $CR_4$; $R_4$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_2$ is N or $CR_5$; $R_5$ is selected from hydrogen, halogen, cyano, $C_{1-2}$ alkoxy, $C_{1-2}$ haloalkyl, $C_{1-2}$ haloalkoxy, or $C_{1-2}$ alkyl; $X_3$ is N or $CR_6$; and $X_4$ is CH when dotted line (----) represents a bond; $R_6$ is selected from hydrogen, cyano, $C_{1-2}$ alkyl, $C_{1-3}$ alkylamino, $C_{1-2}$ alkoxy, $C_{1-2}$ haloalkoxy, or COOH; or $X_3$ is $CH_2$ or O; and $X_4$ is $CH_2$ when dotted line (----) represents no bond; $n_1$ is 0 or 1; $Y_1$, and $Y_2$ are independently selected from N or $CR_7$; $R_7$ is selected from hydrogen, halogen, cyano, $C_{1-2}$ alkoxy, $C_{1-2}$ haloalkyl, $C_{1-2}$ haloalkoxy, or $C_{1-2}$ alkyl;

$Z_1$ is selected from O, S, NH, or $CH_2$; and $R_8$ is selected from hydrogen, hydroxyl, $C_{1-6}$ alkyl, or fluorine.

4. The compound as claimed in claim 1, or its stereoisomers, pharmaceutically acceptable salts, hydrates, solvates, tautomers, polymorphs, racemic mixtures, or optically active forms thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CHFCH_2NH_2$, $CH_2CF_2CH_2NH_2$, $CH_2CH_2OPO_3H_2$, $CH_2C(CH_3)_2OH$, $CH_2C(CH_3)_2OPO_3H_2$,

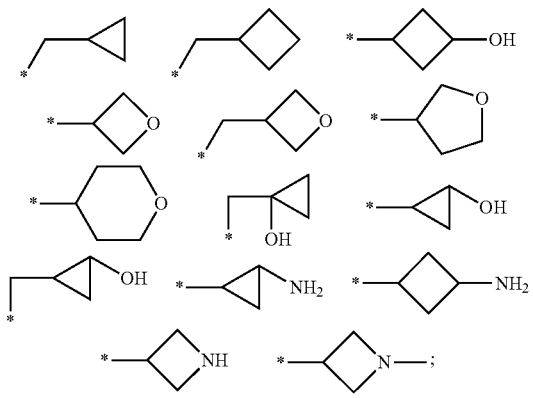

$R_2$ is selected from H, F, Cl, $OCH_3$, CN, or OH; $R_3$ is selected from H, F, $OCH_3$, OH, or $NH_2$;

$X_1$ is N or $CR_4$;

$R_4$ is selected from H, F, CN, $OCH_3$, or $CH_3$; $X_2$ is N or $CR_5$; $R_5$ is selected from H, F, CN, $OCH_3$, $CF_3$, $OCF_3$, or $CH_3$; $X_3$ is N or $CR_6$; and $X_4$ is CH when dotted line (----) represents a bond;

$R_6$ is selected from H, CN, COOH, $CH_2NH_2$, $CH(CH_3)NH_2$, $OCH_3$, $OCF_3$, or $CH_3$;

or $X_3$ is $CH_2$ or O; and $X_4$ is $CH_2$ when dotted line (----) represents no bond;

$n_1$ is 0 or 1;

$Y_1$, and $Y_2$ are independently selected from N or $CR_7$;

$R_7$ is selected from H, F, CN, $OCH_3$, or $CH_3$;

$Z_1$ is selected from O, S, NH, or $CH_2$; and $R_8$ is selected from H, OH, $C_{1-6}$ alkyl, or F.

5. The compound as claimed in claim 1, or its stereoisomers, pharmaceutically acceptable salts, hydrates, solvates, tautomers, polymorphs, racemic mixtures, or optically active forms thereof, which is selected from the group consisting of:

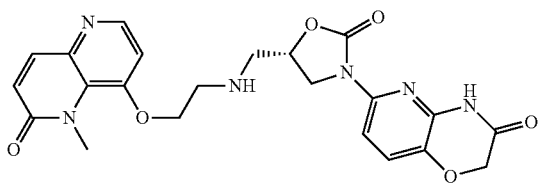 [SMILES: Cn1c(=O)ccc2nccc(OCCNC[C@H]3CN(c4ccc5c(n4)NC(=O)CO5)C(=O)O3)c21]

(S)-6-(5-(((2-((5-methyl-6-oxo-5,6-dihydro-1,5-naphthyridin-4-yl)oxy)ethyl)amino)methyl)-2-oxooxazolidin-3-yl)-2H-pyrido[3,2-b][1,4]oxazin-3(4H)-one (Compound 1),

107

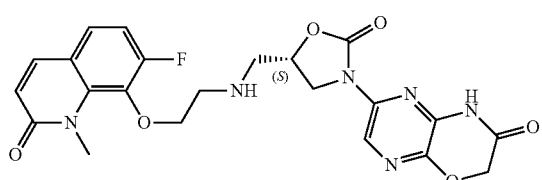

(S)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 2),

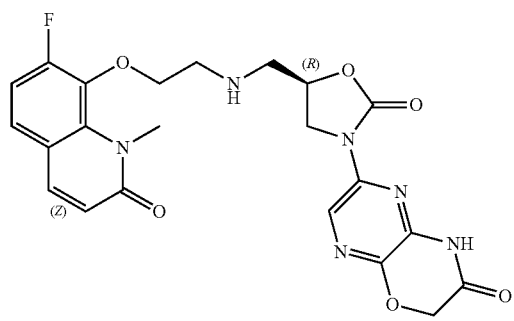

(R)-6-(5-(((2-((7-fluoro-1-methyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 3),

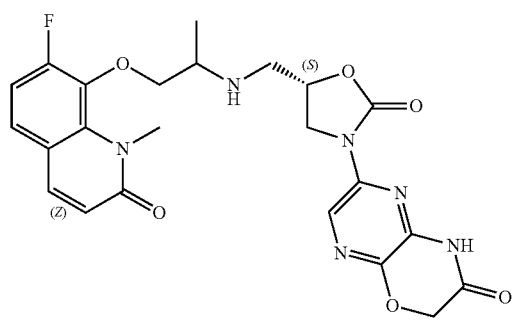

6-((5S)-5-(((1-((7-fluoro-1-methyl-2-oxo-1,2-dihydroquinolin-8-yl)oxy)propan-2-yl)amino)methyl)-2-oxooxazolidin-3-yl)-2H-pyrazino [2,3-b] [1,4]oxazin-3 (4H)-one (Compound 4),

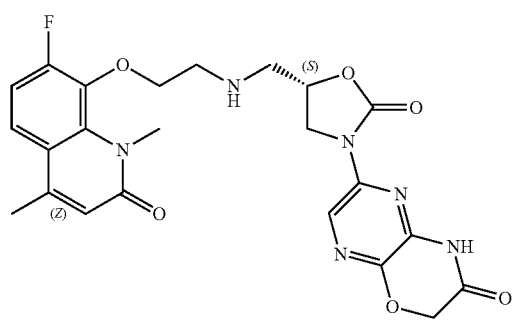

108

(S)-6-(5-(((2-((7-fluoro-1,4-dimethyl-2-oxo-1,2-dihydroquinolin-8-yl)oxy)ethyl)amino)methyl)-2-oxooxazolidin-3-yl)-2H-pyrazino[2,3-b][1,4]oxazin-3(4H)-one (Compound 5),

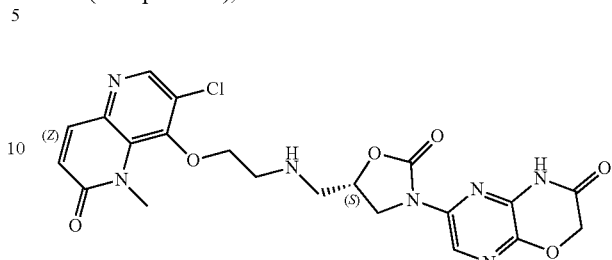

(S)-6-(5-(((2-((3-chloro-5-methyl-6-oxo-5,6-dihydro-1,5-naphthyridin-4-yl)oxy)ethyl)amino)methyl)-2-oxooxazolidin-3-yl)-2H-pyrazino [2,3-b] [1,4]oxazin-3(4H)-one (Compound 6),

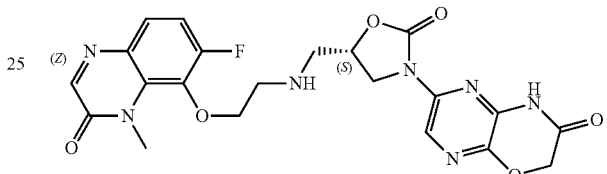

(S)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 7),

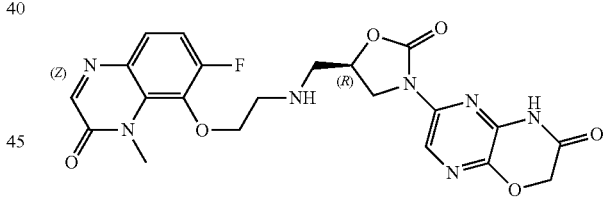

(R)-6-(5-(((2-((6-fluoro-4-methyl-3-oxo-3,4-dihydroquinoxalin-5-yl)oxy)ethyl)amino)methyl)-2-oxooxazolidin-3-yl)-2H-pyrazino[2,3-b][1,4]oxazin-3(4H)-one (Compound 8),

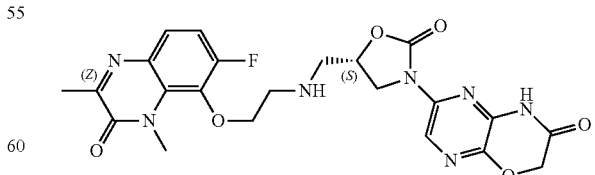

(S)-6-(5-(((2-((6-fluoro-2,4-dimethyl-3-oxo-3,4-dihydroquinoxalin-5-yl)oxy)ethyl)amino)methyl)-2-oxooxazolidin-3-yl)-2H-pyrazino [2,3-6] [1,4]oxazin-3(4H)-one (Compound 9), and

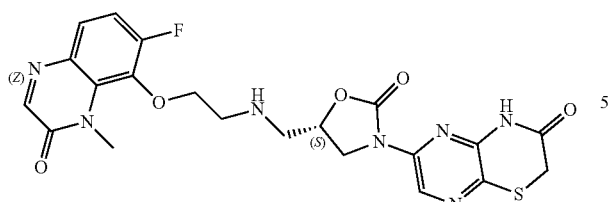

(S)-5-(((2-((6-fluoro-4-methyl-3-oxo-3,4-dihydroquinoxalin-5-yl)oxy)ethyl)amino)methyl)-3-(3-oxo-3,4-dihydro-2H-pyrazino[2,3-b][1,4]thiazin-6-yl)oxazolidin-2-one (Compound 10).

6. A compound of Formula (B)

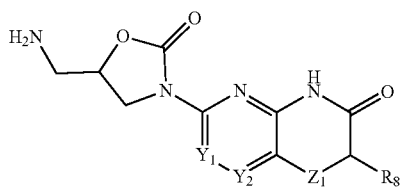

Formula (B)

or its stereoisomers, pharmaceutically acceptable salts, hydrates, solvates, tautomers, polymorphs, racemic mixtures, or optically active forms thereof,
wherein
$Y_1$ is selected from N or $CR_7$;
$Y_2$ is N;
$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;
$Z_1$ is selected from O, S, NH, or $CH_2$; and
$R_8$ is selected from hydrogen, hydroxyl, $C_{1-6}$ alkyl, or fluorine.

7. The compound as claimed in claim 6, or its stereoisomers, pharmaceutically acceptable salts, hydrates, solvates, tautomers, polymorphs, racemic mixtures, or optically active forms thereof, which is selected from the group consisting of:

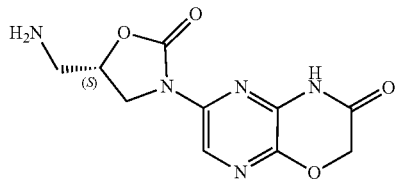

(S)-6-(5-(aminomethyl)-2-oxooxazolidin-3-yl)-2H-pyrazino[2,3-b][1,4]oxazin-3(4H)-one (Intermediate V)

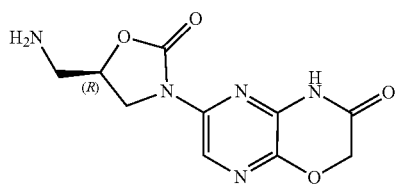

(R)-6-(5-(aminomethyl)-2-oxooxazolidin-3-yl)-2H-pyrazino[2,3-b][1,4]oxazin-3(4H)-one (Intermediate VI)

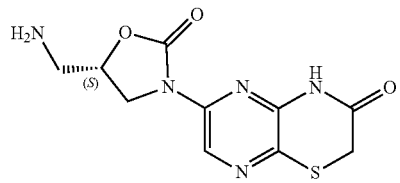

(S)-5-(aminomethyl)-3-(3-oxo-3,4-dihydro-2H-pyrazino[2,3-b][1,4]thiazin-6-yl)oxazolidin-2-one (Intermediate VII).

8. A process of preparation of compounds of Formula (B) as claimed in claim 6, or its stereoisomers, pharmaceutically acceptable salts, hydrates, solvates, tautomers, polymorphs, racemic mixtures, or optically active forms thereof, said process comprising:
  a) reacting a compound of Formula (C), and a compound of Formula (D) in the presence of at least one catalyst and at least one solvent to obtain a compound of Formula (E);
  b) reacting the compound of Formula (E) and at least one nitrogen compound to obtain a compound of Formula (F); and
  c) reducing the compound of Formula (F) to obtain a compound Formula (B).

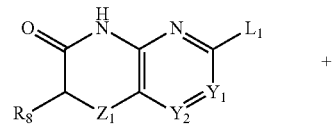

Formula (C)

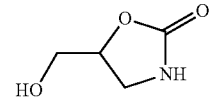

Formula (D)

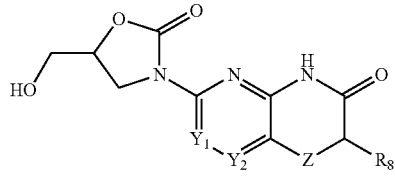

Formula (E)

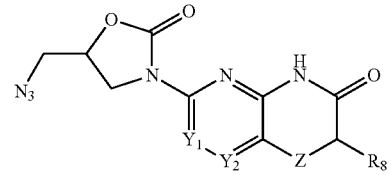

Formula (F)

-continued

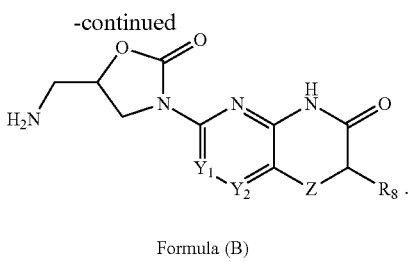

Formula (B)

9. The process as claimed in claim 8, wherein the at least one catalyst is selected from a group consisting of Pd containing catalyst, t-BuXPhos-Pd, Pd(OAc)$_2$, and combinations thereof; the at least one solvent is selected from the group consisting of THF, toluene, dioxane, and combinations thereof, the at least one nitrogen compound is NaN$_3$.

10. The process as claimed in claim 8, wherein reducing the compound of Formula (F) to obtain a compound Formula (B) is carried out in the presence of reducing agent selected from triphenyl phosphine [(PH$_3$P)/THF—H$_2$O], or hydrogen and palladium carbon (H$_2$/Pd—C).

11. A process of preparation of compounds of Formula I as claimed in claim 1, or its stereoisomers, pharmaceutically acceptable salts, hydrates, solvates, tautomers, polymorphs, racemic mixtures, or optically active forms thereof, said process comprising reacting a compound of Formula (A), and a compound of Formula (B)

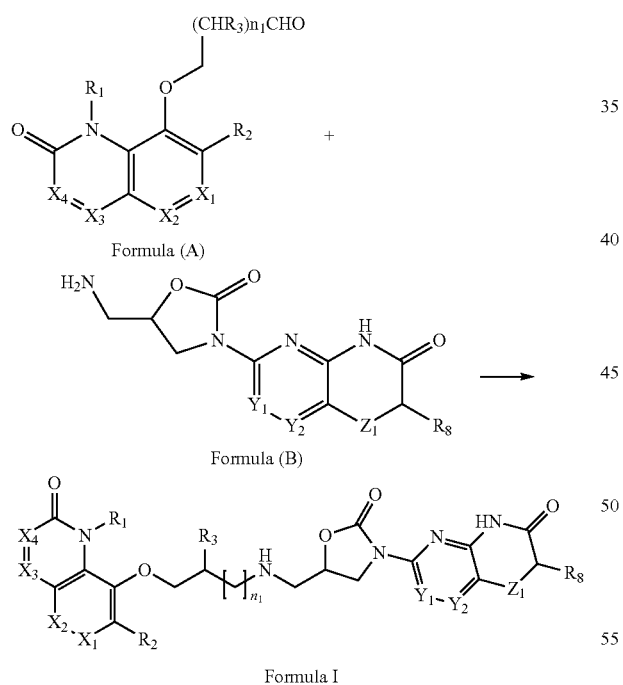

in presence of at least one reducing agent, and an adsorbent to obtain the compounds of Formula I, wherein R$_1$ of Formula (A) is selected from C$_{1-6}$ alkyl, C$_{2-6}$ alkenyl, C$_{3-6}$ cycloalkyl, C$_{1-6}$ alkylamino, C$_{1-6}$ aminoalkylene, or 4-7 membered saturated or unsaturated carbocyclyl or heterocyclyl ring, wherein the heterocyclyl ring is optionally substituted with up to three heteroatoms independently selected from O, N or S, wherein C$_{1-6}$ alkyl, C$_{2-6}$ alkenyl, C$_{3-6}$ cycloalkyl, C$_{1-6}$ alkylamino, C$_{1-6}$ aminoalkylene, and 4-7 membered saturated or unsaturated carbocyclyl or heterocyclyl ring are optionally substituted with 1 to 3 groups independently selected from halogen, amino, hydroxyl, SO$_3$H, O—PO$_3$H$_2$, COOR$_9$, CONHR$_9$, SO$_2$NHR$_9$, methylsulfone, C$_{1-6}$ alkyl, C$_{1-6}$ alkoxy, C$_{1-6}$ haloalkoxy, C$_{3-6}$ cycloalkyl, C$_{3-6}$ cycloalkylamino, C$_{3-6}$ cycloalkylhydroxy, C$_{3-6}$ aminocycloalkyl, C$_{1-6}$ alkylamino, or 3-7 membered saturated or unsaturated heterocyclyl ring optionally substituted with up to three heteroatoms independently selected from O, N or S; R$_9$ is selected from hydrogen, or C$_{1-6}$ alkyl; R$_2$ is selected from hydrogen, fluorine, chlorine, cyano, C$_{1-6}$ alkoxy, or hydroxyl; R$_3$ is selected from hydrogen, C$_{1-6}$ alkyl, fluorine, C$_{1-6}$ alkoxy, hydroxyl, or amino; X$_1$ is N or CR$_4$; R$_4$ is selected from hydrogen, halogen, cyano, C$_{1-6}$ alkoxy, C$_{1-6}$ haloalkyl, C$_{1-6}$ haloalkoxy, or C$_{1-6}$ alkyl; X$_2$ is N or CR$_5$; R$_5$ is selected from hydrogen, halogen, cyano, C$_{1-6}$ alkoxy, C$_{1-6}$ haloalkyl, C$_{1-6}$ haloalkoxy, or C$_{1-6}$ alkyl; X$_3$ is N or CR$_6$; and X$_4$ is CR$_6$ when dotted line (----) represents a bond; R$_6$ is selected from hydrogen, cyano, C$_{1-6}$ alkyl, C$_{1-6}$ alkylamino, C$_{1-6}$ alkoxy, C$_{1-6}$ haloalkoxy, or COOH; or X$_3$ is CH$_2$ or O; and X$_4$ is CH$_2$ when dotted line (----) represents no bond; and n$_1$ is 0 to 2; R$_8$ of Formula (B) is selected from hydrogen, hydroxyl, C$_{1-6}$ alkyl, or fluorine; Y$_1$, and Y$_2$ are independently selected from N or CR$_7$; R$_7$ is selected from hydrogen, halogen, cyano, C$_{1-6}$ alkoxy, C$_{1-6}$ haloalkyl, C$_{1-6}$ haloalkoxy, or C$_{1-6}$ alkyl; Z$_1$ is selected from O, S, NH, or CH$_2$; and R$_1$ of Formula I is selected from C$_{1-6}$ alkyl, C$_{2-6}$ alkenyl, C$_{3-6}$ cycloalkyl, C$_{1-6}$ alkylamino, C$_{1-6}$ aminoalkylene, or 4-7 membered saturated or unsaturated, carbocyclyl or heterocyclyl ring, wherein the heterocyclyl ring is optionally substituted with up to three heteroatoms independently selected from O, N or S, wherein C$_{1-6}$ alkyl, C$_{2-6}$ alkenyl, C$_{3-6}$ cycloalkyl, C$_{1-6}$ alkylamino, C$_{1-6}$ aminoalkylene, and 4-7 membered saturated or unsaturated carbocyclyl or heterocyclyl ring are optionally substituted with 1 to 3 groups independently selected from halogen, amino, hydroxyl, SO$_3$H, O—PO$_3$H$_2$, COOR$_9$, CONHR$_9$, SO$_2$NHR$_9$, methylsulfone, C$_{1-6}$ alkyl, C$_{1-6}$ alkoxy, C$_{1-6}$ haloalkoxy, C$_{3-6}$ cycloalkyl, C$_{3-6}$ cycloalkylamino, C$_{3-6}$ aminocycloalkyl, C$_{3-6}$ cycloalkylhydroxy, C$_{1-6}$ alkylamino, or 3-7 membered saturated or unsaturated heterocyclyl ring optionally substituted with up to three heteroatoms independently selected from O, N or S; R$_9$ is selected from hydrogen, or C$_{1-6}$ alkyl; R$_2$ is selected from hydrogen, fluorine, chlorine, cyano, C$_{1-6}$ alkoxy, or hydroxyl; R$_3$ is selected from hydrogen, C$_{1-6}$ alkyl, fluorine, C$_{1-6}$ alkoxy, hydroxyl, or amino; X$_1$ is N or CR$_4$; R$_4$ is selected from hydrogen, halogen, cyano, C$_{1-6}$ alkoxy, C$_{1-6}$ haloalkyl, C$_{1-6}$ haloalkoxy, or C$_{1-6}$ alkyl; X$_2$ is N or CR$_5$; R$_5$ is selected from hydrogen, halogen, cyano, C$_{1-6}$ alkoxy, C$_{1-6}$ haloalkyl, C$_{1-6}$ haloalkoxy, or C$_{1-6}$ alkyl; X$_3$ is N or CR$_6$; and X$_4$ is CR$_6$ when dotted line (----) represents a bond; R$_6$ is selected from hydrogen, cyano, C$_{1-6}$ alkyl, C$_{1-6}$ alkylamino, C$_{1-6}$ alkoxy, C$_{1-6}$ haloalkoxy, or COOH or X$_3$ is CH$_2$ or O; and X$_4$ is CH$_2$ when dotted line (----) represents no bond; n$_1$ is 0 to 2; Y$_1$, and Y$_2$ are independently selected from N or CR$_7$; R$_7$ is selected from hydrogen, halogen, cyano, C$_{1-6}$ alkoxy, C$_{1-6}$ haloalkyl, C$_{1-6}$ haloalkoxy, or C$_{1-6}$ alkyl; Z$_1$ is selected from O, S, NH, or CH$_2$; and R$_8$ is selected from hydrogen, hydroxyl, C$_{1-6}$ alkyl, or fluorine.

12. The process as claimed in claim 11, wherein the at least one reducing agent is selected from the group consisting of sodium borohydride, sodium cyano borohydride, sodium triacetoxy borohydride, and combinations thereof.

13. The process as claimed in claim 11, wherein the adsorbent is selected from the group consisting of molecular sieves, silica gel, zeolites, anhydrous sodium sulphate, anhydrous magnesium sulphate, activated charcoal, and combinations thereof.

14. A medicament comprising the compound as claimed in claim 1 or its stereoisomers, pharmaceutically acceptable salts, hydrates, solvates, tautomers, polymorphs, racemic mixtures, or optically active forms thereof.

15. A method of treating a disease or condition in a patient wherein said disease or condition is caused by a microorganism selected from the group consisting of Gram-positive, and Gram-negative pathogen comprising administering to the patient the compound as claimed in claim 1 or its stereoisomers, pharmaceutically acceptable salts, hydrates, solvates, tautomers, polymorphs, racemic mixtures, or optically active forms thereof.

16. A pharmaceutical composition comprising a compound of Formula I, as claimed in claim 1 or its stereoisomers, pharmaceutically acceptable salts, hydrates, solvates, tautomers, polymorphs, racemic mixtures, or optically active forms thereof together with a pharmaceutically acceptable carrier.

17. A pharmaceutical composition comprising a compound of Formula I as claimed in claim 1 or its stereoisomers, pharmaceutically acceptable salts, hydrates, solvates, tautomers, polymorphs, racemic mixtures, or optically active forms thereof together with a pharmaceutically acceptable carrier, and in combination with at least one antibiotic.

18. A method for the treatment of a bacterial infection in a subject comprising:
   administering to the subject an effective amount of the compound as claimed in claim 1.

19. The method as claimed in claim 18, wherein the bacterial infection is caused by a Gram-positive or a Gram-negative pathogen.

20. The method as claimed in claim 19, wherein the bacterial infection is caused by *Escherichia coli, Pseudomonas aurigenosa, Klebsiella pneumoniae, Acinetobacter baumannii, Enterobacter cloacae, Staphylococcus aureus, Enterococcus faecalis Enterococcus faecium, Legionella pneumophila, Mycoplasma* pneumonia, *Acinetobacter haemolyticus, Acinetobacter junii, Acinetobacter lwoffi, Burkholderia cepacia, Chlamydophila pneumoniae, Clostridium difficili, Enterobacter aerogenes, Enterobacter cloacae, Moraxella catarrhalis, Neisseria gonorrhoeae, Neisseria meningitides, Proteus mirabilis, Proteus houseri, Citrobacter freundii, Citrobacter kosari, Citrobacter* barakii, *Seratia marcescens, Klebsiella oxytoca, Morganella morganii, Helicobacter pyroli,* or *Mycobacterium tuberculosis.*

21. A pharmaceutical composition comprising a compound of Formula (B) as claimed in claim 6 or its stereoisomers, pharmaceutically acceptable salts, hydrates, solvates, tautomers, polymorphs, racemic mixtures, or optically active forms thereof together with a pharmaceutically acceptable carrier.

22. A pharmaceutical composition comprising a compound of Formula (B) as claimed in claim 6 or its stereoisomers, pharmaceutically acceptable salts, hydrates, solvates, tautomers, polymorphs, racemic mixtures, or optically active forms thereof together with a pharmaceutically acceptable carrier, and in combination with at least one antibiotic.

* * * * *